United States Patent
Tsuji et al.

(10) Patent No.: US 12,123,876 B2
(45) Date of Patent: Oct. 22, 2024

(54) ANTIBODY BINDING TO HEG1 AND USE OF THE ANTIBODY FOR DETECTION AND TREATMENT OF MESOTHELIOMA

(71) Applicants: Kanagawa Prefectural Hospital Organization, Yokohama (JP); The University of Tokyo, Tokyo (JP)

(72) Inventors: Shoutaro Tsuji, Toyko (JP); Taihei Kageyama, Toyko (JP); Kota Washimi, Tokyo (JP); Makiko Tsuji, Tokyo (JP); Rieko Matsuura, Toyko (JP); Mitsuyo Yoshihara, Yokohama (JP); Kohzoh Imai, Tokyo (JP)

(73) Assignees: Kanagawa Prefectural Hospital Organization, Yokohama (JP); The University of Tokyo, Tokyo (JP)

( * ) Notice: Subject to any disclaimer, the term of this patent is extended or adjusted under 35 U.S.C. 154(b) by 288 days.

(21) Appl. No.: 16/077,911

(22) PCT Filed: Jan. 16, 2017

(86) PCT No.: PCT/JP2017/001250
§ 371 (c)(1),
(2) Date: Aug. 14, 2018

(87) PCT Pub. No.: WO2017/141604
PCT Pub. Date: Aug. 24, 2017

(65) Prior Publication Data
US 2019/0071517 A1    Mar. 7, 2019

(30) Foreign Application Priority Data
Feb. 15, 2016  (JP) .................................. 2016-025689

(51) Int. Cl.
| | | |
|---|---|---|
| *G01N 33/574* | (2006.01) |
| *A61K 39/395* | (2006.01) |
| *A61K 49/00* | (2006.01) |
| *A61K 49/16* | (2006.01) |
| *A61P 35/00* | (2006.01) |
| *C07K 14/705* | (2006.01) |
| *C07K 16/30* | (2006.01) |
| *C07K 16/46* | (2006.01) |
| *C12N 15/09* | (2006.01) |
| *C12N 15/62* | (2006.01) |
| *G01N 33/577* | (2006.01) |
| *G01N 33/68* | (2006.01) |

(52) U.S. Cl.
CPC ........ *G01N 33/574* (2013.01); *A61K 39/395* (2013.01); *A61K 49/00* (2013.01); *A61K 49/0058* (2013.01); *A61K 49/16* (2013.01); *A61P 35/00* (2018.01); *C07K 14/705* (2013.01); *C07K 16/30* (2013.01); *C07K 16/3092* (2013.01); *C07K 16/46* (2013.01);

*C12N 15/09* (2013.01); *C12N 15/62* (2013.01); *G01N 33/57423* (2013.01); *G01N 33/68* (2013.01)

(58) Field of Classification Search
CPC ....................................................... C07K 16/30
See application file for complete search history.

(56) References Cited

U.S. PATENT DOCUMENTS

| | | |
|---|---|---|
| 2004/0152088 A1 | 8/2004 | Fishman et al. |
| 2011/0027268 A1 | 2/2011 | Kahnert et al. |
| 2011/0034676 A1* | 2/2011 | Donohoe ............... C07K 16/44 530/387.3 |
| 2013/0059744 A1 | 3/2013 | Wandall et al. |
| 2018/0057553 A1 | 3/2018 | Imai et al. |
| 2018/0201901 A1* | 7/2018 | Duchateau ............. A61K 35/17 |
| 2019/0071517 A1 | 3/2019 | Tsuji et al. |

FOREIGN PATENT DOCUMENTS

| | | |
|---|---|---|
| CN | 101952319 A | 1/2011 |
| JP | 2004-528828 A | 9/2004 |
| JP | 6859498 B2 | 4/2021 |
| WO | WO-2009/068204 A1 | 6/2009 |
| WO | WO-2016/140344 A1 | 9/2016 |

OTHER PUBLICATIONS

Rudikoff et al. (Proceedings of the National Academy of Sciences USA, vol. 79, p. 1979-1983, 1982) (Year: 1982).*
Portolano (The Journal of Immunology, vol. 150, No. 3, p. 880-887, 1993) (Year: 1993).*
Beiboer (J. Mol. Biol. (2000) 296:833-849) (Year: 2000).*
Johnson and Wu (Methods in Molecular Biology, Antibody Engineering: Methods and Protocols, vol. 248, p. 11-25, 2004) (Year: 2004).*
Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Komenaka et al. (Clinics in Dermatology, 2004, vol. 22, p. 251-265) (Year: 2004).*
Evans et al. (Q. J. Med 1999: 92: 299-307) (Year: 1999).*
Schiffman et al. (The New England Journal of Medicine, Vo. 353, No. 20, p. 2101-2104, 2005) (Year: 2005).*

(Continued)

*Primary Examiner* — Michael Allen
(74) *Attorney, Agent, or Firm* — Clark & Elbing LLP; Susan M. Michaud

(57) ABSTRACT

The present invention provides an antibody for detecting mesothelioma and an antibody having high specificity to mesothelioma and high sensitivity thereto. The present invention also provides a method of diagnosis of mesothelioma by using the antibody, a reagent containing the antibody for use in diagnosis of mesothelioma, and a kit comprising the antibody for use in diagnosis of mesothelioma. Further, the present invention provides a marker for use in diagnosis of mesothelioma. Furthermore, the present invention provides a pharmaceutical composition containing the antibody according to the present invention or an antigen-binding fragment thereof for use in treatment of mesothelioma. An antibody that binds to a glycosylated HEG1 protein obtained from mesothelioma.

5 Claims, 9 Drawing Sheets
Specification includes a Sequence Listing.

(56) References Cited

OTHER PUBLICATIONS

Cuzick et al. (The Lancet, vol. 361, p. 296-300, 2003) (Year: 2003).*
Hernandez-Ledesma (Peptides, vol. 30, p. 426-430, 2009) (Year: 2009).*
Ludwig et al. (Nature Reviews: Cancer, vol. 5, p. 845-856, 2005) (Year: 2005).*
Pepe et al. (Journal of the National Cancer Institute, vol. 93, No. 14, p. 1054-1061, 2001) (Year: 2001).*
Mettlin et al. (Cancer, vol. 74, No. 5, p. 1615-1620, 1994) (Year: 1994).*
Brawer et al. (Urology, vol. 52, No. 3, p. 372-378, 1998) (Year: 1998).*
Budman et al. (CUAJ, vol. 2, Issue 3, p. 212-221, 2008) (Year: 2008).*
Mantovani (European Journal of Cancer, vol. 30A, No. 3, p. 363-369, 1994) (Year: 1994).*
Chang et al., "Molecular cloning of mesothelin, a differentiation antigen present on mesothelium, mesotheliomas, and ovarian cancers," Proc Natl Acad Sci USA. 93(1):136-40 (1996).
Creaney et al., "Overexpression and altered glycosylation of MUC1 in malignant mesothelioma," Br J Cancer. 98(9):1562-9 (2008).
Extended European Search Report dated Jul. 9, 2019 for European Patent Application No. 17752868.4, Tsuji et al., "Recognition of Membrane Type Mucin-Like Protein and Clinical Application Thereof," filed Jan. 16, 2017 (10 pages).
Hassan et al., "Mesothelin targeted cancer immunotherapy," Eur J Cancer. 44(1):46-53 (2008).
Matsuura et al., "Identification of mesothelioma-specific sialylated epitope recognized with monoclonal antibody SKM9-2 in a mucin-like membrane protein HEG1," Sci Rep. 8(1):14251 (2018) (13 pages).
Roulois et al., "Recognition of pleural mesothelioma by mucin-1(950-958)/human leukocyte antigen A*0201-specific CD8+ T-cells," Eur Respir J. 38(5):1117-26 (2011).
Ziegler et al., "Proteomic surfaceome analysis of mesothelioma," Lung Cancer. 75(2):189-96 (2012).
Allred et al., "Prognostic and predictive factors in breast cancer by immunohistochemical analysis," Mod Pathol. 11(2):155-68 (1998).
Hidari et al., "Detection of Sia-alpha-2-3-containing sugar chain," Wako Jun'yaku Jiho. 80(1):2-4 (2012) (12 pages including translation).
International Search Report mailed Feb. 21, 2017 for International Patent Application No. PCT/JP2017/001250, Tsuji et al., "Recognition of Membrane Type Mucin-like Protein and Clinical Application Thereof," filed Jan. 16, 2017 (6 pages including translation).
Kannagi et al., "Carbohydrate antigen in cancer cells," Kagaku to Seibutsu. 26(4):220-234 (1988) (50 pages including translation).
Melaiu et al., "Expression status of candidate genes in mesothelioma tissues and cell lines," Mutat Res. 771:6-12 (2015).
Pearson et al., "Improved tools for biological sequence comparison," Proc Natl Acad Sci U S A. 85(8):2444-8 (1988).
Tsuji et al., "HEG1 is a novel mucin-like membrane protein that serves as a diagnostic and therapeutic target for malignant mesothelioma," Sci Rep. 7:45768 (2017) (12 pages).
Tsuji et al., "Identification of novel mesothelioma marker molecules with extremely excellent specificity and sensitivity," The 36th Japan Society for Molecular Tumor Marker Research. Published: Sep. 12, 2016 (7 pages including translation).
Tsuji et al., "New clinical application of mesothelioma biomarker—intelectin," Japan Society for Molecular Tumor Marker Research Program. 35:74-75 (2015) (9 pages including translation).
Washimi et al., "Study on novel pathological diagnostic marker for malignant pleural mesothelioma," Proceedings of the Japanese Society of Pathology (Proc Japan Soc Pathol). 102(1):345 (2013) (4 pages including translation).
Chen et al., "Analysis of 5518 unique, productively rearranged human VH3-23*01 gene sequences reveals CDR-H3 length-dependent usage of the IGHD2 gene family," Protein Eng. Des. Sel. 30(9):603-609 (2017).
Office Action dated Sep. 7, 2021 for Japanese Patent Application No. 2020-135551, Tsuji et al., "Recognition of Membrane Type Mucin-like Protein and Clinical Application Thereof," filed Aug. 11, 2020 (10 pages).
Genbank, "HEG1 protein [Homo sapiens]," <https://www.ncbi.nlm.nih.gov/protein/AAH67235.1?report=genbank&log$prottop&blast_rank=57& RID=89RD5DYC013>, pri Mar. 18, 2009; retrieved on Apr. 25, 2021 (2 pages).
Gingras et al., "The structure of the ternary complex of Krev interaction trapped 1 (KRIT1) bound to both the Rap1 GTPase and the heart of glass (HEG1) cytoplasmic tail," J. Biol. Chem. 288(33):23639-23649 (2013).
Kreuk et al., "Heart of glass anchors Rasip1 at endothelial cell-cell junctions to support vascular integrity," eLife 5(e11394):1-23 (2015).
Office Action issued May 11, 2021 for Chinese Patent Application No. 201780011527.6, Tsuji et al., "Recognition of Membrane Type Mucin-like Protein and Clinical Application Thereof," filed Jan. 16, 2017 (19 pages).

* cited by examiner

- Untreated
- α2-3 Neuraminidase
- α2-3,6,8 Neuraminidase
- β-N-Acetylglucosaminidase
- N-Glycanase (PNGase F)
- Lysozyme
- Hyaluronidase
- Proteinase K — SKM9-2 antibody
— Control mAb (2D2, irrelevant mAb)

ANTIBODY BINDING TO HEG1 AND USE OF THE ANTIBODY FOR DETECTION AND TREATMENT OF MESOTHELIOMA

TECHNICAL FIELD

The present invention relates to recognition of membrane type mucin-like protein and clinical application thereof. More specifically, the present invention relates to an antibody for detecting mesothelioma and an antibody having high specificity to mesothelioma and high sensitivity thereto. The present invention also relates to a method of diagnosing mesothelioma by using the antibody, an agent comprising the antibody for use in diagnosis of mesothelioma, and a kit comprising the antibody for use in diagnosis of mesothelioma. Further, the present invention relates to a marker for use in diagnosis of mesothelioma. Furthermore, the present invention relates to a pharmaceutical composition containing the antibody according to the present invention or an antigen-binding fragment thereof for use in treatment of mesothelioma.

BACKGROUND ART

Malignant mesothelioma, a malignant tumor generated primarily because of exposure to asbestos, is a disease considered as a significant social issue. Early detection of malignant mesothelioma is difficult, and malignant mesothelioma is classified as one of malignant tumors with poor prognosis. Malignant mesothelioma may be pathologically similar to metastatic adenocarcinoma or sarcoma or reactive mesothelial cells, which are derived from benign proliferation, and differential diagnosis of them on pathological basis is often difficult. In addition, various tissue types of malignant mesothelioma are present, such as epithelial mesothelioma and sarcomatoid mesothelioma, which results in frequent difficulty in diagnosis of malignant mesothelioma. While development of an immunohistological marker for pathological diagnosis with high specificity to malignant mesothelioma has been continued in such circumstances, antibodies frequently used are not necessarily those with high specificity to malignant mesothelioma, and differential diagnosis from multiple viewpoints is generally made by using positive markers and negative markers in combination in pathological diagnosis.

Examples of a positive marker frequently used for pathological diagnosis of malignant mesothelioma include calretinin, cytokeratin 5/6 (CK5/6), mesothelin, podoplanin, and Wilms' tumor gene product-1 (WT-1). These markers allow detection of malignant epithelial mesothelioma generally at a high sensitivity (around 80 to 90%). However, these markers are not necessarily superior in specificity, and cannot be used for differential diagnosis between lung adenocarcinoma and malignant epithelial mesothelioma and detection of malignant sarcomatoid mesothelioma in some cases. An image of nuclear localization of calretinin or WT-1 in malignant mesothelioma is an important factor in differential diagnosis of malignant mesothelioma. Molecules of such markers are observed to be expressed in the cytoplasm in various healthy tissues and cancer cells, and it is required to determine whether the molecules are expressed in the nucleus or in the cytoplasm. Thus, the markers are disadvantageous in terms of visibility for markers for pathological diagnosis.

Non Patent Literature 1, in which analysis is made for genes to be expressed as mRNA in malignant mesothelioma, concludes that the increase of the mRNA level analyzed is not a statistically significant phenomenon, and fails to specify a factor available for diagnosis.

CITATION LIST

Non Patent Literature

Non Patent Literature 1: Melaiu O. et al., Mutation Research, 771: 6-12, 2015

SUMMARY OF INVENTION

The present invention provides an antibody for detecting mesothelioma and an antibody having high specificity to mesothelioma and high sensitivity thereto. The present invention also provides a method of diagnosing mesothelioma by using the antibody, an agent containing the antibody for use in diagnosis of mesothelioma, and a kit comprising the antibody for use in diagnosis of mesothelioma. Further, the present invention provides a marker for use in diagnosis of mesothelioma. Furthermore, the present invention provides a pharmaceutical composition containing the antibody according to the present invention or an antigen-binding fragment thereof for use in treatment of mesothelioma.

The present inventors found that SKM9-2 antibody obtained through immunization of a mouse with human mesothelioma cells is capable of recognizing mesothelioma with high sensitivity and high specificity. The present inventors also found that the antigen for the SKM9-2 antibody is HEG1 protein. On the basis of this result, the present inventors further found that HEG1 protein can be used as a marker for mesothelioma. The present inventors furthermore found that the SKM9-2 antibody binds to HEG1 protein in a glycosylation-dependent manner. Moreover, the present inventors found that HEG1 protein having glycosylation in mesothelioma can be also used as a marker for mesothelioma. The present invention was made on the basis of these findings.

Specifically, the present invention provides followings.

[1] An antibody that binds to HEG1 protein having glycosylation obtained from mesothelioma, or an antigen-binding fragment thereof.

[2] The antibody or the antigen-binding fragment thereof according to [1], wherein the antibody binds to the HEG1 protein having glycosylation obtained from mesothelioma in a glycosylation-dependent manner.

[2'] The antibody or the antigen-binding fragment thereof according to [1] or [2], wherein the antibody binds to both the sugar chain part and peptide part of the HEG1 protein having glycosylation obtained from mesothelioma.

[3] An antibody that binds to HEG1 protein on a cell membrane of mesothelioma.

[4] The antibody according to [3] or an antigen-binding fragment thereof, wherein the antibody is:

(1) an antibody comprising a heavy chain variable region comprising CDR1 having the amino acid sequence set forth in SEQ ID NO: 6, CDR2 having the amino acid sequence set forth in SEQ ID NO: 8, and CDR3 having the amino acid sequence set forth in SEQ ID NO: 10;

(2) an antibody comprising a light chain variable region comprising CDR1 having the amino acid sequence set forth in SEQ ID NO: 12, CDR2 having the amino acid sequence set forth in SEQ ID NO: 14, and CDR3 having the amino acid sequence set forth in SEQ ID NO: 16; (3) an antibody comprising a heavy chain variable region comprising CDR1 having the amino acid sequence set forth in SEQ ID NO: 6, CDR2 having the amino acid sequence set forth in SEQ ID NO: 8, and CDR3 having the amino acid sequence set forth in SEQ ID NO: 10, and a light chain variable region comprising CDR1 having the amino acid sequence set forth in SEQ ID NO: 12, CDR2 having the amino acid sequence set forth in SEQ ID NO: 14, and CDR3 having the amino acid sequence set forth in SEQ ID NO: 16;

(4) an antibody having amino acid sequence homology of 80% or more (e.g., 90% or more or 95% or more) to any of the antibodies (1) to (3);

(5) an antibody that competes for binding with any of the antibodies (1) to (4); or (6) an antibody that binds to the same epitope as any of the antibodies (1) to (4).

[5] An antibody that binds to a peptide having the amino acid sequence set forth in SEQ ID NO: 53, wherein the peptide is expressed in a mesothelioma cell line.

[6] The antibody or the antigen-binding fragment thereof according to [4], wherein the antigen is HEG1 protein having glycosylation obtained from mesothelioma.

[7] A protein complex comprising: a fusion protein of a $V_H$ region or a $V_H$ region and CH1 region of the antibody according to any one of [1] to [6] with human intelectin protein; and a light chain of the antibody.

[8] An agent for use in diagnosis of mesothelioma, comprising an antibody that binds to HEG1 protein, the antibody according to any one of [1] to [6] or an antigen-binding fragment thereof, or the protein complex according to [7].

[9] An agent for use in in vivo diagnosis of mesothelioma, comprising a conjugate of an antibody that binds to HEG1 protein, the antibody according to any one of [1] to [6] or an antigen-binding fragment thereof, or the protein complex according to [7], with an imaging probe.

[10] A kit for use in diagnosis of mesothelioma, comprising an antibody that binds to HEG1 protein, the antibody according to any one of [1] to [6] or an antigen-binding fragment thereof, or the protein complex according to [7].

[11] A kit for use in in vivo diagnosis of mesothelioma, comprising a conjugate of an antibody that binds to HEG1 protein, the antibody according to any one of [1] to [6] or an antigen-binding fragment thereof, or the protein complex according to [7], with an imaging probe.

[12] A pharmaceutical composition for use in treatment of mesothelioma, comprising an antibody that binds to HEG1 protein, the antibody according to any one of [1] to [6] or an antigen-binding fragment thereof, or the protein complex according to [7].

[13] A pharmaceutical composition for use in treatment of mesothelioma, comprising an expression suppressing agent for HEG1.

[14] A method of detecting mesothelioma, comprising detecting HEG1 protein in a sample separated from a living body.

[15] A method of detecting mesothelioma, comprising detecting HEG1 protein in a sample separated from a living body by using an antibody that binds to HEG1 protein, the antibody according to any one of [1] to [6] or an antigen-binding fragment thereof, or the protein complex according to [7].

[16] HEG1 protein having glycosylation obtained from mesothelioma or a fragment thereof comprising an amino acid sequence from position 799 to position 809 of the amino acid sequence set forth in SEQ ID NO: 35.

[16'] HEG1 protein having O-glycosylation obtained from mesothelioma or a fragment thereof comprising an amino acid sequence from position 799 to position 809 of the amino acid sequence set forth in SEQ ID NO: 35.

[17] A marker for use in diagnosis of mesothelioma, containing the HEG1 protein or the fragment thereof according to [16].

[17'] A marker for use in diagnosis of mesothelioma, containing the HEG1 protein defined or the fragment thereof according to [16'].

BRIEF DESCRIPTION OF DRAWINGS

FIG. 1A shows an immunohistological staining image of epithelial mesothelioma and FIG. 1B shows an immunohistological staining image of sarcomatoid mesothelioma, and arrowheads each indicate a stained portion.

| SEQ ID NO | Name | |
|---|---|---|
| 66 | 7.6 | DLKSQSTPHQEKVITESKSPSLVSLP TESTKAVTTNSPLPPSLTESSTE |

| SEQ ID NO | Name | |
|---|---|---|
| 67 | 7.61 | DLKSQSTPHQEKVITESKSP |
| 68 | 7.62 | EKVITESKSPSLVSLPTEST |
| 69 | 7.63 | SLVSLPTESTKAVTTNSPLP |
| 70 | 7.64 | KAVTTNSPLPPSLTESSTE |
| 71 | 7.623 | SKSPSLVSLPTEST |
| 72 | | GGSKSPSLVSLPTEGG |
| 88 | 7.6231 | SKSPSLVSLPTE |
| 73 | 7.6232 | KSPSLVSLPTE |
| 74 | 7.6241 | SPSLVSLPTE |
| 75 | 7.6242 | PSLVSLPTE |
| 76 | S799A | AKSPSLVSLPTE |
| 77 | K800A | SASPSLVSLPTE |
| 78 | S801A | SKAPSLVSLPTE |
| 79 | P802A | SKSASLVSLPTE |
| 80 | S803A | SKSPALVSLPTE |
| 81 | L804A | SKSPSAVSLPTE |
| 82 | V805A | SKSPSLASLPTE |
| 83 | S806A | SKSPSLVALPTE |
| 84 | L807A | SKSPSLVSAPTE |
| 85 | P808A | SKSPSLVSLATE |
| 86 | T809A | SKSPSLVSLPAE |
| 87 | E810A | SKSPSLVSLPTA |
| 89 | | SKSPSLVSLPT |

Figure 14A:
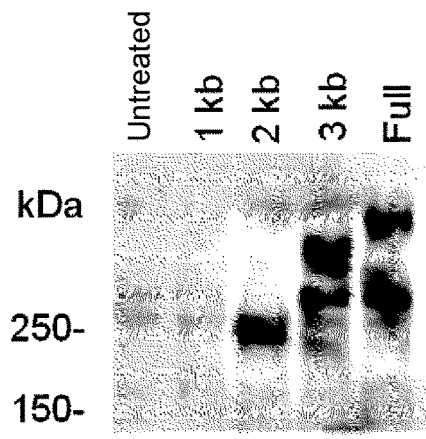

FIG. 14A shows results of Western blot to examine the reactivity of each of HEG1 full length, fragment 3 kb, fragment 2 kb, and fragment 1 kb with SKM9-2 antibody.

Figure 14B:
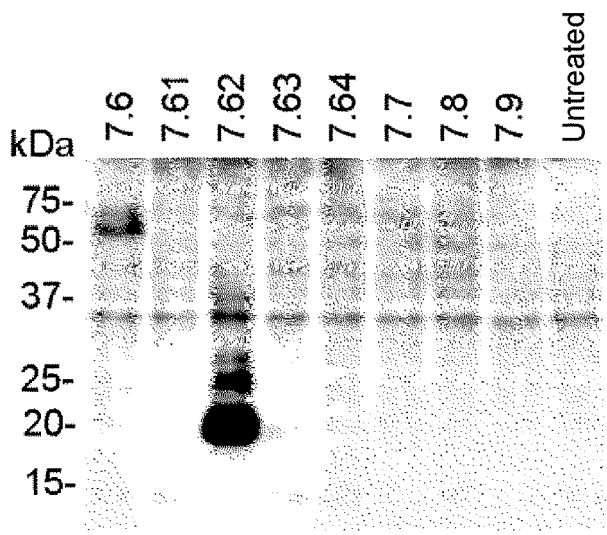

FIG. 14B shows results of Western blot to examine the reactivity of each HEG1 fragment with SKM9-2 antibody, where a positive signal was found for fragment 7.6 and fragment 7.62.

Figure 14C:
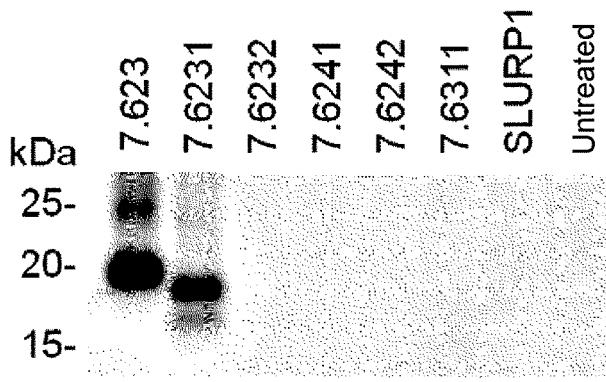

FIG. 14C shows results of Western blot to examine the reactivity of each HEG1 fragment with SKM9-2 antibody, where a positive signal was found for fragment 7.623 and fragment 7.6231.

Figure 14D:
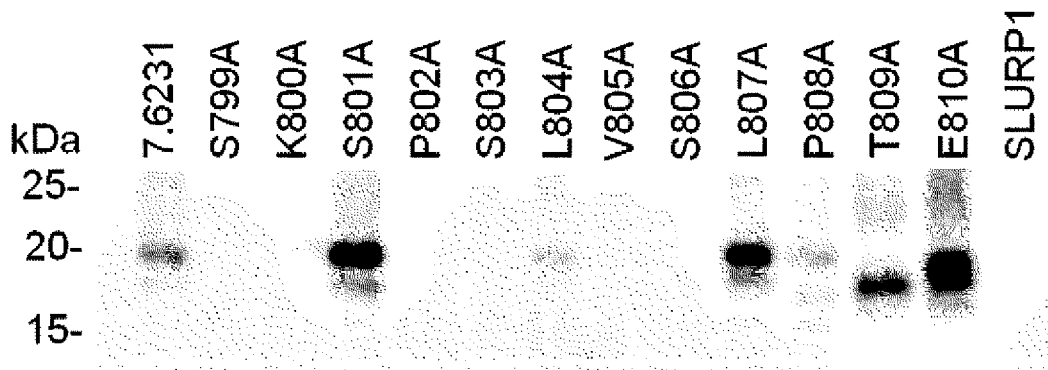

FIG. 14D shows results of alanine scanning, where S799A indicates a fragment having the amino acid sequence set forth in SEQ ID NO: 35 with serine at position 799 as an amino acid number substituted with alanine.

Figure 14E:

FIG. 14E shows that fragment 7.6231 treated with neuraminidase does not react with SKM9-2 antibody.

DESCRIPTION OF EMBODIMENT

The term "subject" in the present specification may refer to a mammal, and preferably refers to a human. The subject may be a subject affected with or possibly affected with mesothelioma or another tumor or carcinoma.

The term "antibody" in the present specification refers to an immunoglobulin, and encompasses polyclonal antibodies and monoclonal antibodies. Preferred antibody is monoclonal antibodies. The origin of the antibody is not limited, and examples of the antibody include antibodies derived from non-human animals, antibodies derived from non-human mammals, and human antibodies. The antibody may be any of chimeric antibodies, humanized antibodies, and human antibodies. In addition, the antibody may be any of bispecific antibodies.

The term "antigen-binding fragment" in the present specification refers to a part of an antibody with the binding properties to the antigen retained. The antigen-binding fragment can comprise a heavy chain variable region or light chain variable region of the antibody according to the present invention, or both of them. The antigen-binding fragment may be chimerized or humanized. Examples of the antigen-binding fragment include an Fab, Fab', F(ab')$_2$, Fv, scFv (single-chain Fv), diabody, and sc(Fv)$_2$ (single-chain (Fv)$_2$). Each of these antibody fragments can be obtained, for example, through enzymatic treatment of an antibody, though the method is not limited thereto. For example, digestion of an antibody with papain gives Fabs. On the other hand, digestion of an antibody with pepsin gives an F(ab')$_2$, which is further reduced to give Fab's. These antigen-binding fragments of an antibody can be used in the present invention.

The term "mesothelioma" in the present specification refers to a tumor derived from mesothelial cells. Mesothelioma is classified by the site of development, and known examples are pleural mesothelioma, peritoneal mesothelioma, pericardial mesothelioma, and mesothelioma of the tunica vaginalis. In the present specification, the term "mesothelioma" refers to benign mesothelioma and/or malignant mesothelioma. Mesothelioma is broadly classified by the tissue type into epithelial mesothelioma, sarcomatoid mesothelioma, biphasic mesothelioma, and other mesotheliomas (e.g., desmoplastic mesothelioma).

HEG1 protein is a protein whose expression and function are almost unknown, and inferred to be a membrane protein from gene ontology analysis. Examples of human HEG1 protein include a protein (SEQ ID NO: 30) encoded by a gene registered by the National Center for Biotechnology Information (NCBI) as NM_020733.1 and having the sequence set forth in SEQ ID NO: 29; a protein having the amino acid sequence set forth in SEQ ID NO: 31; a protein (SEQ ID NO: 37) encoded by a gene registered as XM_005247666 and having the sequence set forth in SEQ ID NO: 36; a protein (SEQ ID NO: 33) encoded by a gene having the sequence set forth in SEQ ID NO: 32; and a protein (SEQ ID NO: 35) encoded by a gene having the sequence set forth in SEQ ID NO: 34. Examples of naturally occurring variants of HEG1 protein include, but are not limited to, a variant of HEG1 protein having an amino acid sequence having a mutation corresponding to any of Q145R, S305P, F602S, V980L, and M1039T in the amino acid sequence set forth in SEQ ID NO: 30. In the present specification, the concept of HEG1 protein includes naturally occurring variants of HEG1 protein. In the case of human HEG1 protein, the serine at position 1359 of the amino acid sequence set forth in SEQ ID NO: 30 may be replaced with phosphoserine. The concept of HEG1 protein in the present specification includes HEG1 protein in which the serine corresponding to the serine at position 1359 of the amino acid sequence set forth in SEQ ID NO: 30 is replaced with phosphoserine. It is expected from results of gene ontology analysis that, in HEG1 protein, the signal peptide part is a domain corresponding to position 1 to position 29 of the amino acid sequence set forth in SEQ ID NO: 30, the extracellular domain is a domain corresponding to position 30 to position 1248 of the amino acid sequence set forth in SEQ ID NO: 30, the transmembrane domain is a domain corresponding to position 1249 to position 1269 of the amino acid sequence set forth in SEQ ID NO: 30, and the intracellular domain is a domain corresponding to position 1270 to position 1381 of the amino acid sequence set forth in SEQ ID NO: 30. The concept of HEG1 protein can include, for example, a protein encoded by a DNA sequence set forth in SEQ ID NO: 29, 32, 34, or 36 or a DNA sequence hybridizable under stringent conditions with a complementary strand of a DNA having a DNA sequence encoding the amino acid sequence set forth in SEQ ID NO: 30, 31, 33, 35, or 37. Examples of stringent conditions include conditions such that washing is performed with 1×SSC (aqueous solution containing 0.15 M NaCl and 15 mM trisodium citrate) at 65° C. after hybridization. In addition, the concept of HEG1 protein can include a protein having the amino acid sequence having homology with the amino acid sequence set forth in SEQ ID NO: 30 of 90% or more, 95% or more, 98% or more, or 99% or more. For example, HEG1 protein may have substitution, insertion, addition, and/or deletion of one or more amino acids in the amino acid sequence set forth in SEQ ID NO: 30.

The present inventors found that HEG1 protein is expressed primarily in mesothelioma. The present inventors contend that mesothelioma can be diagnosed on the basis of the expression level of HEG1 protein. Accordingly, the present invention enables detection of mesothelioma by using an antibody that binds to HEG1 protein. According to the present invention, HEG1 protein is expressed on the cell membrane surface of mesothelioma, and includes an extracellular domain. In view of this, the antibody according to the present invention binds to the cell membrane of mesothelioma, a membrane protein on the cell membrane of mesothelioma, or HEG1 protein on the cell membrane of mesothelioma. The antibody according to the present invention may be an antibody against the extracellular domain of HEG1 protein or an antigen-binding fragment thereof. According to the present invention, HEG1 protein is also expressed in well-differentiated papillary mesothelioma (WDPM), and thus may be used for detecting such mesothelioma.

As described later in Examples, the extracellular domain of HEG1 protein has been subjected to glycosylation having sialylation in mesothelioma. Accordingly, the antibody according to the present invention or an antigen-binding fragment thereof binds to HEG1 protein having glycosylation in a certain embodiment. When the HEG1 protein having glycosylation is purified and analyzed through SDS-PAGE, an apparent molecular weight in the range of 300 kDa to 500 kDa can be detected as a broad band. More specifically, the apparent molecular weight by SDS-PAGE may be approximately 400 kDa. In a certain embodiment of the present invention, the glycosylation is the one which HEG1 protein expressed on the cell membrane of mesothelioma has.

In a certain embodiment, the antibody according to the present invention or an antigen-binding fragment thereof binds to HEG1 protein having glycosylation found in mesothelioma cells, and the binding is glycosylation-dependent. Specifically, in this embodiment, the antibody according to the present invention or an antigen-binding fragment thereof does not bind to unglycosylated HEG1 protein (e.g., HEG1 protein, the sugar chain of which has been decomposed through sugar chain decomposition treatment), or more weakly binds thereto than to HEG1 protein having glycosylation (lower affinity). In a certain embodiment, the antibody according to the present invention or an antigen-binding fragment thereof binds to the sugar chain part of HEG1 protein having glycosylation found in mesothelioma cells. Thus, the antibody according to the present invention can bind to HEG1 protein having glycosylation in a glycosylation-dependent manner in certain embodiments, and the glycosylation may be the one which HEG1 protein present on the cell membrane of mesothelioma has. In a certain embodiment, the antibody according to the present invention binds to HEG1 protein having glycosylation found in denatured mesothelioma cells. In a certain embodiment, the antibody according to the present invention binds to a denatured fragment of HEG1 protein having glycosylation found in mesothelioma cells, wherein the fragment has an amino acid sequence comprising the amino acid sequence from position 799 to position 809 of the amino acid sequence set forth in SEQ ID NO: 35.

In a certain embodiment, the antibody according to the present invention or an antigen-binding fragment thereof is an antibody or antigen-binding fragment thereof which binds to an epitope on the extracellular domain of human HEG1 protein expressed in human mesothelioma cells, but undergoes weakening in or loss of binding to human HEG1 protein through treatment with α2-3 neuraminidase or α2-3, 6,8 neuraminidase. In this embodiment, the extracellular domain of human HEG1 protein expressed in human mesothelioma cells has glycosylation having sialylation. The term "HEG1 protein having glycosylation obtained from mesothelioma" can refer to HEG1 protein having glycosylation characteristic to mesothelioma, and the glycosylation can be, for example, O-glycosylation having sialylation.

In a certain embodiment, an antibody that binds to the cell membrane of mesothelioma, a membrane protein on the cell membrane of mesothelioma, or HEG1 protein on the cell membrane of mesothelioma is provided, wherein the antibody comprises any one, two, three, four, five, or six of heavy chain CDR1 having the amino acid sequence set forth in SEQ ID NO: 6, heavy chain CDR2 having the amino acid sequence set forth in SEQ ID NO: 8, heavy chain CDR3 having the amino acid sequence set forth in SEQ ID NO: 10, light chain CDR1 having the amino acid sequence set forth in SEQ ID NO: 12, light chain CDR2 having the amino acid sequence set forth in SEQ ID NO: 14, and light chain CDR3 having the amino acid sequence set forth in SEQ ID NO: 16. In a certain embodiment, an antibody is provided, wherein the antibody comprises a heavy chain variable region comprising any one, two, or three of heavy chain CDR1 having the amino acid sequence set forth in SEQ ID NO: 6, heavy chain CDR2 having the amino acid sequence set forth in SEQ ID NO: 8, and heavy chain CDR3 having the amino acid sequence set forth in SEQ ID NO: 10, and a light chain variable region comprising any one, two, or three of light chain CDR1 having the amino acid sequence set forth in SEQ ID NO: 12, light chain CDR2 having the amino acid sequence set forth in SEQ ID NO: 14, and light chain CDR3 having the amino acid sequence set forth in SEQ ID NO: 16.

In a certain embodiment, an antibody that binds to the cell membrane of mesothelioma, a membrane protein on the cell membrane of mesothelioma, or HEG1 protein on the cell membrane of mesothelioma, or an antigen-binding fragment thereof is provided, wherein the antibody is:

(1) an antibody comprising a heavy chain variable region comprising CDR1 having the amino acid sequence set forth in SEQ ID NO: 6, CDR2 having the amino acid sequence set forth in SEQ ID NO: 8, and CDR3 having the amino acid sequence set forth in SEQ ID NO: 10;

(2) an antibody comprising a light chain variable region comprising CDR1 having the amino acid sequence set forth in SEQ ID NO: 12, CDR2 having the amino acid sequence set forth in SEQ ID NO: 14, and CDR3 having the amino acid sequence set forth in SEQ ID NO: 16;

(3) an antibody comprising a heavy chain variable region comprising CDR1 having the amino acid sequence set forth in SEQ ID NO: 6, CDR2 having the amino acid sequence set forth in SEQ ID NO: 8, and CDR3 having the amino acid sequence set forth in SEQ ID NO: 10, and a light chain variable region comprising CDR1 having the amino acid sequence set forth in SEQ ID NO: 12, CDR2 having the amino acid sequence set forth in SEQ ID NO: 14, and CDR3 having the amino acid sequence set forth in SEQ ID NO: 16;

(4) an antibody having sequence homology of 80% or more (e.g., 90% or more or 95% or more) to any of the antibodies (1) to (3);

(5) an antibody that competes for binding with any of the antibodies (1) to (4); or (6) an antibody that binds to an epitope for any of the antibodies (1) to (4).

In a certain embodiment, the antibody according to the present invention is an antibody that binds to a peptide having the sequence set forth in SEQ ID NO: 53. In a certain embodiment, the antibody according to the present invention is an antibody that binds to a peptide having the sequence set forth in SEQ ID NO: 53 expressed in a mesothelioma cell line. In a certain embodiment, the antibody according to the present invention is an antibody that binds to a peptide having a sequence set forth in SEQ ID NO: 53 in a glycosylation-dependent manner, wherein the peptide is expressed in a mesothelioma cell line. In a certain embodiment, the antibody according to the present invention is an antibody that binds to the cell membrane of mesothelioma, a membrane protein on the cell membrane of mesothelioma, or HEG1 protein on the cell membrane of mesothelioma, and binds to a peptide having the sequence set forth in SEQ ID NO: 53. In a certain embodiment, the antibody according to the present invention is an antibody that binds to the cell membrane of mesothelioma, a membrane protein on the cell membrane of mesothelioma, or HEG1 protein on the cell membrane of mesothelioma, and binds to a peptide having the sequence set forth in SEQ ID NO: 53, wherein the peptide is expressed in a mesothelioma cell line. In a certain embodiment, the antibody according to the present invention is an antibody that binds to the cell membrane of mesothelioma, a membrane protein on the cell membrane of mesothelioma, or HEG1 protein on the cell membrane of mesothelioma, and binds to a peptide having the sequence set forth in SEQ ID NO: 53 in a glycosylation-dependent manner, wherein the peptide is expressed in a mesothelioma cell line.

Sequence homology can be determined, for example, by using a FASTA program described in Pearson and Lipman, PNAS, 85:2444-2448, 1988, with default parameters.

In a certain embodiment, the antibody according to the present invention comprises a heavy chain having the amino acid sequence set forth in SEQ ID NO: 2. In a certain embodiment, the antibody according to the present invention comprises a light chain having the amino acid sequence set forth in SEQ ID NO: 4. In a certain embodiment, the antibody according to the present invention comprises the heavy chain having the amino acid sequence set forth in SEQ ID NO: 2 and the light chain having the amino acid sequence set forth in SEQ ID NO: 4. In a certain embodiment, the antibody according to the present invention comprises position 20 to position 132 of the amino acid sequence set forth in SEQ ID NO: 2 as a heavy chain variable region ($V_H$ region). In a certain embodiment, the antibody according to the present invention comprises position 20 to position 132 of the amino acid sequence set forth in SEQ ID NO: 4 as a light chain variable region ($V_L$ region). In a certain embodiment, the antibody according to the present invention comprises a heavy chain variable region comprising position 20 to position 132 of the amino acid sequence set forth in SEQ ID NO: 2 and a light chain variable region comprising position 20 to position 132 of the amino acid sequence set forth in SEQ ID NO: 4. In a certain embodiment, the antibody according to the present invention competes with any of the antibodies for binding to HEG1 protein having glycosylation.

The present invention also provides a chimeric antigen receptor comprising a heavy chain variable region and a light chain variable region, such as an scFv. Various chimeric antigen receptors can be used, and examples thereof include first generation chimeric antigen receptors in which an scFv and a T-cell receptor ξ-chain are linked together via a spacer, second generation chimeric antigen receptors in which an scFv and a T-cell receptor ξ-chain are linked together via a CD28 or a 4-11BB, and third generation chimeric antigen receptors in which an scFv and a T-cell receptor ξ-chain are linked together via a CD28 and a 4-1BB or OX40.

In a certain embodiment of the present invention, a conjugate of the antibody according to the present invention or an antigen-binding fragment thereof with a cytotoxic agent is provided. The present invention provides a pharmaceutical composition for use in treatment of mesothelioma, containing a conjugate of the antibody according to the present invention or an antigen-binding fragment thereof with an imaging probe. Examples of the cytotoxic agent used in the present invention include radioisotopes for cancer therapy (e.g., $P^{32}$, $Y^{90}$, $I^{131}$, $I^{125}$, $Sm^{153}$, $Re^{186}$, $Re^{188}$, $At^{211}$, $Bi^{212}$, $Pb^{212}$, and radioisotopes of Lu). Examples of the cytotoxic agent used in the present invention include anticancer agents.

In a certain embodiment of the present invention, a pharmaceutical composition for use in treatment of mesothelioma is provided, containing an siRNA, shRNA, or antisense oligonucleotide for a HEG1 gene. The siRNA, shRNA, or antisense oligonucleotide may be a modified nucleic acid. Examples of the modified nucleic acid include nucleic acids modified with a fluorescent dye, biotinylated nucleic acids, and nucleic acids comprising a cholesteryl group introduced thereto. To enhance the stability of an RNA, the bases are subjected to 2'-O-methyl modification or 2'-fluoro modification or 2'-methoxyethyl (MOE) modification in some cases, and a phosphodiester bond in the nucleic acid backbone is replaced with a phosphorothioate bond in other cases. Examples of an artificial nucleic acid include a locked nucleic acid (LNA), which is a crosslinked DNA in which an oxygen atom at position 2' and a carbon atom at position 4' are crosslinked via methylene, and a peptide nucleic acid (PNA), in which the main chain is a polymer including N-(2-aminoethyl)glycine units, in place of deoxyribose or ribose units, linked via amido bonds. The siRNA, shRNA, or antisense oligonucleotide may be incorporated in vesicles such as micelles and liposomes. Vesicle such as micelles and liposomes, for example, having a particle diameter of 20 to 100 nm can be used. Vesicles such as micelles and liposomes are known to be capable of efficiently accumulating in a tumor tissue by virtue of the EPR effect (Enhanced permeability and retention effect) to deliver the content to the tumor tissue. Such vesicles may be modified with a surface modifier such as polyethylene glycol. In a certain embodiment of the present invention, use of an siRNA, shRNA, or antisense oligonucleotide for a HEG1 gene in manufacture of a pharmaceutical composition for use in treatment of mesothelioma is provided. Further, in a certain embodiment of the present invention, a method of treating mesothelioma is provided, comprising lowering expression of HEG1 protein in a subject in need of treating mesothelioma. In a certain embodiment of the present invention, a method of treating mesothelioma is provided, comprising administering an expression suppressing agent (e.g., an siRNA, shRNA, or antisense oligonucleotide) for HEG1 gene to a subject in need of treating mesothelioma.

In a certain embodiment of the present invention, the antibody according to the present invention may have cytotoxicity activity such as antibody-dependent cell-mediated cytotoxicity activity (ADCC activity) and complement-dependent cytotoxicity activity (CDC activity). In this case, the antibody according to the present invention can exhibit cytotoxicity activity to mesothelioma cells through binding to HEG1 protein expressed on the membrane surface of mesothelioma. Thus, in a certain embodiment, a pharmaceutical composition for use in treatment of mesothelioma or agent for use in therapy of mesothelioma is provided, containing the antibody according to the present invention or an antigen-binding fragment thereof as an active ingredient. The term "treat" used in the present specification has a meaning including therapeutic treatment.

The pharmaceutical composition or agent containing the antibody according to the present invention as an active ingredient can be formulated by using a known pharmaceutical method. For example, the pharmaceutical composition or agent according to the present invention may contain a pharmaceutically acceptable excipient. The excipient can be the one which can be appropriately administered to provide a subject with an effective amount of the antibody according to the present invention as an active ingredient. In a certain embodiment, the pharmaceutical composition or agent according to the present invention can be formulated into an injection, and the excipient for the injection can be an aseptic aqueous solution, for example, an isotonic solution containing a pharmaceutically acceptable buffer such as Ringer's solution, Hanks' solution, and physiological saline, glucose, and an additional adjuvant. Examples of the adjuvant include alcohols such as ethanol, polyalcohols such as polyethylene glycol, and nonionic surfactants such as Polysorbate 80, and these adjuvants can be added in formulation. Sesame oil, coconut oil, and soybean oil can be used as an oily liquid for the injection, and benzyl benzoate or benzyl alcohol can be used as the adjuvant. The pharmaceutical composition or agent according to the present invention can be parenterally administered (e.g., intravenously administered or intrathoracically administered) in a form of an injection.

The ADCC activity or CDC activity of an antibody can be measured by using a method well known to those skilled in the art. To determine the ADCC activity, for example, mesothelioma cells and effector cells expressing an Fc receptor (e.g., NK cells or monocytes) are incubated in the presence of the antibody according to the present invention under physiological conditions, and the number of the viable cells and/or dead cells of the mesothelioma cells are counted. To determine the CDC activity, for example, mesothelioma cells are incubated with a solution containing complements (e.g., human serum) in the presence of an antibody under physiological conditions, and the number of the viable cells and/or dead cells of the mesothelioma cells are counted.

The cytotoxicity activity can be enhanced by using any of various methods well known to those skilled in the art. A known example of such methods is a method of enhancing binding between an Fc receptor of an effector cell and an antibody with use of an antibody in which fucose as a sugar chain in the Fc region is deleted, an antibody in which bisecting N-acetylglucosamine (GlcNAc) is bound to a sugar chain, or amino acid substitution in the Fc region to thereby enhance the cytotoxicity activity, and any of such modified antibodies can be used as the antibody according to the present invention.

An antibody can be converted into a genetically-modified antibody, for example, a chimeric antibody, a humanized antibody, or a human antibody by using a method well known to those skilled in the art, for example, for the purpose of lowering the antigenicity of the antibody itself in a human. In the pharmaceutical composition or agent according to the present invention, the antibody according to the present invention may be a chimeric antibody, a humanized antibody, or a human antibody. The antibody may be a bispecific antibody.

In a certain embodiment of the present invention, a conjugate of the antibody according to the present invention or an antigen-binding fragment thereof with an imaging probe is provided. According to the present invention, the conjugate of the antibody according to the present invention or an antigen-binding fragment thereof with an imaging probe can be used for in vitro diagnosis or in vivo diagnosis of mesothelioma. Accordingly, the present invention provides an agent or kit for use in diagnosis of mesothelioma, comprising a conjugate of the antibody according to the present invention or an antigen-binding fragment thereof with an imaging probe. Further, the present invention provides an agent or kit for use in in vivo diagnosis of mesothelioma, comprising a conjugate of the antibody according to the present invention or an antigen-binding fragment thereof with an imaging probe. Examples of the imaging probe available for in vivo diagnosis of mesothelioma include fluorescent imaging probes, enhancers such as contrast agents for magnetic resonance imaging (MRI) (e.g., paramagnetic ions), and radionuclides for imaging such as PET molecular imaging probes.

The present invention provides, in another aspect, HEG1 protein having a glycosylation (e.g., O-glycosylation) obtained from mesothelioma or a fragment thereof (in particular, a fragment thereof comprising the amino acid sequence from position 799 to position 809 of the amino acid sequence set forth in SEQ ID NO: 35). According to the present invention, HEG1 protein having glycosylation (e.g., O-glycosylation) obtained from mesothelioma or the fragment thereof can be used as a marker for detecting mesothelioma with high sensitivity and high specificity. Accordingly, in a certain embodiment of the present invention, a marker for use in diagnosis of mesothelioma is provided, consisting of HEG1 protein having glycosylation (e.g., O-glycosylation) obtained from mesothelioma or the fragment thereof. The O-glycosylation of HEG1 protein obtained from mesothelioma or the fragment thereof may be O-glycosylation having sialylation. Such HEG1 protein may be HEG1 protein obtained from mesothelioma and having an amino acid sequence with sequence homology of 80% or more, 90% or more, 95% or more, or 98% or more, for example, to any one amino acid sequence selected from SEQ ID NOs: 30, 31, 33, 35, and 37, or a variant thereof obtained from mesothelioma. The HEG1 protein having glycosylation (e.g., O-glycosylation) obtained from mesothelioma or the fragment thereof can be purified from mesothelioma cells by using the antibody according to the present invention (the antibody according to the present invention that binds to HEG1 protein having glycosylation (e.g., O-glycosylation) obtained from mesothelioma). Since HEG1 protein or the fragment thereof has sialic acid and GlcNAc, it is also contemplated to purify HEG1 protein by utilizing the affinity of HEG1 protein to lectins, which are capable of specifically binding to sialic acid or GlcNAc, (e.g., WGA, which is specific to sialic acid, or DSA, which is specific to GlcNAc, or combination thereof). The HEG1 protein having glycosylation (e.g., O-glycosylation) obtained from mesothelioma or the fragment thereof (in particular, a fragment thereof comprising the amino acid sequence from position 799 to position 809 of the amino acid sequence set forth in SEQ ID NO: 35) may be denatured. The fragment (in particular, the fragment denatured) may comprise a region around the amino acid sequence from position 799 to position 809 of the amino acid sequence set forth in SEQ ID NO: 35 in the HEG1 protein having glycosylation (e.g., O-glycosylation) obtained from mesothelioma.

Intelectin Fusion Protein and Complex

The present invention provides a fusion protein of intelectin with a Fab fragment or scFv fragment of the antibody according to the present invention. In this fusion protein, for example, the heavy chain of the Fab fragment or the scFv fragment and intelectin are fused together. Provided is, for example, a complex comprising: a fusion protein of intelectin with a $V_H$ region and linker (e.g., a CH1 region) of the antibody according to the present invention; and an L chain of the antibody according to the present invention. Such a fusion protein or protein complex binds to the cell membrane of mesothelioma, a membrane protein on the cell membrane, or HEG1 protein on the cell membrane. The present invention also provides a fusion protein of the scFv fragment of the antibody according to the present invention with intelectin. Such a fusion protein or protein complex comprises intelectin, and the intelectin specifically and strongly binds to diol structure. For this reason, the fusion protein or protein complex can be purified in a simple manner by using a column with a resin having exposed diol structure (e.g., a gel filtration column using, for example, a gel containing a polysaccharide (dextran or agarose) treated with an epoxide crosslinking agent or a silica gel hydrophilized through diol modification). For example, the fusion protein or protein complex can be purified by using a column with diol SEPHAROSE® (crosslinked, beaded-form of agarose) beads shown in Table 5. After purification of the complex, the fusion protein may be further produced by using an affinity column having an antigen linked thereto.

In a certain embodiment of the present invention,
(1) a fusion protein of a heavy chain variable region comprising CDR1 having the amino acid sequence set forth in SEQ ID NO: 6, CDR2 having the amino acid sequence set forth in SEQ ID NO: 8, and CDR3 having the amino acid sequence set forth in SEQ ID NO: 10, with intelectin, or
(2) a protein complex comprising the fusion protein described in (1) and a light chain variable region comprising CDR1 having the amino acid sequence set forth in SEQ ID NO: 12, CDR2 having the amino acid sequence set forth in SEQ ID NO: 14, and CDR3 having the amino acid sequence set forth in SEQ ID NO: 16 is provided. The protein complex binds to the cell membrane of mesothelioma, a membrane protein on the cell membrane of mesothelioma, or HEG1 protein on the cell membrane of mesothelioma. In this embodiment, for example, the heavy chain variable region and intelectin can form a fusion protein via the CH1 region or without intervention of the CH1 region, and preferably the heavy chain variable region and intelectin can form a fusion protein via the CH1 region. Molecules of this fusion protein can bind together via the intelectin portion of each molecule to form a multimer (primarily, a trimer) under physiological conditions. In the present specification, the concept of the fusion protein includes monomers and multimers.

The intelectin fusion protein or complex according to the present invention can bind to HEG1 protein having glycosylation obtained from mesothelioma. Accordingly, the intelectin fusion protein or complex according to the present invention can be used for detecting mesothelioma. Thus, the present invention provides an agent for use in diagnosis of mesothelioma, containing the intelectin fusion protein or complex according to the present invention. A conjugate of the intelectin fusion protein or complex according to the present invention with an imaging probe can be used for in vivo imaging of mesothelioma. Thus, the present invention provides an agent for use in in vivo diagnosis of mesothelioma, comprising a conjugate of the intelectin fusion protein or complex according to the present invention with an imaging probe. A conjugate of the intelectin fusion protein or complex according to the present invention with the cytotoxic agent defined above can be used for treatment of mesothelioma. Thus, the present invention provides a pharmaceutical composition for use in treatment of mesothelioma, containing a conjugate of the intelectin fusion protein or complex according to the present invention with the cytotoxic agent defined above.

Preparation of Antibody

An antibody can be prepared by using a method well known to those skilled in the art. Specifically, a polyclonal antibody can be obtained through immunization of an animal with an antigen and an adjuvant and collection of the plasma of the immunized animal. Alternatively, the following procedure may be employed to obtain a hybridoma producing an antibody desired: an animal is immunized with an antigen and an adjuvant; a B lymphocyte is obtained from the immunized animal; and the B lymphocyte is subjected to cell fusion with a myeloma to form a hybridoma, which may further be cloned. In the immunization process, an animal may be immunized with cells obtained by allowing a mesothelioma cell line (e.g., ACC-MESO4 cells) to forcibly express HEG1 protein. In this case, the immunized animal can produce an antibody against HEG1 protein because HEG1 protein is exposed on the cell surface. Alternatively, an animal may be immunized with HEG1 protein purified from cells expressing HEG1 protein, preferably from a mesothelioma cell line. In the immunization process, alternatively, the following procedure may be employed: a mesothelioma cell line (e.g., ACC-MESO4 cells) is allowed to forcibly express a solubilized form of HEG1 protein (e.g., the extracellular domain); the solubilized HEG1 protein is obtained from the culture supernatant; and an animal is immunized with the solubilized HEG1 protein. According to the present invention, also such solubilized HEG1 protein has glycosylation, and the glycosylation is similar to modification of HEG1 protein on the cell membrane of mesothelioma.

A chimeric antibody can be prepared by using a method well known in the art. For example, a chimeric antibody can be prepared through substitution of the constant regions of an antibody with the constant regions of a human antibody. A humanized antibody comprises, for example, complementarity-determining regions (CDRs) derived from a non-human animal and framework regions derived from a human antibody and constant regions derived from a human antibody. A humanized antibody can be obtained, for example, through transplantation of the CDRs to a human antibody. A human antibody can be obtained, for example, through immunization of a genetically-modified mouse producing a human antibody with an antigen. A bispecific antibody is an antibody capable of binding to two different epitopes or antigens, and can be prepared by using a method well known to those skilled in the art. A bispecific antibody can be prepared, for example, by using a method of further fusing cells producing two different antibodies to prepare a hybrid hybridoma, or a method in which a $V_H$ region and a $V_L$ region are expressed on one polypeptide chain via a short linker which does not allow pairing between the two regions, and the polypeptide chain is allowed to form a complex with another polypeptide chain comprising a complementary $V_H$ region and $V_L$ region capable of pairing with the above $V_H$ region and $V_L$ region.

An antibody that competes with a certain antibody for binding to an antigen can be obtained, for example, through a competition assay well known to those skilled in the art. For example, in a competition assay, if an antibody can block at least 20%, preferably 20 to 50%, more preferably at least 50% of binding of an antibody of interest, then the antibody can be determined as an antibody that competes for binding to the same antigen. The competing antibody can be confirmed through a cross-blocking assay, preferably through a competitive ELISA. In a cross-blocking assay, for example, a microtiter plate is coated with an antigen, and an entity of a candidate competing antibody is added thereto and incubated to form binding between the antigen and the candidate antibody. Thereafter, an antibody of interest is labeled, and additionally added to the well and incubated, and the well is washed and the binding rate of the antibody of interest is quantified. Thereby, the presence or absence of the competition of the antibodies can be determined. If there is any competition, a smaller amount of the label will remain in the well.

The present invention provides, in another aspect, a method of diagnosis of mesothelioma in a patient having mesothelioma or a subject at a risk of having mesothelioma by using an antibody that binds to HEG1 protein or an antigen-binding fragment thereof.

Further, the present invention provides a preliminary method (e.g., an industrial method) for diagnosis of mesothelioma in a patient having mesothelioma or a subject at a risk of having mesothelioma by using an antibody that binds to HEG1 protein or an antigen-binding fragment thereof. Furthermore, the present invention provides a method of detecting a mesothelioma cell in a patient having mesothelioma or a subject at a risk of having mesothelioma by using an antibody that binds to HEG1 protein or an antigen-binding fragment thereof. In these embodiments, diagnosis of mesothelioma is performed by a physician, and the present invention provides the physician with basic information for diagnosis as a method for diagnosis by the physician.

The present invention provides, in another aspect, an agent or kit for use in diagnosis of mesothelioma in a patient having mesothelioma or a subject at a risk of having mesothelioma, comprising an antibody that binds to HEG1 protein or an antigen-binding fragment thereof. The kit for use in diagnosis may comprise an instruction to detect mesothelioma by using an antibody that binds to HEG1 protein or an antigen-binding fragment thereof. In a certain embodiment, the agent or kit for use in diagnosis may comprise any of the antibodies according to the present invention or an antigen-binding fragment thereof. As described in the following, the agent or kit for use in diagnosis according to the present invention can be used to detect mesothelioma.

Detection of Mesothelioma

The present invention provides a method of diagnosis of mesothelioma, a method of detecting mesothelioma, a method for detecting mesothelioma, and a method of detecting mesothelioma for assisting diagnosis of mesothelioma by a physician, wherein each method comprises contacting the antibody according to the present invention or an antigen-binding fragment thereof with a sample.

For the detection of mesothelioma according to the present invention, the antibody according to the present invention or an antigen-binding fragment thereof is contacted with a sample. In the case that a sample separated from a living body such as cells, a tissue, or a tissue section is used, antibody reaction can be detected by using a method well known to those skilled in the art (e.g., an immunohistological staining method). If antibody reaction is then observed (e.g., in the case of a positive result), the subject from whom the sample is derived is likely to be affected with mesothelioma. Whether a result for antibody reaction is positive can be determined in accordance with an Allred Score method (see Allred D C et al., Mod Pathol, 11: 155-168, 1998). In the Allred Score method, for example, a total score is calculated from the following equation:

$$\text{Total score (TS)} = \text{Proportion score (PS)} + \text{Intensity score (IS)}$$

If the total score is 3 or more, then it can be determined that the result for reaction is positive. PS and IS can be determined from the following score tables.

Score Tables for Allred Score Method
Proportion Score, PS
    0: no staining
    1: a proportion of staining of less than 1%
    2: a proportion of staining of 1% or more and less than 10%
    3: a proportion of staining of 10% or more and less than ⅓
    4: a proportion of staining of ⅓ or more and less than ⅔
    5: a proportion of staining of ⅔ or more
Intensity score, IS
    0: negative
    1: weak staining
    2: intermediate staining
    3: strong staining In a certain embodiment of the present invention, detection of mesothelioma comprises:
    contacting the antibody according to the present invention or an antigen-binding fragment thereof with a sample obtained from a subject suspected to have mesothelioma; and
    detecting the presence of HEG1 protein (preferably, an extracellular domain of HEG1 protein) in the sample by using the antibody according to the present invention.

In a preferred embodiment, the HEG1 protein to be detected in the detection of mesothelioma is HEG1 having glycosylation, more preferably HEG1 protein having O-glycosylation, and even more preferably HEG1 protein having glycosylation obtained from mesothelioma. The detection of mesothelioma may further comprise determining whether mesothelioma is detected by using a staining rate and/or staining intensity as indices or an index. In a certain embodiment, the detection of mesothelioma may comprise determining whether mesothelioma is detected in accordance with the Allred Score method. In a certain embodiment, the detection of mesothelioma may comprise determining that mesothelioma is detected if a total score (TS) in accordance with the Allred Score method is 2 or more, preferably 3 or more.

The detection of mesothelioma in the present invention can be such that the presence of HEG1 protein having glycosylation obtained from mesothelioma is detected in a sample by using an antibody that binds to HEG1 protein having glycosylation obtained from mesothelioma in a glycosylation-dependent manner. The detection of mesothelioma in the present invention may be such that the presence of HEG1 protein having glycosylation obtained from mesothelioma is detected in a sample by using an antibody that binds to HEG1 protein having glycosylation obtained from mesothelioma.

In a certain embodiment of the present invention, in the case that a tissue or a tissue section is used as a sample, an antigen protein or a part thereof can be detected through immunohistological staining with the antibody according to the present invention.

In the method of diagnosis of mesothelioma, method of detecting mesothelioma, method for detecting mesothelioma, or method of detecting mesothelioma for assisting diagnosis of mesothelioma by a physician, it can be determined that mesothelioma is detected from a subject if an antigen recognized by the antibody according to the present invention is contained in the sample.

In the present invention, any of epithelial mesothelioma, biphasic mesothelioma, sarcomatoid mesothelioma, and desmoplastic mesothelioma can be detected by using the antibody according to the present invention. Thus, the mesothelioma to be detected in the present invention is at least one mesothelioma selected from the group consisting of epithelial mesothelioma, biphasic mesothelioma, sarcomatoid mesothelioma, and desmoplastic mesothelioma. While conventional methods suffer from difficulty in detection of sarcomatoid mesothelioma, in particular, use of the antibody according to the present invention enables detection of sarcomatoid mesothelioma. Thus, the mesothelioma to be detected in the present invention can be sarcomatoid mesothelioma.

The present invention enables differential diagnosis to determine whether a subject suspected to have mesothelioma (in particular, epithelial mesothelioma) or lung adenocarcinoma actually has mesothelioma (in particular, epithelial mesothelioma) or has lung adenocarcinoma. Thus, the detection of mesothelioma according to the present invention can be performed for a subject suspected to have mesothelioma (in particular, epithelial mesothelioma) or lung adenocarcinoma. Further, the present invention enables differential diagnosis between mesothelioma and other carcinomas. Thus, the detection of mesothelioma according to the present invention can be performed in a subject suspected to have mesothelioma or another carcinoma.

In the present invention, a conjugate of an imaging probe with the antibody according to the present invention or an antigen-binding fragment thereof, or a fusion protein or complex of the above-defined antibody fragment according to the present invention with intelectin may be used in the detection of mesothelioma, in place of the antibody according to the present invention or an antigen-binding fragment thereof. The fusion protein or complex of the above-defined antibody fragment according to the present invention with intelectin may be in the form of a conjugate with an imaging probe.

EXAMPLES

Example 1: Preparation of Mesothelioma-Specific Antibody

The human malignant pleural mesothelioma-derived cell lines ACC-MESO1 (RCB2292, RIKEN Cell Bank) and ACC-MESO4 (RCB2293, RIKEN Cell Bank) were cultured in RPMI 1640 containing 10% FCS in 10 cm dishes at 37° C. until they reached confluence. Cells were collected from the two cell dishes with a scraper for each cell line, and washed with PBS three times. The cells were mixed and divided into quarters, and each of them was centrifuged to produce a cell precipitate, which was stored at −80° C. The mass of cells for each cell line was approximately 10 mg per cell precipitate.

The cell precipitate stored under freezing was suspended in 100 µL of PBS, and mixed with 100 µL of ADDAVAX™ (squalene-based oil-in-water nano-emulsion) (InvivoGen). The whole resultant was intraperitoneally administered to six week-old Balb/c mice (female), and the cell precipitate stored under freezing was repeatedly administered to each of the mice in the same manner every two weeks. After three immunizations in total, a drop of blood was collected from the tail vein, and the serum was obtained therefrom. A thin section was prepared from AMeX-fixed (Sato Y et al. Am J Pathol 125:431-435 (1986)) ACC-MESO1 and ACC-MESO4 cell precipitates, with which immunostaining was performed to determine whether an antibody for mesothelioma cells was produced. Mice with high antibody titers were each immunized again with the cell precipitate as described above, and after 1 week the spleen was aseptically excised.

The spleen was ground on a stainless steel mesh, and the lymphocytes were dispersed in 10 mL of RPMI 1640. After large cell masses were separated by pipetting, the dispersion was transferred into a 15 mL centrifuge tube, and left to stand for 3 minutes. The cell suspension was transferred into another centrifuge tube with care not to suction a large aggregate, and the cells were washed twice with RPMI 1640, and the number of cells was counted.

Lymphocytes ($6.75 \times 10^7$ cells) and myeloma cells (PAI) ($5.25 \times 10^6$ cells) cultured in advance were mixed together, and washed twice with RPMI 1640, and then a cell fusion operation was performed. In the cell fusion, PEG1500 (Roche Diagnostics K. K.) was used in accordance with a protocol attached to the product. After fusion, the cells were suspended in RPMI 1640 (76 mL) containing 15% FCS, 10% BM Condimed H1 (Roche Diagnostics K. K.), and 1× HAT (Thermo Fisher Scientific, Inc.), and seeded in four 96-well plates in a volume of 200 µL per well (approximately $1.9 \times 10^5$ cells/well). After culturing at 37° C. for 3 days, approximately 100 µL of the culture supernatant was removed and 100 µL of the above-described HAT culture solution was added for medium exchange. On day 5 after fusion, approximately 100 μL of the culture supernatant was removed and RPMI 1640 containing 15% FCS, 10% BM Condimed H1, and 1× HT (Thermo Fisher Scientific, Inc.) was added for medium exchange, and wells with a colony diameter of 5 mm or more after day 7 were screened.

For the screening, immunostaining was performed with thin sections prepared from AMeX-fixed ACC-MESO1 and ACC-MESO4 cell precipitates. The thin sections were blocked with 0.5% casein for 10 minutes, and reacted with 100 μL of a culture supernatant for a hybridoma as a primary antibody for 2 hours. The thin sections were washed with PBS, and then reacted with the EnVision+kits (Dako Japan Ltd.) as a secondary antibody for 30 minutes, and allowed to develop color by using DAB. Screening was performed for 384 wells, and 93 clones were obtained as clones positive for immunostaining. Secondary screening was performed to pick out clones not reactive with a thin section prepared from an AMeX-fixed A549 cell precipitate, and tertiary screening was performed to pick out clones reactive with a formalin-fixed tissue section of mesothelioma. Ultimately, a plurality of clones almost non-reactive with formalin-fixed tissue sections of cancers except mesothelioma (SKM9-2 and SKM10-2) were obtained.

Example 2: Detection of Mesothelioma with Monoclonal Antibody Obtained

Various types of mesothelioma were stained with a monoclonal antibody produced from the SKM9-2 obtained in the above screening.

AMeX-fixed cell precipitates or formalin-fixed tissues were paraffin-embedded to prepare thin sections. Each of the sections was fixed to a microscope slide, and subjected to deparaffinization and dehydration with xylene and ethanol, followed by activation of an antigen under different conditions. Each section was treated with 3% hydrogen peroxide for 5 minutes to deactivate endogenous peroxidase, and then washed with PBS and blocked with 0.5% casein for 10 minutes. After 100 μL of a solution containing a primary antibody was added to each section and treated at room temperature for 2 hours, the section was washed with PBS and allowed to develop color by using a Histofine Simple Stain MAX-PO (Multi) (NICHIREI BIOSCIENCE INC.), Ventana ultraView DAB universal kit (Roche Diagnostics K. K.), or the EnVision+kits. Each section was stained with hematoxylin and then dehydrated, and encapsulated with Malinol (MUTO PURE CHEMICALS CO., LTD.) to observe under a microscope. The conditions for activation of an antigen were as follows: at 98° C. for 40 minutes for calretinin, mesothelin, and the SKM9-2 antigen; and at 95° C. for 64 minutes for cytokeratin 5/6 (CK5/6), podoplanin, and Wilms' tumor gene product 1 (WT-1). The following activation solutions were used: 10 mM Tris buffer (pH 9.0) containing 1 mM ethylenediamine tetraacetate (EDTA) for calretinin, CK5/6, and podoplanin; and 10 mM citrate buffer (pH 6.0) containing 0.1% TWEEN® 20 (polyethylene glycol sorbitan monolaurate, polyoxyethylenesorbitan monolaurate) for WT-1, mesothelin, and the SKM9-2 antigen. The following primary antibodies were used: a rabbit anti-calretinin polyclonal antibody (PAD:DC8) (Life Technologies Japan Ltd., Tokyo, Japan) for calretinin; a mouse anti-cytokeratin 5,6 monoclonal antibody (D5/16B4) (NICHIREI BIOSCIENCE INC.) for CK5/6; a mouse anti-human mesothelin monoclonal antibody (5B2) (Leica Microsystems, Inc., Bannockburn, IL) for mesothelin; a mouse anti-podoplanin monoclonal antibody (D2-40) (Roche Diagnostics K. K.) for podoplanin; and a mouse anti-human WT-1 monoclonal antibody (6F-H2) (Roche Diagnostics K. K.) for WT-1.

Figure 1:
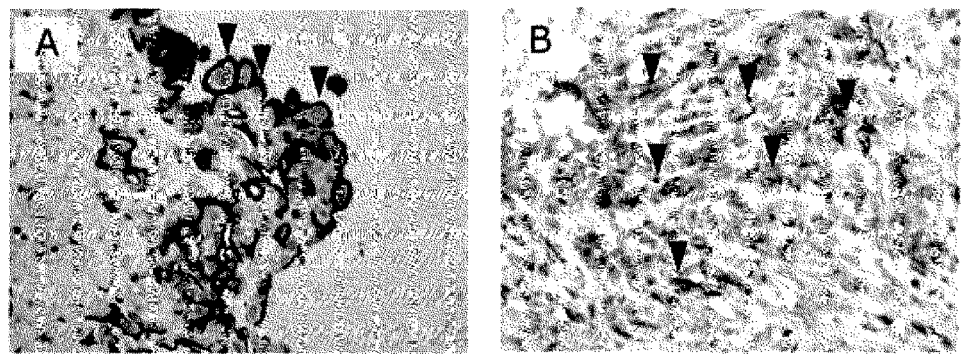
FIG. 1 shows immunohistological staining images of representative mesothelioma subtypes with SKM9-2 antibody, where

Representative staining images of mesothelioma were as shown in FIGS. 1A and 1B. Epithelial mesothelioma (FIG. 1A) and sarcomatoid mesothelioma (FIG. 11B) were successfully stained with the SKM9-2 antibody. As shown in Table 1, the SKM9-2 antibody succeeded in detection of mesothelioma with a higher sensitivity than any other antibodies. Hereinafter, cases that the fraction of cells with scores of 1 or more determined in accordance with the Allred Score method was 10% or more in the cell were determined as positive.

TABLE 1

Detection of mesothelioma with SKM9-2 antibody

| Type of mesothelioma | SKM9-2 antibody | Calretinin | CK5/6 | Podoplanin | WT-1 | Mesothelin |
|---|---|---|---|---|---|---|
| Epithelial | 62/66 | 52/60 | 57/66 | 56/66 | 60/66 | 53/60 |
| Sarcomatoid | 7/9 | 2/9 | 3/9 | 4/9 | 7/9 | 2/9 |
| Biphasic | 12/13 | 10/11 | 11/13 | 10/13 | 11/13 | 8/11 |
| Desmoplastic | 3/4 | 0/4 | 0/4 | 2/4 | 1/4 | 0/4 |
| Sensitivity (%) | 91.3 | 76.2 | 77.2 | 78.3 | 85.9 | 75.0 |

As described above, it was revealed that the SKM9-2 antibody allows detection of each type of mesothelioma with a high sensitivity. In addition, well-differentiated papillary mesothelioma (WDPM), which is a benign or less malignant mesothelioma, was successfully stained with the SKM9-2 antibody (one in one case).

Subsequently, the detection characteristics of the SKM9-2 antibody for other carcinomas were compared with those of other antibodies to confirm the detection specificity to mesothelioma. In this measurement, the detection specificity of each antibody was measured for several carcinomas: gastric carcinoma, colorectal carcinoma, breast carcinoma, ovarian carcinoma, renal cell carcinoma, and urothelial carcinoma, which are more likely to present problems in differential diagnosis of mesothelioma, as "Other carcinomas"; carcinosarcoma, liposarcoma, rhabdomyosarcoma, leiomyosarcoma, fibrosarcoma, synovial sarcoma, gastrointestinal stromal sarcoma (GIST), Ewing's sarcoma, alveolar soft part sarcoma (ASPS), solitary fibrous tumor, malignant peripheral nerve sheath tumor (MPNST), angiosarcoma, epithelioid hemangioendothelioma, epithelioid angiosarcoma, and biphasic synovial sarcoma as "Soft tissue sarcoma"; and chondrosarcoma and osteosarcoma as "Bone sarcoma". The results were as shown in Table 2.

TABLE 2

Mesothelioma specificity of SKM9-2 antibody as compared with antibodies for other markers as antigens

| | SKM9-2 antibody | Calretinin | CK5/6 | Podoplanin | WT-1 | Mesothelin |
|---|---|---|---|---|---|---|
| Lung carcinoma | 0/98 | 23/98 | 41/98 | 13/98 | 0/98 | 44/98 |
| Other carcinomas | 1/60 | 5/60 | 24/60 | 7/60 | 4/60 | 7/60 |
| Soft tissue sarcoma | 2/132 | 27/132 | 22/132 | 34/132 | 7/132 | 9/132 |
| Bone sarcoma | 0/20 | 0/20 | 0/19 | 12/20 | 0/17 | 0/20 |
| Specificity (%) | 99.0 | 82.3 | 71.8 | 78.7 | 96.4 | 80.6 |

As shown in Table 2, it was revealed that the SKM9-2 antibody has high specificity to mesothelioma and enables differential diagnosis between mesothelioma and other types of tumor or cancer with a high precision. In addition, there were very few cases that the SKM9-2 antibody recognized healthy tissues. There were only three cases that a positive result was obtained with the SKM9-2 antibody: urothelial carcinoma (1/10), leiomyosarcoma (1/10), and epithelioid hemangioendothelioma (1/6).

The calretinin antibody, cytokeratin 5/6 antibody, mesothelin antibody, and WT-1 antibody, which are known as conventional antibodies for diagnosis of mesothelioma, each allow detection of epithelial mesothelioma with a high sensitivity. As is clear from Table 2, however, these antibodies are not necessarily superior in specificity, and are known to have difficulty in differential diagnosis between lung adenocarcinoma and epithelial mesothelioma and detection of sarcomatoid mesothelioma. In addition, expressions of calretinin and WT-1 are observed in the cytoplasm in various healthy tissues and carcinoma tissues, leading to a risk of mistaking for an image of nuclear localization characteristic to mesothelioma. From this point, calretinin and WT-1 are not markers which are easy to use and allow easy differential diagnosis. In contrast, the SKM9-2 antibody was superior to conventional antibodies in that it allows simpler differential diagnosis of mesothelioma by whether a result is positive or negative and further allows detection of both epithelial mesothelioma and sarcomatoid mesothelioma. Moreover, the SKM9-2 antibody succeeded in differential diagnosis between mesothelioma and other cancers.

In addition, the reactivity of the SKM9-2 antibody with normal tissues was examined by immunohistological staining. Immunostaining was performed by using the SKM9-2 antibody for healthy tissues without any apparent lesion. The results were as shown in Table 3.

TABLE 3

| Organ | Number of positive cases/number of samples | Organ | Number of positive cases/number of samples |
| --- | --- | --- | --- |
| Esophagus | 0/2 | Thyroid | 0/5 |
| Stomach | 0/3 | Cerebrum | 0/29 |
| Duodenum | 0/2 | Lymph node | 0/4 |
| Large intestine | 0/6 | Mammary gland | 0/5 |
| Liver | 0/8 | Ovary | 0/4 |
| Pancreas | 0/10 | Testis | 1/5 |
| Gallbladder | 0/5 | Prostate | 0/10 |
| Kidney | 0/10 | Muscle | 0/4 |
| Bladder and ureter | 0/5 | Myocardium | 0/12 |
| Pleura | 0/5 | Blood vessel | *5/8 |
| Peritoneum | 0/2 | Bronchus | 0/12 |
| Testicular serosa | 0/1 | Lung | 0/23 |
| Pericardium | 1/1 | | |

*Some cells were positive

As shown in Table 3, although a positive image was found for pericardial mesothelial cells and vascular endothelial cells, most of the tissues were negative. In one case for the testis, the seminiferous tubule was positive. Negative results were obtained for normal mesothelial cells other than pericardial mesothelial cells, which suggest that the SKM9-2 antibody is superior in ability to discriminate between mesothelioma cells and normal tissues. In addition, most of the vascular endothelial cells were negative cells, and positive cells accounted for only a small fraction of the cells.

These results suggest that the antigen recognized by the SKM9-2 antibody can serve as an extremely useful marker for diagnosis of mesothelioma.

Example 3: Analysis of Hybridoma Obtained

Now that it was confirmed that a monoclonal antibody having high specificity to mesothelioma cells was obtained in Examples 1 and 2, identification of the antigen for the SKM9-2 antibody and further analysis of the antigen recognition properties of the antibody were performed.
(1) Purification of Antigen for SKM9-2 Antibody A massive amount of ACC-MESO4 was cultured, and purification of an antigen from the cell lysate was performed. Cells from 240 10-cm dishes were solubilized with 50 mM Tris buffer (pH 8.0) containing 1% TRITON™ X-100 (detergent), 1% CHAPS, 1 mM EDTA, 50 mM NaCl, and protease inhibitor (Complete, Roche Life Science), and then centrifuged. The resulting supernatant was dialyzed with 20 mM acetate buffer (pH 5.0) at 4° C. for 18 hours to afford an acidic precipitate. The precipitate was extracted with 20 mM Tris buffer (pH 7.2) containing 0.1% TWEEN® 20 (polyethylene glycol sorbitan monolaurate, polyoxyethylenesorbitan monolaurate) and 150 mM NaCl and centrifuged, and the resulting supernatant was concentrated by using an Amicon Ultra-15, 100 kDa (Merck Millipore) and subjected to solution exchange with 20 mM Tris buffer (pH 8.0) containing 6 M guanidine hydrochloride. To the concentrated solution, tris(2-carboxyethyl)phosphine hydrochloride with a final concentration of 10 mM was added, and the resultant was heated at 60° C. for 30 minutes, and iodoacetamide with a final concentration of 40 mM was then added thereto, and reacted at room temperature for 3 hours. The reaction solution was subjected to gel filtration chromatography (SUPEROSE® 6 INCREASE (prepacked column) 10/300 GL (GE Healthcare)) in 20 mM Tris buffer (pH 8.0) containing 6 M guanidine hydrochloride and 0.05% TWEEN® 20 (polyethylene glycol sorbitan monolaurate, polyoxyethylenesorbitan monolaurate), and fractions positive for dot blot were collected. The sample was dialyzed with 25 mM phosphate buffer (pH 7.0) containing 4 M urea and 0.05% TWEEN® 20 (polyethylene glycol sorbitan monolaurate, polyoxyethylenesorbitan monolaurate) at room temperature overnight, and applied to a Mono Q 5/50 GL (GE Healthcare). The column was washed with 25 mM phosphate buffer (pH 7.0) containing 4 M urea and 0.05% TWEEN® 20 (polyethylene glycol sorbitan monolaurate, polyoxyethylenesorbitan monolaurate), and thereafter elution was performed with an NaCl salt concentration gradient of 0 to 1 M. Fractions strongly positive for dot blot were collected, and dialyzed with 25 mM phosphate buffer (pH 7.2) containing 150 mM NaCl and 0.05% TWEEN® 20 (polyethylene glycol sorbitan monolaurate, polyoxyethylenesorbitan monolaurate) at room temperature overnight, and applied to 1 mL of WGA-SEPHAROSE® (wheat germ agglutinin-crosslinked, beaded-form of agarose) (J-OIL MILLS, Inc.). After washing with buffer, elution was performed with 25 mM phosphate buffer (pH 7.2) containing 0.2 M N-acetylglucosamine, 150 mM NaCl, and 0.05% TWEEN® 20 (polyethylene glycol sorbitan monolaurate, polyoxyethylenesorbitan monolaurate), and the eluent was concentrated with a Centricon (YM-30) (Millipore). Gel filtration chromatography (SUPEROSE® 6 INCREASE (prepacked column) 10/300 GL (GE Healthcare)) was performed in 25 mM phosphate buffer (pH 7.2) containing 3 M GdnHCl and 0.5% CHAPS, and fractions strongly positive for dot blot were dialyzed with 20 mM $NH_4HCO_3$ containing 0.5% CHAPS at room temperature overnight to afford a purified antigen.

The dot blot was performed as follows. A PVDF membrane (Immobilon-P, Merck Millipore) was soaked in methanol, and then washed and impregnated with pure water. The hydrophilized PVDF membrane was placed on a filter paper containing water to avoid air inclusion, removed of excessive moisture, and soaked with 1 to 5 µL of the sample in dots fed by a micropipette. After the membrane was dried at room temperature overnight, the membrane was hydrophilized again with methanol and pure water, and blocked with 20 mM Tris buffer (pH 7.4) containing 5% skim milk, 0.1% TWEEN® 20 (polyethylene glycol sorbitan monolaurate, polyoxyethylenesorbitan monolaurate), and 150 mM NaCl (blocking buffer) at room temperature for 1 hour. The membrane was reacted with mouse ascites fluid containing the SKM9-2 hybridoma 1,000-fold diluted with the blocking buffer, as a primary antibody, at room temperature for 1 hour, and then washed with 20 mM Tris buffer (pH 7.4) containing 0.1% TWEEN® 20 (polyethylene glycol sorbitan monolaurate, polyoxyethylenesorbitan monolaurate) and 150 mM NaCl (TBST). The membrane was reacted with horseradish peroxidase-labeled goat anti-mouse IgG (Jackson ImmunoResearch Inc.) 30,000-fold diluted with the blocking buffer at room temperature for 1 hour, washed with TBST, and then allowed to develop color by using ECL prime (GE Healthcare) for detection.

The purified antigen was confirmed by Western blotting. The sample was separated by 6% SDS-PAGE or 4-15% Mini-PROTEAN TGX Precast Gels (Bio-Rad Laboratories, Inc.), and transferred onto a PVDF membrane by using a submarine transfer apparatus with 10 mM CAPS buffer (pH 10.5) containing 0.01% SDS. The membrane after the transfer was, in the same manner as in the dot blot, blocked, subjected to antibody reaction, and allowed to develop color by using ECL prime (GE Healthcare) for detection. After being allowed to develop color, the membrane was washed with 20 mM Tris buffer (pH 8.0) containing 6 M guanidine hydrochloride, 0.1% TWEEN®20 (polyethylene glycol sorbitan monolaurate, polyoxyethylenesorbitan monolaurate), and 1% 2-mercaptoethanol at room temperature for 15 minutes, and thoroughly washed with pure water, and thereafter the blocking operation was performed again. As a control antibody, a mouse anti-β-actin monoclonal antibody (Sigma-Aldrich Japan) 5,000-fold diluted was used, and the same operations were performed for detection.

Figure 2:
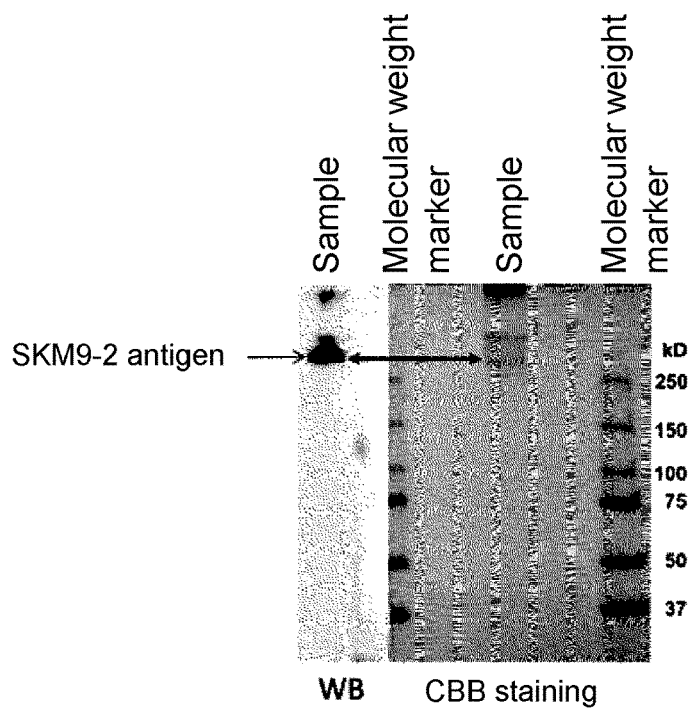
FIG. 2 shows results of Western blot and SDS-PAGE for a purified SKM9-2 antigen.

The results were as shown in FIG. 2. When CBB staining was performed in accordance with a conventional method, a band was detected at a position corresponding to approximately 400 kDa, as shown in FIG. 2, and this band was recognized by the SKM9-2 antibody in Western blotting. This result demonstrates that the antigen for the SKM9-2 antibody was successfully purified through the above operations.

(2) Identification of SKM9-2 Antigen (HEG1)

The band presenting approximately 400 kDa in CBB staining was cut out and treated with peptidase, and then subjected to mass spectrometry (nano-LC MS/MS) to identify a candidate protein through Mascot search. As a result, Protein HEG homolog 1 (HEG1) was obtained as a candidate protein.

However, the estimated molecular weight of HEG1 protein (approximately 150 kDa) was inconsistent with the molecular weight of the antigen for the SKM9-2 antibody estimated by SDS-PAGE in the aforementioned Example, which was approximately 400 kDa. With consideration of this, the following experiment was conducted to determine whether the SKM9-2 antibody is capable of recognizing HEG1 protein.

First, Western blot analysis was performed to see if a band recognized by the SKM9-2 antibody would be weakened through suppression of expression of HEG1. In addition, it was confirmed whether the SKM9-2 antibody is capable of detecting recombinant soluble HEG1 produced in ACC-MESO4 through Western blot analysis.

The following three types of siRNA for human HEG1 (H1097, H2674, H3671) were prepared and suppression of expression of HEG1 was performed.

H1097 sense strand:
(SEQ ID NO: 23)
GAUCUUUGACGGUCAGUCUGG

H1097 antisense strand:
(SEQ ID NO: 24)
AGACUGACCGUCAAAGAUCGC

H2674 sense strand:
(SEQ ID NO: 25)
CCUAUAGCCGUACAGACUACA

H2674 antisense strand:
(SEQ ID NO: 26)
UAGUCUGUACGGCUAUAGGGC

H3671 sense strand:
(SEQ ID NO: 27)
GCAAGUCGGGAUACUUUCAGU

H3671 antisense strand:
(SEQ ID NO: 28)
UGAAAGUAUCCCGACUUGCAC

As a negative control, Mission Negative control SIC-001, confidential sequences (Sigma-Aldrich Japan K.K.) was used.

The specific procedure was as follows. Each siRNA was transfected into ACC-MESO4 by using LIPOFECTAMINE® 2000 (transfection reagent) (Thermo Fisher Scientific, Inc.). The cells were cultured for 72 hours, and thereafter washed with PBS, and 25 µL/cm² of 20 mM Tris buffer (pH 8.0) containing 1% SDS and 125 mU/mL Benzonase nuclease (Merck Millipore) was added thereto, and the resultant was left to stand on ice for 5 minutes, and the lysate was collected. The lysate was centrifuged to obtain a supernatant as a sample, which was separated by 6% SDS-PAGE and then subjected to Western blot. In addition, suppression of expression was performed by using a lentivirus expressing shRNA for human HEG1. Lentiviral particles (sc-78365-V) were obtained for use from Santa Cruz Biotechnology, Inc., and ACC-MESO4 was infected therewith in accordance with the product protocol. After 48 hours, drug selection was initiated with 10 µg/mL of puromycin, and cells which were surviving and proliferating until day 10 were used as cells stably expressing shRNA. Operations performed after solubilization were the same as those for siRNA treatment. As a negative control, cop GFP control lentiviral particles (sc-108084, produced by Santa Cruz Biotechnology, Inc.) were used.

Figure 3:
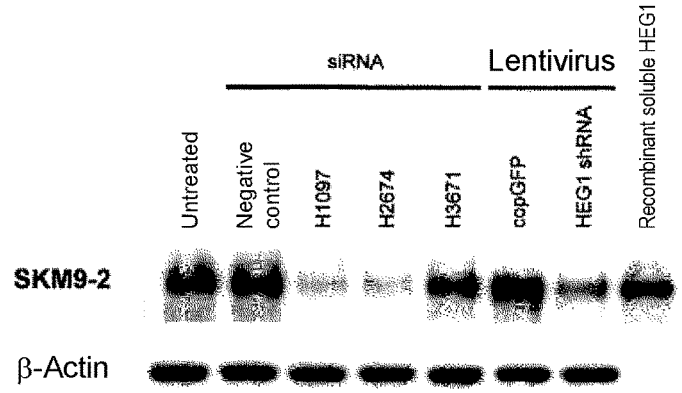
FIG. 3 shows results of Western blot with SKM9-2 antibody for recombinant soluble HEG1 protein expressed by using a cell extract with HEG1 protein knocked down and a mesothelioma cell line.

The results were as shown in FIG. 3. When expression of HEG1 in mesothelioma cells was suppressed with three types of siRNA, the reactivity of the SKM9-2 antibody with the band recognized by the SKM9-2 antibody decreased for any type of siRNA. The reactivity of the SKM9-2 antibody similarly decreased when shRNA for HEG1 was expressed with use of the commercially available lentiviral particles. These results suggest that the SKM9-2 antibody recognizes HEG1 protein.

HEG1 cDNAs (SEQ ID NOs: 32 and 34) were cloned from ACC-MESO4, and a FLAG tag and a His tag were connected to a base sequence corresponding to an extracellular region in the base sequence set forth in SEQ ID NO: 32 (position 1 to position 4059 of SEQ ID NO: 32) to produce a gene (SEQ ID NO: 17), which was inserted between an XhoI site and NotI site of pcDNA3.1 (−) (Thermo Fisher Scientific, Inc.) to prepare a recombinant soluble HEG1 expression plasmid. The plasmid was transfected into ACC-MESO4 by using LIPOFECTAMINE™ LTX REAGENT WITH PLUS™ REAGENT (transfection reagent) (Thermo Fisher Scientific, Inc.), and drug selection was performed by using 750 μg/mL of geneticin (Thermo Fisher Scientific, Inc.). After 2 weeks, surviving and proliferating cells were collected, which were used as cells stably expressing recombinant soluble HEG1. The culture supernatant for the cells in a volume of 40 mL was added to HisTrap excel (1 mL) (GE Healthcare), and the resultant was subjected to elution with 25 mM phosphate buffer (pH 7.2) containing 10 mM imidazole and 0.5 M NaCl with an imidazole concentration gradient of 10 to 500 mM through a column washed in advance with the same buffer. Fractions positive for binding with the SKM9-2 antibody in dot blot were collected, concentrated by using an Amicon Ultra-15, 100 kDa (Merck Millipore), and subjected to solution exchange with 20 mM Tris buffer (pH 8.0) containing 10 mM EDTA and 6 M guanidine hydrochloride followed by solution exchange with 25 mM phosphate buffer (pH 7.2) containing 0.1% TWEEN® 20 (polyethylene glycol sorbitan monolaurate, polyoxyethylenesorbitan monolaurate) to prepare partially purified recombinant soluble HEG1. The recombinant soluble HEG1 had a molecular weight comparable to that of the SKM9-2 antigen, and recognized by the SKM9-2 antibody (FIG. 3). These results suggest that when being produced in mesothelioma, HEG1 protein undergoes post-translational modification or the like and the molecular weight significantly increases, and that the SKM9-2 antibody recognizes the post-translationally modified HEG1 expressed in mesothelioma.

(3) Post-Translational Modification of HEG1 Included in Epitope

The apparent molecular weight of HEG1 protein by SDS-PAGE was approximately 400 kDa, which was considerably higher than the expected molecular weight of the protein, 148 kDa. To figure out the cause, the primary amino acid sequence of HEG1 protein was analyzed, and it was expected from the analysis that HEG1 would undergo a number of 0- and N-glycosylation. On the basis of the expectation, the purified antigen was treated with a glycosidase, and the reactivity of the SKM9-2 antibody was analyzed.

Specifically, HEG1 protein purified from ACC-MESO4 cells were left untreated or treated with an enzyme, and then the reactivity of the SKM9-2 antibody was examined. The examination of the reactivity was performed based on dot blot analysis as described above.

Figure 4:
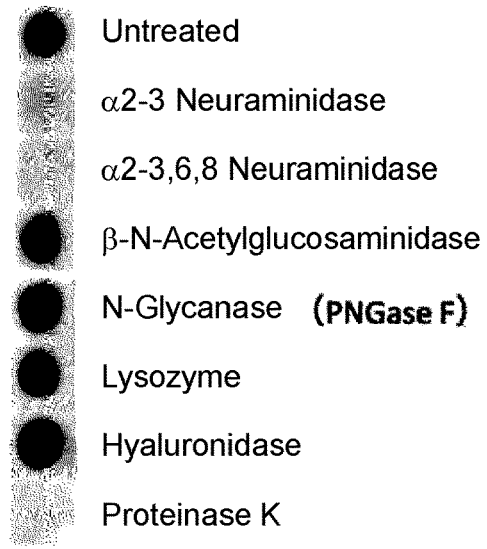
FIG. 4 is a photograph showing the result that antigen recognition by SKM9-2 antibody is weakened by desilylation enzyme treatment.

The results were as shown in FIG. 4. The SKM9-2 antibody did not bind to the antigen treated with neuraminidase as shown in FIG. 4 (the same result was obtained for recombinant soluble HEG1, though not illustrated). The result that the antibody lost the reactivity with the antigen through α2-3 neuraminidase treatment suggests that the epitope for the SKM9-2 antibody includes an α2-3-bonded sugar chain derived from sialylation.

Thus, it was revealed that HEG1 protein in the state of glycosylated form having sialylation was expressed in ACC-MESO4 cells. It was also revealed that the SKM9-2 antibody recognizes HEG1 protein depending on the glycosylation of the HEG1 protein. In Example 1, polyclonal antibodies were obtained from the serum of a mouse immunized with a human malignant pleural mesothelioma-derived cell line, and HEG1 protein was treated with neuraminidase and then dot plot was performed to find that recognition by the HEG1 antibody was weakened by the neuraminidase treatment. From this result, it is inferred that the antibodies obtained included many antibodies capable of recognizing HEG1 protein in a glycosylation-dependent manner.

Further analysis of the results found that N-glycanase (PNGase F) treatment did not cause the antibody to lose the reactivity as shown in FIG. 4, from which the sugar chain included in the epitope was inferred to be an O-linked sugar chain. Furthermore, Proteinase K treatment caused the antibody to lose the reactivity, from which the epitope was expected to include a peptide region. These results suggest that the SKM9-2 antibody is an antibody capable of recognizing the sugar chain part and peptide part of HEG1 protein. On the other hand, commercially available anti-HEG1 antibodies are those for a peptide antigen, and an anti-HEG1 antibody as a goat polyclonal antibody from Santa Cruz Biotechnology, Inc. (HEG1 (N-13): sc-102592) and an anti-HEG1 antibody as a rabbit polyclonal antibody from Bioss Inc. did not react with HEG1 protein purified from mesothelioma.

(4) Localization of HEG1 Protein on Cell Membrane

In consideration that immunohistological staining found localization of HEG1 protein on the cell membrane, examination was made on whether the SKM9-2 antibody binds to the extracellular region or intracellular region of HEG1 protein.

First, ACC-MESO4 was cultured, and cells adhering to the culture dish were peeled off with a scraper. The cells peeled off were reacted with the SKM9-2 antibody, and then treated with FITC-labeled anti-mouse IgG, and analyzed by using a flow cytometer. A 2D2 antibody, which does not bind to any cell, was used as a negative control. If the SKM9-2 antibody binds to the extracellular region of HEG1 protein, cells are to be FITC-labeled and thus fluorescence would be observed in flow cytometry. The result was as shown in FIG. 5.

Figure 5:
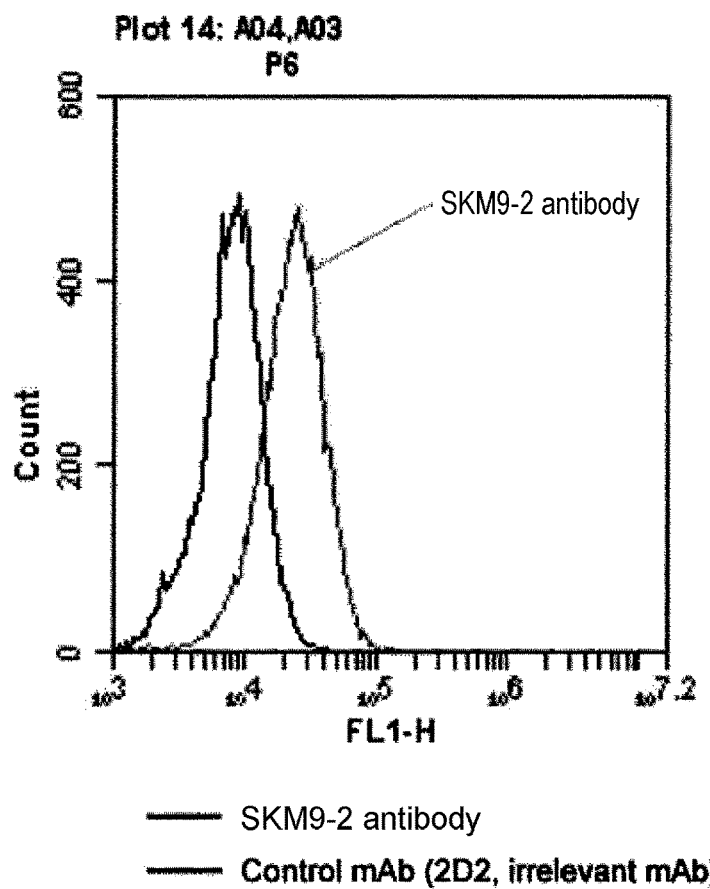
FIG. 5 is a graph showing that an antigen for SKM9-2 antibody is expressed on the cell surface of mesothelioma.

The SKM9-2 antibody was revealed to bind to a HEG1 protein part exposed on the surface of the cell membrane, as shown in FIG. 5.

Example 4: Sequencing of SKM9-2 Antibody

In this Example, the DNA sequence of the SKM9-2 antibody and the amino acid sequence of the SKM9-2 antibody were determined.

Figure 6:
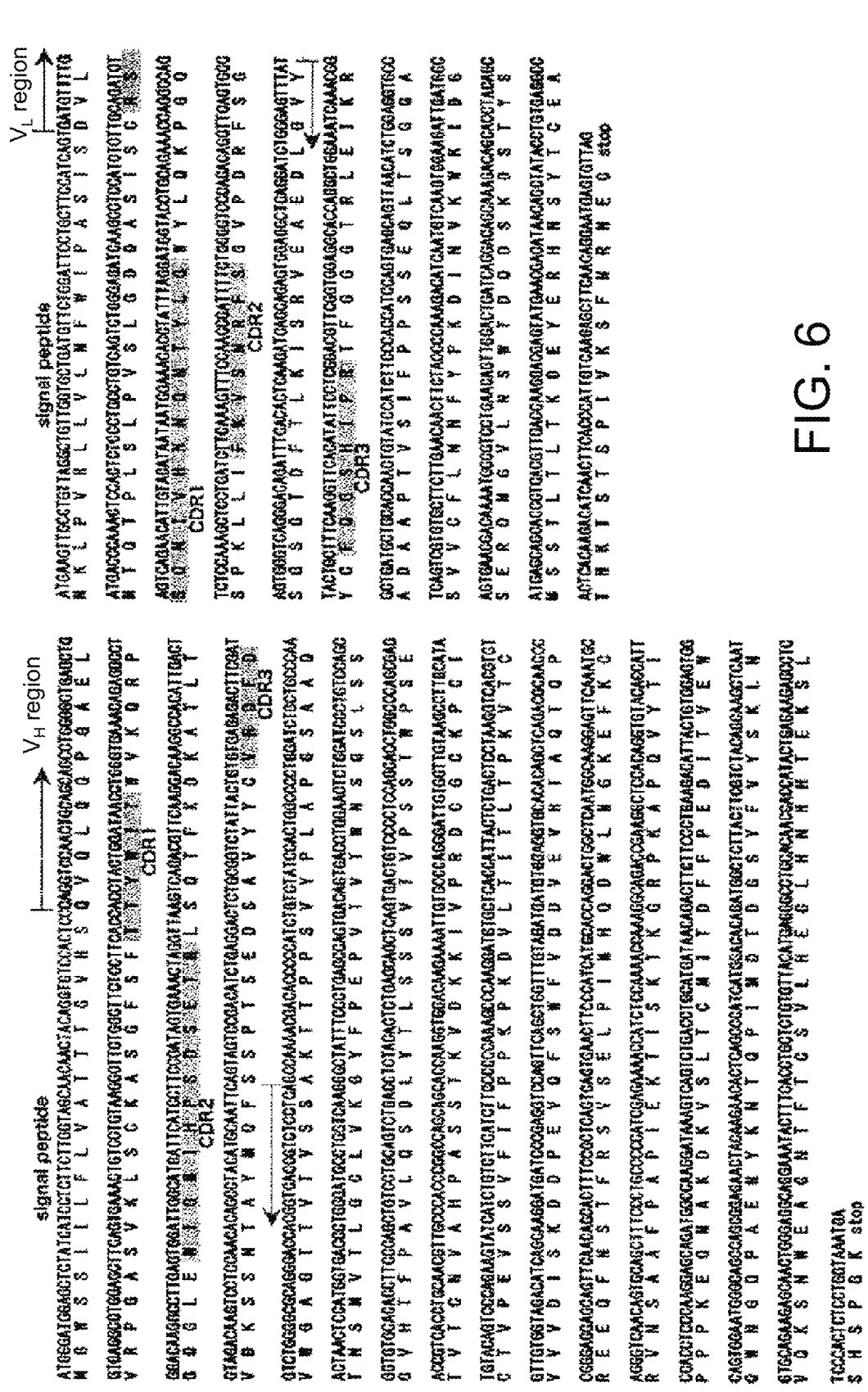
FIG. 6 shows base sequences and amino acid sequences for the heavy chain and light chain in an antibody gene of a hybridoma producing SKM9-2 antibody respectively, where a $V_H$ region and a $V_L$ region are each represented as a region between arrows.

The culture supernatant for the SKM9-2 hybridoma was analyzed by using an IsoStrip Mouse Monoclonal Antibody Isotyping Kit (Roche Diagnostics K. K.), and the result suggested that the subclass of the SKM9-2 antibody was IgG1, and had kappa L chains. Then, RNA was extracted from the hybridoma by using TRizol (Life Technologies), and 5RACE (Takara Bio Inc.) was performed with a primer designed on the basis of information from gene sequence databases for mouse IgG1 and kappa chains. Thereby, the entire base sequences of the open reading frames of the H chain and L chain of the SKM9-2 antibody were determined. The results were as shown in FIG. 6.

Example 5: Reactivity of SKM10-2 Antibody with HEG1 Protein

The reaction specificity of the SKM10-2 antibody, which was obtained as an antibody capable of specifically recognizing mesothelioma in Example 1, was examined.

Figure 7:
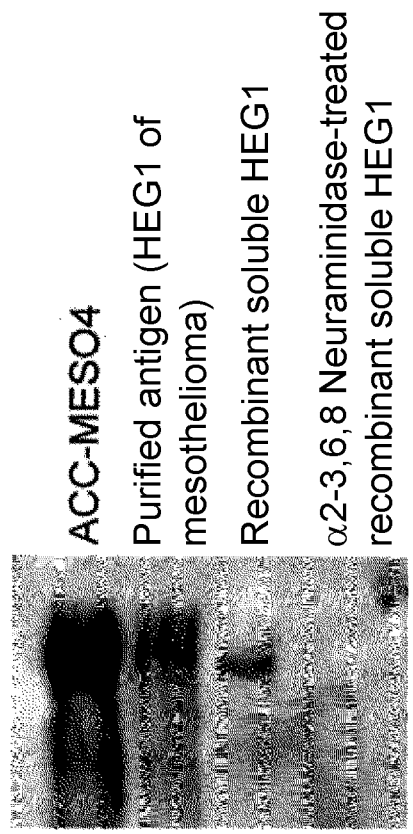
FIG. 7 is a photograph showing that SKM10-2 antibody also allows detection of HEG1 protein in a glycosylation-dependent manner.

The cell lysate containing recombinant soluble HEG1 (see Example 3 (2)) and ACC-MESO4 were separated by 6% SDS-PAGE, and subjected to Western blot with the culture supernatant for the SKM10-2. The results were as shown in FIG. 7. The SKM10-2 antibody recognized HEG1 protein as shown in FIG. 7. In addition, the result shown in FIG. 7 that the SKM10-2 antibody lost the reactivity through sugar chain decomposition treatment revealed that the SKM10-2 antibody is an antibody that binds to HEG1 protein in a glycosylation-dependent manner, similarly to the SKM9-2 antibody. Further, the SKM10-2 antibody is capable of competing with the SKM9-2 antibody for binding to HEG1 protein.

Example 6: Preparation of Intelectin-Fused Fab

A fusion protein of Fab fragments of the SKM9-2 antibody and intelectin was prepared, and examination was made on whether this intelectin-fused antibody is capable of recognizing HEG1 protein.

Figure 8:
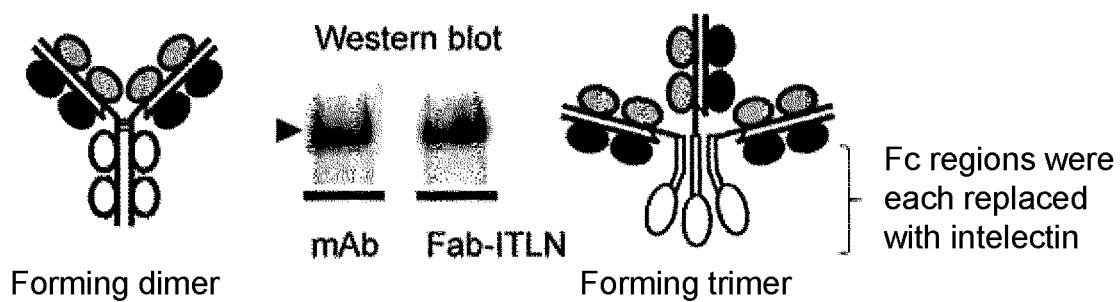
FIG. 8 is a diagram showing that a protein complex including $V_H$ regions and CH1 regions of SKM9-2 antibody fused to intelectin (ITLN) and $V_L$ regions and $C_L$ regions of SKM9-2 antibody (i.e., light chains of SKM9-2 antibody) allows detection of HEG1 protein as with the case of SKM9-2 antibody.

The $V_H$ region and CH1 region of an H chain of the SKM9-2 antibody and amino acids from position 19 to position 313 of human intelectin (SEQ ID NO: 20) were fused together to produce a protein (SEQ ID NO: 21), which was co-expressed with L chains of the SKM9-2 antibody in cells to afford an intelectin-fused antibody. The present inventors have revealed that intelectin has extremely high specificity and high affinity to diol structure, and can be highly purified by using a column packed with diol-modified gel. Accordingly, the culture supernatant containing the intelectin-fused antibody was added to a column packed with diol SEPHAROSE® (crosslinked, beaded-form of agarose), and eluted with 1,2-Propanediol to obtain a purified intelectin-fused antibody. The diol SEPHAROSE® (crosslinked, beaded-form of agarose) was prepared through alkaline hydrolysis of epoxy groups of SEPHAROSE® (crosslinked, beaded-form of agarose) beads including 1,4-Bis(2,3-epoxypropyl)butane introduced thereto (epoxy-activated SEPHAROSE® (crosslinked, beaded-form of agarose) 6B (GE Healthcare Bio-Sciences AB)). Western blot analysis was performed to determine whether the intelectin-fused antibody is capable of recognizing HEG1 protein. In the Western blot, the intelectin-fused antibody was used as a primary antibody, and an anti-human intelectin antibody labeled with horseradish peroxidase was used as a secondary antibody. The results were as shown in FIG. 8, and the intelectin-fused antibody recognized the glycosylated HEG1 protein as with the case of the SKM9-2 antibody.

The present inventors elucidated that intelectin binds to diol structure. RK-13 cells were allowed to forcibly express human intelectin-1, and beads with or without diol structure, as listed in Table 4, were added to 500 µL of the culture supernatant for the RK-13 cells (MEM medium containing recombinant human intelectin-1 and 5% FCS), and the resultant was stirred at 25° C. for 18 hours. Thereafter, the beads were collected through centrifugation, and the beads collected were washed once with 20 mM Tris buffer (pH 7.2) containing 0.1% TWEEN® 20 (polyethylene glycol sorbitan monolaurate, polyoxyethylenesorbitan monolaurate) and 150 mM NaCl, and elution was performed with buffer containing 15% glycerol. The sample eluted was separated by SDS-PAGE, and CBB staining was performed. The diol beads used were beads obtained by bonding 3-Amino-1-propanediol to the surface of polystyrene beads via amino groups, and diol SEPHAROSE® (crosslinked, beaded-form of agarose) beads used were those prepared through alkaline hydrolysis of epoxy groups of SEPHAROSE® (crosslinked, beaded-form of agarose) beads including 1,4-Bis(2,3-epoxypropyl)butane introduced thereto (epoxy-activated SEPHAROSE® (crosslinked, beaded-form of agarose) 6B (GE Healthcare Bio-Sciences AB)).

Figure 9:
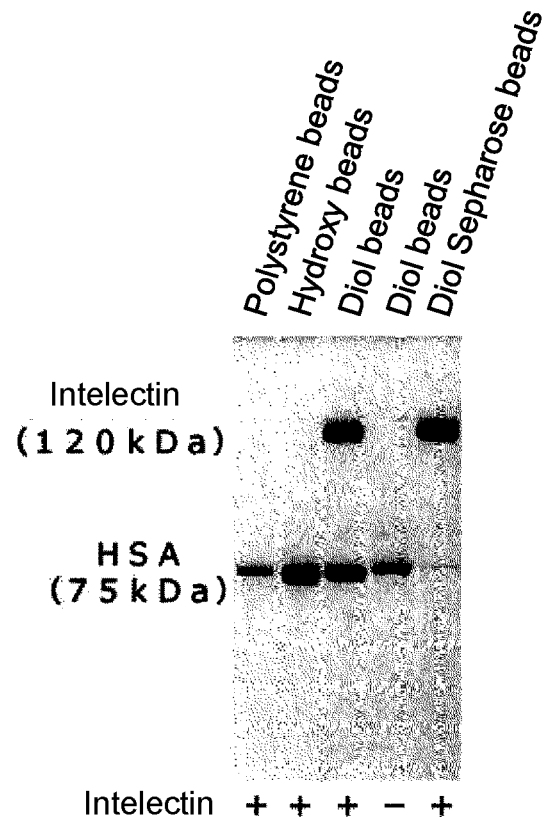
FIG. 9 is a photograph showing that intelectin strongly binds to beads having diol bonds.

The results were as shown in FIG. 9. In short, intelectin strongly bound to the diol beads and the diol SEPHAROSE® (crosslinked, beaded-form of agarose) beads, and did not bind to beads without diol structure.

TABLE 4

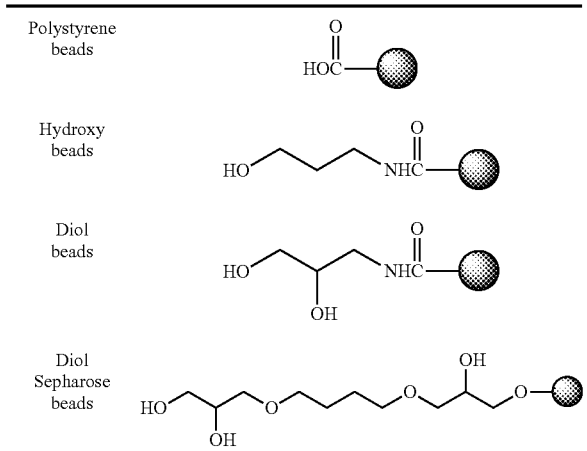

SEPHAROSE® (Crosslinked, Beaded-Form of Agarose)

The binding between intelectin and the diol SEPHAROSE® (crosslinked, beaded-form of agarose) beads was inhibited in the presence of another compound with diol structure. An experiment was conducted in which binding of recombinant human intelectin-1 to a sensor chip including 3-Amino-1-propanediol fixed thereto via amino groups was measured by using a Biacore (GE Healthcare Bio-Sciences AB) in the presence of various compounds serially diluted, where intelectin was used with a final concentration of 0.5 µg/mL, and 10 mM HEPES buffer (pH 7.0) containing 1 mM $CaCl_2$), 150 mM NaCl, and 0.03% TWEEN® 20 (polyethylene glycol sorbitan monolaurate, polyoxyethylenesorbitan monolaurate) was used as buffer for measurement, and the binding rate of intelectin was determined for each sample as the degree of binding of intelectin measured for a sample without addition of compound was defined as a binding rate of 100%.

The results were as shown in Table 5. $IC_{50}$ in inhibiting the binding between intelectin and the diol SEPHAROSE® (crosslinked, beaded-form of agarose) beads was 1 mM or less for L-Ribose, D-Ribose, L-Ascorbic acid, monobutyrin, glycerol, 1,2-Butanediol, 1,2-Propanediol, and (R)-1,2-propanediol (see Table 5). In contrast, $IC_{50}$ was over 100 mM for compounds without diol structure such as ethanol, 1-Propanol, and 3-Amino-1-propanol.

TABLE 5

| Compound | IC$_{50}$ (mM) |
| --- | --- |
| L-Ribose | 0.3 |
| D-Ribose | 0.5 |
| L-Ascorbic acid | 0.8 |
| Monobutyrin | 0.8 |
| Glycerol | 0.8 |
| 1,2-Butanediol | 0.8 |
| 1,2-Propanediol | 0.9 |
| (R)-1,2-Propanediol | 1.0 |

Thus, intelectin binds to diol structure of a compound. Accordingly, intelectin can be purified with the diol SEPHAROSE® (crosslinked, beaded-form of agarose) beads or the like. Moreover, a fusion protein of Fab fragments of the antibody and intelectin was successfully purified with the diol SEPHAROSE® (crosslinked, beaded-form of agarose) beads. It goes without saying that those skilled in the art understand that purification of intelectin fusion protein can be achieved by using a column or beads including any of the compounds listed in Table 5 as a solid phase. Since columns with diol structure can be obtained at low cost, intelectin fusion protein is useful for detection of mesothelioma from the viewpoint of production cost.

Example 7A: Proliferation-Suppressing Effect for Mesothelioma by HEG1 Knock-Down In this Example, HEG1 was knocked down in a mesothelioma cell line by using siRNA for HEG1, and the effect on the cell proliferation of mesothelioma was examined.

An ACC-MESO-4 cell line was used as mesothelioma cells. The cells were seeded in a 96-well plate at 5×10$^3$ cells/well, and cultured with 100 μL of a medium for 24 hours. The cells were washed with PBS, and 15 μL of an Opti-MEM (Thermo Fisher Scientific Inc.) containing 7.5 pmol of siRNA and 0.15 μL of LIPOFECTAMINE® 2000 (transfection reagent) or LIPOFECTAMINE® RNAiMAX (transfection reagent) (Thermo Fisher Scientific Inc.) was added to each well. The cells were cultured for 24 hours, 48 hours, or 72 hours, and the number of surviving cells was counted by using CellTiter 96 AQueous One Solution Cell Proliferation Reagent (Promega K. K., Tokyo, Japan).

For the siRNA, a 1:1 mixture of the above H1097 and H2674 as siRNA1 and commercially available sc-78365 (Santa Cruz Biothechnology, Inc.) as siRNA2 were used, and additionally S3816, SASI_Hs02_00353816; S3817, SASI_Hs02_00353817; and S3818, SASI_Hs02_00353818 (Sigma-Aldrich Japan K.K.) were used.

As H3059,

```
H3059 sense strand:
                                    (SEQ ID NO: 38)
5'-GCGAAUGCGUCGCAGACAACA-3'

H3059 antisense strand:
                                    (SEQ ID NO: 39)
5'-UUGUCUGCGACGCAUUCGCCA-3'
``` was used, and as H9106,

```
H9106 sense strand:
                                    (SEQ ID NO: 40)
5'-CUGGCGUUCUAGUCAGUAAAA-3'
```

```
H9106 antisense strand:
                                    (SEQ ID NO: 41)
5'-UUACUGACUAGAACGCCAGAC-3'
``` was used.

As a control, MISSION siRNA Universal Negative Control (SIC-001) (Sigma-Aldrich Japan K.K., Tokyo, Japan) was used.

Figure 10:
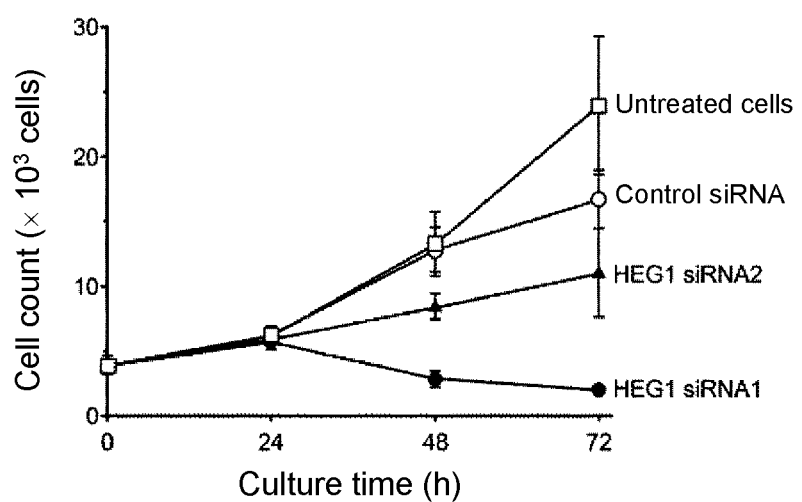
FIG. 10 is a graph showing the effect of HEG1 gene knock-down on cell proliferation of a mesothelioma cell line over time.

The effect of HEG1 knock-down on cell proliferation over time was as shown in FIG. 10. It was revealed as shown in FIG. 10 that the cell proliferation potency in any of the cases with HEG1 knock-down (HEG1 siRNA1 and siRNA2) was lower than those for the control and untreated mesothelioma cell line. The cell count decreased from that before initiation of culture for the HEG1 siRNA1 (FIG. 10). Cell death was induced in some of the mesothelioma cells treated with the HEG1 siRNA1 at hour 48.

Figure 11:
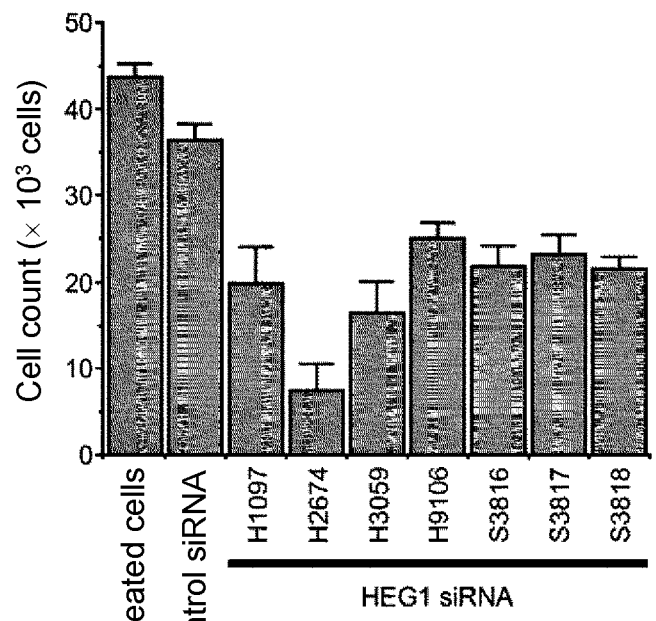
FIG. 11 is a graph showing the effect of HEG1 gene knock-down on cell proliferation of a mesothelioma cell line.

The number of cells 72 hours after introduction of siRNA for HEG1 was checked for each of the above siRNAs. The introduction of siRNA into cells was performed as described in the above. The results were as shown in FIG. 11. The cell proliferation potency of mesothelioma cells was lowered by HEG1 knock-down with any of the siRNAs as shown in FIG. 11.

The siRNA H2674 was introduced into NCI-H2452 cells, as another mesothelioma cell line, and HEK-293T cells, which do not express HEG1. The results were as shown in FIG. 12.

Figure 12:
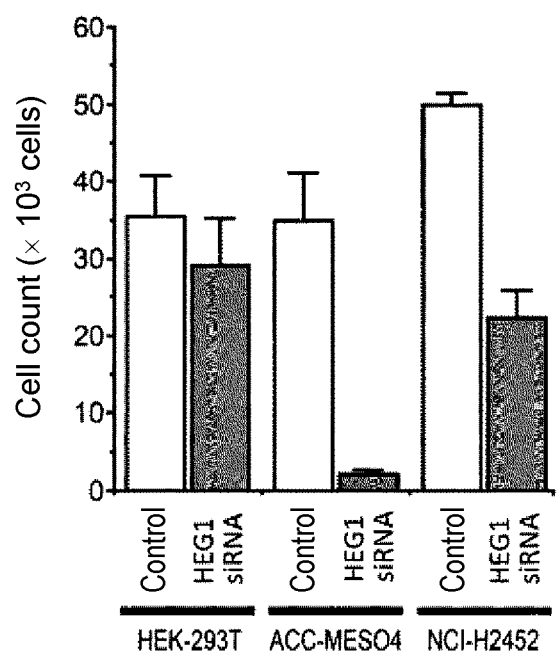
FIG. 12 is a graph showing the effect of HEG1 gene knock-down on cell proliferation of other mesothelioma cell lines.

HEG1 knock-down with the HEG1 siRNA suppressed cell proliferation for another mesothelioma cell line as shown in FIG. 12. On the other hand, HEK-293T cells, which do not express HEG1, were not affected by the siRNA.

These results revealed that expression of HEG1 is highly involved in cell proliferation of mesothelioma. In addition, it was revealed that cell proliferation of mesothelioma can be suppressed through suppression of expression of HEG1. This finding suggests that treatment of cancers involving expression of HEG1 (e.g., mesothelioma) is made possible through inhibition of expression of HEG1 or the cell proliferation-accelerating function of HEG1.

Gene ontology analysis of a HEG1 molecule shows that HEG1 protein has three EGF domains in the extracellular region. For example, the protein MUC4 has an extracellular EGF domain, and is known to bind to ErbB2 (or HER2/neu) to be involved in carcinogenesis. Such information suggests the possibility that the EGF domains of HEG1 protein are similarly involved in oncogenesis. In this Example, cell proliferation of tumor cells was suppressed by HEG1 knock-down. In other words, this Example showed the result that HEG1 protein is necessary for proliferation of tumor cells. This result indicates the possibility that the EGF domains are involved in the cell proliferation-accelerating function of HEG1 protein.

With respect to the intracellular expression site for HEG1, while conventional non-glycosylated HEG1 is expressed at a site of a tight junction between epithelial cells, the glycosylated HEG1 characteristic to mesothelioma is hydrophilic owing to the glycosylation, and expressed on the apical surface of an epithelial cell. This fact also suggests the possibility that HEG1 is involved in intercellular signals or signal transduction associated with cell proliferation.

Example 8A: Determination of Epitope Region

In this Example, the mesothelioma cell line ACC-MESO-1 was allowed to express a human HEG1 fragment with the endogenous HEG1 of ACC-MESO-1 knocked down, and the reactivity with the SKM9-2 antibody was examined. Subsequently, the reactivity with the antibody was tested for the epitope region through alanine scanning, and key amino acids for binding to the antibody were determined.

(1) Analysis of Binding Domain

Gene transfer was performed with HEG1 siRNA (H9106) (SEQ ID NOs: 40, 41) and human HEG1 for the mesothelioma cell line ACC-MESO-1, and the reactivity of the SKM9-2 was examined through Western blot analysis. A full length protein (HEG1 full length) or a fragment (HEG1 3 kb, HEG1 2 kb, or HEG1 1 kb) of the human HEG1 was used. The full length human HEG1 protein, a protein having the amino acid sequence set forth in SEQ ID NO: 35, was obtained through inserting a base sequence set forth in SEQ ID NO: 34 into pFLAG-CMV1 (Sigma-Aldrich Japan K.K.) to obtain a plasmid, transforming the plasmid, and allowing the mesothelioma cell line to express the plasmid. Fragment HEG1 3 kb was obtained through inserting a fragment corresponding to a sequence from position 285, leucine, to position 1387, phenylalanine, of SEQ ID NO: 35 into pFLAG-CMV1 (Sigma-Aldrich Japan K.K.) in an in-frame manner, and allowing the mesothelioma cell line to express the resultant. HEG1 2 kb and HEG1 1 kb were obtained through allowing the mesothelioma cell line to express products similarly obtained from a fragment corresponding to a sequence from position 677, leucine, to position 1387, phenylalanine, of SEQ ID NO: 35 and a fragment corresponding to a sequence from position 992, valine, to position 1387, phenylalanine, of SEQ ID NO: 35, respectively. Each cell lysate was analyzed through Western blot with the SKM9-2 antibody. The results were as shown in FIG. 13 and FIG. 14A.

Figure 13:
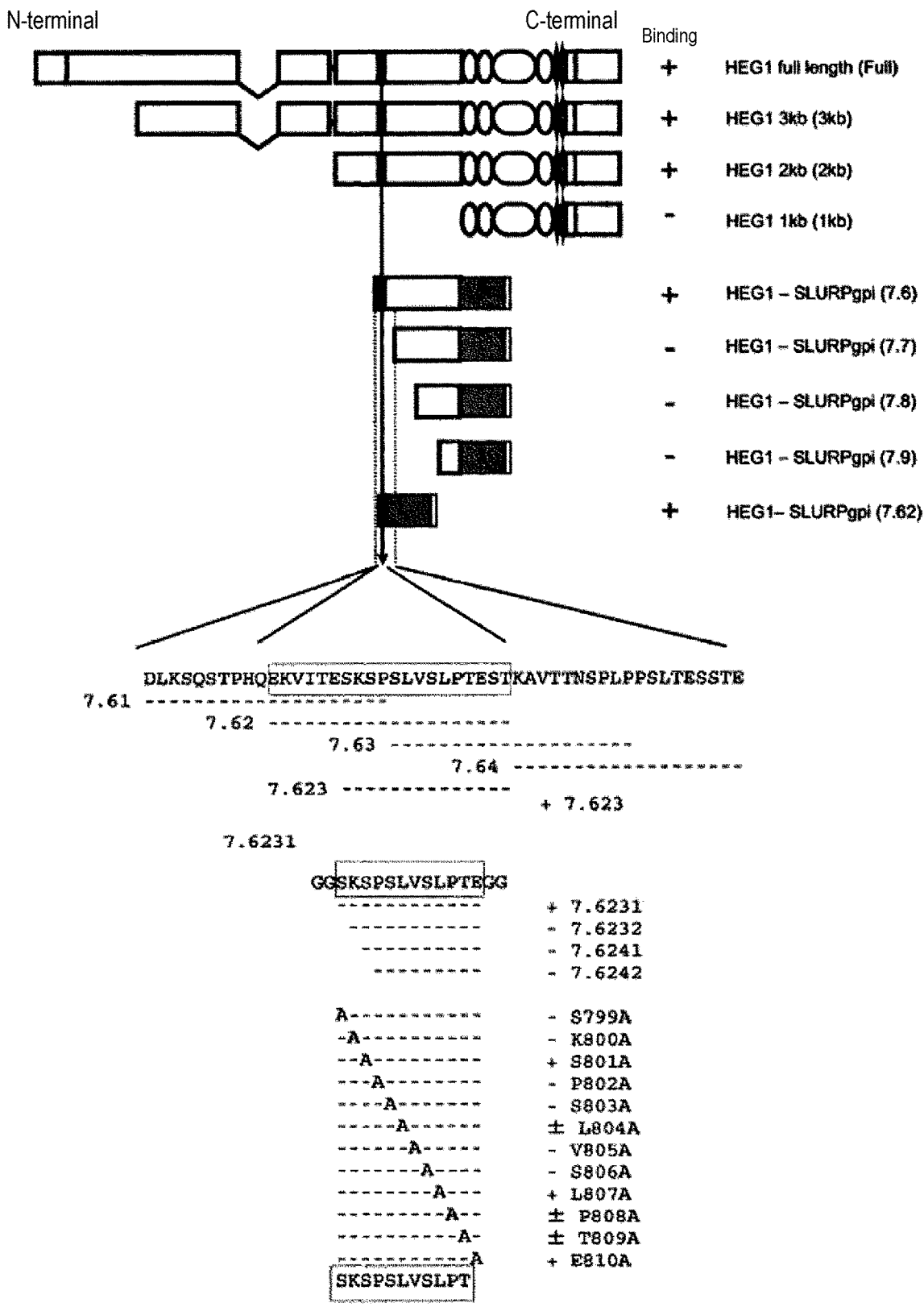
FIG. 13 is a diagram showing whether a human HEG1 fragment is positive (+) or negative (−) for binding to SKM9-2 antibody for each case, where the positions of human HEG1 fragments in HEG1 are illustrated, the bottom portion shows results of alanine scanning, and unmodified amino acids are each represented as the symbol "−". The sequences in the figure are as set forth in the following table.

HEG1 full length, HEG1 3 kb, and HEG1 2 kb, each including exon 7 of HEG1, were positive (+) as shown in FIG. 13 and FIG. 14A. In contrast, HEG1 1 kb was negative (−) for binding to the antibody (FIG. 13 and FIG. 14A).

These results revealed that the SKM9-2 antibody binds to a region in exon 7 of HEG1.

(2) Analysis of Binding Domain—Part 2

Further, the region in exon 7 of HEG1 was analyzed in detail. The amino acid sequence of a part of exon 7 of HEG1 was connected to the N-terminal side of a protein obtained by connecting a GPI anchor signal to human SLURP1 (SEQ ID NO: 42; hereinafter referred to as "SLURPgpi") to produce a fusion protein, and the reactivity of the SKM9-2 was examined through Western blot analysis with the fusion protein. A signal sequence (SEQ ID NO: 43) was added to the N-terminal of the fusion protein before expression.

Used fusion proteins of a partial sequence of exon 7 of HEG1 and SLURPgpi were as follows:

a fragment obtained by bonding a fragment from amino acid No. 783, aspartic acid, to amino acid No. 991, serine, to SLURPgpi (7.6);

a fragment obtained by bonding a fragment from amino acid No. 832, glutamine, to amino acid No. 991, serine, to SLURPgpi (7.7);

a fragment obtained by bonding a fragment from amino acid No. 886, glutamine, to amino acid No. 991, serine, to SLURPgpi (7.8);

a fragment obtained by bonding a fragment from amino acid No. 941, alanine, to amino acid No. 991, serine, to SLURPgpi (7.9);

a fragment obtained by bonding SEQ ID NO: 44 to SLURPgpi (7.61);

a fragment obtained by bonding SEQ ID NO: 45 to SLURPgpi (7.62);

a fragment obtained by bonding SEQ ID NO: 46 to SLURPgpi (7.63);

a fragment obtained by bonding SEQ ID NO: 47 to SLURPgpi (7.64);

a fragment obtained by bonding SEQ ID NO: 48 to SLURPgpi (7.623);

a fragment obtained by bonding SEQ ID NO: 49 to SLURPgpi (7.6231);

a fragment obtained by bonding SEQ ID NO: 50 to SLURPgpi (7.6232);

a fragment obtained by bonding SEQ ID NO: 51 to SLURPgpi (7.6241); and a fragment obtained by bonding SEQ ID NO: 52 to SLURPgpi (7.6242).

The results were as shown in FIG. 13 and FIG. 14B.

The fusion proteins (7.6 and 7.62) were positive as shown in FIG. 13 and FIG. 14B. These results revealed that the SKM9-2 antibody binds to a region including E793 to T812 of HEG1.

As shown in FIG. 13 and FIG. 14C, the fusion proteins (7.623 and 7.6231) were positive. These results revealed that the SKM9-2 antibody binds to a region including S799 to E810 of HEG1.

(3) Analysis of binding site by alanine scanning Subsequently, a S799 to E810 fragment was modified by substitution of one amino acid with alanine, and the resulting fragment was linked to SLURPgpi as described above, and the reactivity with the SKM9-2 antibody was examined through Western blot analysis.

As shown in FIG. 13 and FIG. 14D, it was found that S799 to T809 (SKSPSLVSLPT; SEQ ID NO: 53) is the epitope (linear epitope) for the SKM9-2 antibody.

Further, when a lysate of cells expressing fragment 7.6231 was treated with neuraminidase, the reaction between the fragment and the SKM9-2 antibody disappeared (see FIG. 14E). This result revealed that the epitope recognized by the SKM9-2 antibody includes modification with sialic acid.

SEQUENCE LISTING

SEQ ID NO: 1: nucleic acid sequence of heavy chain of SKM9-2 antibody

SEQ ID NO: 2: amino acid sequence of heavy chain of SKM9-2 antibody

SEQ ID NO: 3: nucleic acid sequence of light chain of SKM9-2 antibody

SEQ ID NO: 4: amino acid sequence of light chain of SKM9-2 antibody

SEQ ID NO: 5: nucleic acid sequence of heavy chain CDR1 of SKM9-2 antibody

SEQ ID NO: 6: amino acid sequence of heavy chain CDR2 of SKM9-2 antibody

SEQ ID NO: 7: nucleic acid sequence of heavy chain CDR2 of SKM9-2 antibody

SEQ ID NO: 8: amino acid sequence of heavy chain CDR2 of SKM9-2 antibody

SEQ ID NO: 9: nucleic acid sequence of heavy chain CDR3 of SKM9-2 antibody

SEQ ID NO: 10: amino acid sequence of heavy chain CDR3 of SKM9-2 antibody

SEQ ID NO: 11: nucleic acid sequence of light chain CDR1 of SKM9-2 antibody

SEQ ID NO: 12: amino acid sequence of light chain CDR2 of SKM9-2 antibody

SEQ ID NO: 13: nucleic acid sequence of light chain CDR2 of SKM9-2 antibody
SEQ ID NO: 14: amino acid sequence of light chain CDR2 of SKM9-2 antibody
SEQ ID NO: 15: nucleic acid sequence of light chain CDR3 of SKM9-2 antibody
SEQ ID NO: 16: amino acid sequence of light chain CDR3 of SKM9-2 antibody
SEQ ID NO: 17: nucleic acid sequence of soluble HEG1 cDNA having FLAG tag and His tag
SEQ ID NO: 18: amino acid sequence encoded by soluble HEG1 cDNA having FLAG tag and His tag
SEQ ID NO: 19: nucleic acid sequence of human intelectin-1 gene
SEQ ID NO: 20: amino acid sequence of human intelectin-1 protein
SEQ ID NO: 21: nucleic acid sequence of fusion gene of SKM9-2 antibody heavy chain and intelectin
SEQ ID NO: 22: amino acid sequence of fusion protein of SKM9-2 antibody heavy chain and intelectin
SEQ ID NO: 23: nucleic acid sequence of sense strand of H1097
SEQ ID NO: 24: nucleic acid sequence of antisense strand of H1097
SEQ ID NO: 25: nucleic acid sequence of sense strand of H2674
SEQ ID NO: 26: nucleic acid sequence of antisense strand of H2674
SEQ ID NO: 27: nucleic acid sequence of sense strand of H3671
SEQ ID NO: 28: nucleic acid sequence of antisense strand of H3671
SEQ ID NO: 29: nucleic acid sequence of HEG1 gene registered as NM_020733.1
SEQ ID NO: 30: amino acid sequence of protein encoded by SEQ ID NO: 29
SEQ ID NO: 31: soluble form of naturally occurring variant of HEG1 protein
SEQ ID NO: 32: nucleic acid sequence of nucleic acid encoding naturally occurring variant of HEG1 protein
SEQ ID NO: 33: amino acid sequence of protein encoded by SEQ ID NO: 32
SEQ ID NO: 34: nucleic acid sequence of nucleic acid encoding naturally occurring variant of HEG1 protein
SEQ ID NO: 35: amino acid sequence of protein encoded by SEQ ID NO: 34
SEQ ID NO: 36: nucleic acid sequence of nucleic acid encoding naturally occurring variant of HEG1 protein
SEQ ID NO: 37: amino acid sequence of protein encoded by SEQ ID NO: 36
SEQ ID NO: 38: nucleic acid sequence of sense strand of H3059
SEQ ID NO: 39: nucleic acid sequence of antisense strand of H3059
SEQ ID NO: 40: nucleic acid sequence of sense strand of H9106
SEQ ID NO: 41: nucleic acid sequence of antisense strand of H9106
SEQ ID NO: 42: amino acid sequence of SLURPgpi part
SEQ ID NO: 43: signal sequence (amino acid sequence) of SLURPgpi fusion protein
SEQ ID NO: 44: amino acid sequence of HEG1 part in SLURPgpi fragment (7.61)
SEQ ID NO: 45: amino acid sequence of HEG1 part in SLURPgpi fragment (7.62)
SEQ ID NO: 46: amino acid sequence of HEG1 part in SLURPgpi fragment (7.63)
SEQ ID NO: 47: amino acid sequence of HEG1 part in SLURPgpi fragment (7.64)
SEQ ID NO: 48: amino acid sequence of HEG1 part in SLURPgpi fragment (7.623)
SEQ ID NO: 49: amino acid sequence of HEG1 part in SLURPgpi fragment (7.6231)
SEQ ID NO: 50: amino acid sequence of HEG1 part in SLURPgpi fragment (7.6232)
SEQ ID NO: 51: amino acid sequence of HEG1 part in SLURPgpi fragment (7.6241)
SEQ ID NO: 52: amino acid sequence of HEG1 part in SLURPgpi fragment (7.6242)
SEQ ID NO: 53: amino acid sequence from S799 to T809 of HEG1 protein
SEQ ID NO: 54: amino acid sequence of S799A mutant peptide in FIG. 13
SEQ ID NO: 55: amino acid sequence of K800A mutant peptide in FIG. 13
SEQ ID NO: 56: amino acid sequence of S801A mutant peptide in FIG. 13
SEQ ID NO: 57: amino acid sequence of P802A mutant peptide in FIG. 13
SEQ ID NO: 58: amino acid sequence of S803A mutant peptide in FIG. 13
SEQ ID NO: 59: amino acid sequence of L804A mutant peptide in FIG. 13
SEQ ID NO: 60: amino acid sequence of V805A mutant peptide in FIG. 13
SEQ ID NO: 61: amino acid sequence of S806A mutant peptide in FIG. 13
SEQ ID NO: 62: amino acid sequence of L807A mutant peptide in FIG. 13
SEQ ID NO: 63: amino acid sequence of P808A mutant peptide in FIG. 13
SEQ ID NO: 64: amino acid sequence of T809A mutant peptide in FIG. 13
SEQ ID NO: 65: amino acid sequence of E810A mutant peptide in FIG. 13
SEQ ID NO: 66: amino acid sequence 7.6 of FIG. 13.
SEQ ID NO: 67: amino acid sequence 7.61 of FIG. 13.
SEQ ID NO: 68: amino acid sequence 7.62 of FIG. 13.
SEQ ID NO: 69: amino acid sequence 7.63 of FIG. 13.
SEQ ID NO: 70: amino acid sequence 7.64 of FIG. 13.
SEQ ID NO: 71: amino acid sequence 7.623 of FIG. 13.
SEQ ID NO: 72: amino acid sequence above 7.6231 of FIG. 13.
SEQ ID NO: 88: amino acid sequence 7.6231 of FIG. 13.
SEQ ID NO: 73: amino acid sequence 7.6232 of FIG. 13.
SEQ ID NO: 74: amino acid sequence 7.6241 of FIG. 13.
SEQ ID NO: 75: amino acid sequence 7.6242 of FIG. 13.
SEQ ID NO: 76: amino acid sequence S799A of FIG. 13.
SEQ ID NO: 77: amino acid sequence K800A of FIG. 13.
SEQ ID NO: 78: amino acid sequence S801A of FIG. 13.
SEQ ID NO: 79: amino acid sequence P802A of FIG. 13.
SEQ ID NO: 80: amino acid sequence S803A of FIG. 13.
SEQ ID NO: 81: amino acid sequence L804A of FIG. 13.
SEQ ID NO: 82: amino acid sequence V805A of FIG. 13.
SEQ ID NO: 83: amino acid sequence S806A of FIG. 13.
SEQ ID NO: 84: amino acid sequence L807A of FIG. 13.
SEQ ID NO: 85: amino acid sequence P808A of FIG. 13.
SEQ ID NO: 86: amino acid sequence T809A of FIG. 13.
SEQ ID NO: 87: amino acid sequence E8 OA of FIG. 13.
SEQ ID NO: 89: amino acid sequence at bottom of FIG. 13.

The invention claimed is:

1. A monoclonal antibody that binds to HEG1 protein having O-glycosylation having sialylation obtained from mesothelioma or HEG1 protein on a cell membrane of mesothelioma, or an antigen-binding fragment thereof, wherein the antibody and the antigen-binding fragment each comprise a heavy chain variable region comprising a CDR1 having the amino acid sequence set forth in SEQ ID NO: 6, a CDR2 having the amino acid sequence set forth in SEQ ID NO:8, and a CDR3 having the amino acid sequence set forth in SEQ ID NO: 10, and a light chain variable region comprising a CDR1 having the amino acid sequence set forth in SEQ ID NO: 12, a CDR2 having the amino acid sequence set forth in SEQ ID NO: 14, and a CDR3 having the amino acid sequence set forth in SEQ ID NO: 16.

2. A protein complex comprising (A) and (B) below:
(A) a fusion protein of an antibody $V_H$ region with human intelectin protein; and
(B) an antibody light chain,
wherein the antibody $V_H$ region comprises a heavy chain variable region comprising a CDR1 having the amino acid sequence set forth in SEQ ID NO: 6, a CDR2 having the amino acid sequence set forth in SEQ ID NO:8, and a CDR3 having the amino acid sequence set forth in SEQ ID NO: 10, and the antibody light chain comprises a light chain variable region comprising a CDR1 having the amino acid sequence set forth in SEQ ID NO: 12, a CDR2 having the amino acid sequence set forth in SEQ ID NO: 14, and a CDR3 having the amino acid sequence set forth in SEQ ID NO: 16.

3. A method of detecting mesothelioma in a human subject, comprising detecting HEG1 protein in a tissue sample obtained from the human subject by using the monoclonal antibody or the antigen-binding fragment thereof according to claim 1.

4. A method of detecting mesothelioma in a human subject, comprising detecting HEG1 protein in a tissue sample obtained from the human subject by using the protein complex according to claim 2.

5. The protein complex of claim 2, wherein the fusion protein is a fusion protein of (a) a $V_H$ region and CH1 region of an antibody with (b) human intelectin protein.

* * * * *

SEQUENCE LISTING

<160> NUMBER OF SEQ ID NOS: 89

<210> SEQ ID NO 1
<211> LENGTH: 1371
<212> TYPE: DNA
<213> ORGANISM: Mus musculus
<220> FEATURE:
<221> NAME/KEY: CDS
<222> LOCATION: (1)..(1368)

<400> SEQUENCE: 1

| | | | | | | | | | | | | | | | | |
|---|---|---|---|---|---|---|---|---|---|---|---|---|---|---|---|---|
| atg | gga | tgg | agc | tct | atc | atc | ctc | ttc | ttg | gta | gca | aca | act | aca | ggt | 48 |
| Met | Gly | Trp | Ser | Ser | Ile | Ile | Leu | Phe | Leu | Val | Ala | Thr | Thr | Thr | Gly | |
| 1 | | | | 5 | | | | | 10 | | | | | 15 | | |

| gtc | cac | tcc | cag | gtc | caa | ctg | cag | cag | cct | ggg | gct | gag | ctg | gtg | agg | 96 |
|---|---|---|---|---|---|---|---|---|---|---|---|---|---|---|---|---|
| Val | His | Ser | Gln | Val | Gln | Leu | Gln | Gln | Pro | Gly | Ala | Glu | Leu | Val | Arg | |
| | | | 20 | | | | | 25 | | | | | 30 | | | |

| cct | gga | gct | tca | gtg | aaa | ctg | tcc | tgt | aag | gct | tct | ggc | ttc | tcc | ttc | 144 |
|---|---|---|---|---|---|---|---|---|---|---|---|---|---|---|---|---|
| Pro | Gly | Ala | Ser | Val | Lys | Leu | Ser | Cys | Lys | Ala | Ser | Gly | Phe | Ser | Phe | |
| | | 35 | | | | | 40 | | | | | 45 | | | | |

| acc | acc | tac | tgg | ata | acc | tgg | gtg | aaa | cag | agg | cct | gga | caa | ggc | ctt | 192 |
|---|---|---|---|---|---|---|---|---|---|---|---|---|---|---|---|---|
| Thr | Thr | Tyr | Trp | Ile | Thr | Trp | Val | Lys | Gln | Arg | Pro | Gly | Gln | Gly | Leu | |
| | 50 | | | | | 55 | | | | | 60 | | | | | |

| gag | tgg | att | ggc | atg | att | cat | cct | tcc | gat | agt | gaa | act | agg | tta | agt | 240 |
|---|---|---|---|---|---|---|---|---|---|---|---|---|---|---|---|---|
| Glu | Trp | Ile | Gly | Met | Ile | His | Pro | Ser | Asp | Ser | Glu | Thr | Arg | Leu | Ser | |
| 65 | | | | | 70 | | | | | 75 | | | | | 80 | |

| cag | acg | ttc | aag | gac | aag | gcc | aca | ttg | act | gta | gac | aag | tcc | tcc | aac | 288 |
|---|---|---|---|---|---|---|---|---|---|---|---|---|---|---|---|---|
| Gln | Thr | Phe | Lys | Asp | Lys | Ala | Thr | Leu | Thr | Val | Asp | Lys | Ser | Ser | Asn | |
| | | | | 85 | | | | | 90 | | | | | 95 | | |

| aca | gcc | tac | atg | caa | ttc | agt | agt | ccg | aca | tct | gag | gac | tct | gcg | gtc | 336 |
|---|---|---|---|---|---|---|---|---|---|---|---|---|---|---|---|---|
| Thr | Ala | Tyr | Met | Gln | Phe | Ser | Ser | Pro | Thr | Ser | Glu | Asp | Ser | Ala | Val | |
| | | | 100 | | | | | 105 | | | | | 110 | | | |

| tat | tac | tgt | gtg | aga | gac | ttc | gat | gtc | tgg | ggc | gca | ggg | acc | acg | gtc | 384 |
|---|---|---|---|---|---|---|---|---|---|---|---|---|---|---|---|---|
| Tyr | Tyr | Cys | Val | Arg | Asp | Phe | Asp | Val | Trp | Gly | Ala | Gly | Thr | Thr | Val | |
| | | 115 | | | | | 120 | | | | | 125 | | | | |

| acc | gtc | tcc | tca | gcc | aaa | acg | aca | ccc | cca | tct | gtc | tat | cca | ctg | gcc | 432 |
|---|---|---|---|---|---|---|---|---|---|---|---|---|---|---|---|---|
| Thr | Val | Ser | Ser | Ala | Lys | Thr | Thr | Pro | Pro | Ser | Val | Tyr | Pro | Leu | Ala | |
| | 130 | | | | | 135 | | | | | 140 | | | | | |

| cct | gga | tct | gct | gcc | caa | act | aac | tcc | atg | gtg | acc | ctg | gga | tgc | ctg | 480 |
|---|---|---|---|---|---|---|---|---|---|---|---|---|---|---|---|---|
| Pro | Gly | Ser | Ala | Ala | Gln | Thr | Asn | Ser | Met | Val | Thr | Leu | Gly | Cys | Leu | |
| 145 | | | | | 150 | | | | | 155 | | | | | 160 | |

| gtc | aag | ggc | tat | ttc | cct | gag | cca | gtg | aca | gtg | acc | tgg | aac | tct | gga | 528 |
|---|---|---|---|---|---|---|---|---|---|---|---|---|---|---|---|---|
| Val | Lys | Gly | Tyr | Phe | Pro | Glu | Pro | Val | Thr | Val | Thr | Trp | Asn | Ser | Gly | |
| | | | | 165 | | | | | 170 | | | | | 175 | | |

| tcc | ctg | tcc | agc | ggt | gtg | cac | acc | ttc | cca | gct | gtc | ctg | cag | tct | gac | 576 |
|---|---|---|---|---|---|---|---|---|---|---|---|---|---|---|---|---|
| Ser | Leu | Ser | Ser | Gly | Val | His | Thr | Phe | Pro | Ala | Val | Leu | Gln | Ser | Asp | |
| | | | 180 | | | | | 185 | | | | | 190 | | | |

| ctc | tac | act | ctg | agc | agc | tca | gtg | act | gtc | ccc | tcc | agc | acc | tgg | ccc | 624 |
|---|---|---|---|---|---|---|---|---|---|---|---|---|---|---|---|---|
| Leu | Tyr | Thr | Leu | Ser | Ser | Ser | Val | Thr | Val | Pro | Ser | Ser | Thr | Trp | Pro | |
| | | 195 | | | | | 200 | | | | | 205 | | | | |

| agc | gag | acc | gtc | acc | tgc | aac | gtt | gcc | cac | ccg | gcc | agc | agc | acc | aag | 672 |
|---|---|---|---|---|---|---|---|---|---|---|---|---|---|---|---|---|
| Ser | Glu | Thr | Val | Thr | Cys | Asn | Val | Ala | His | Pro | Ala | Ser | Ser | Thr | Lys | |
| | 210 | | | | | 215 | | | | | 220 | | | | | |

| gtg | gac | aag | aaa | att | gtg | ccc | agg | gat | tgt | ggt | tgt | aag | cct | tgc | ata | 720 |
|---|---|---|---|---|---|---|---|---|---|---|---|---|---|---|---|---|
| Val | Asp | Lys | Lys | Ile | Val | Pro | Arg | Asp | Cys | Gly | Cys | Lys | Pro | Cys | Ile | |
| 225 | | | | | 230 | | | | | 235 | | | | | 240 | |

| tgt | aca | gtc | cca | gaa | gta | tca | tct | gtc | ttc | atc | ttc | ccc | cca | aag | ccc | 768 |
|---|---|---|---|---|---|---|---|---|---|---|---|---|---|---|---|---|
| Cys | Thr | Val | Pro | Glu | Val | Ser | Ser | Val | Phe | Ile | Phe | Pro | Pro | Lys | Pro | |
| | | | | 245 | | | | | 250 | | | | | 255 | | |

| aag | gat | gtg | ctc | acc | att | act | ctg | act | cct | aag | gtc | acg | tgt | gtt | gtg | 816 |
|---|---|---|---|---|---|---|---|---|---|---|---|---|---|---|---|---|
| Lys | Asp | Val | Leu | Thr | Ile | Thr | Leu | Thr | Pro | Lys | Val | Thr | Cys | Val | Val | |

```
                260                 265                 270
gta gac atc agc aag gat gat ccc gag gtc cag ttc agc tgg ttt gta     864
Val Asp Ile Ser Lys Asp Asp Pro Glu Val Gln Phe Ser Trp Phe Val
        275                 280                 285 gat gat gtg gag gtg cac aca gct cag acg caa ccc cgg gag gag cag     912
Asp Asp Val Glu Val His Thr Ala Gln Thr Gln Pro Arg Glu Glu Gln
290                 295                 300 ttc aac agc act ttc cgc tca gtc agt gaa ctt ccc atc atg cac cag     960
Phe Asn Ser Thr Phe Arg Ser Val Ser Glu Leu Pro Ile Met His Gln
305                 310                 315                 320 gac tgg ctc aat ggc aag gag ttc aaa tgc agg gtc aac agt gca gct    1008
Asp Trp Leu Asn Gly Lys Glu Phe Lys Cys Arg Val Asn Ser Ala Ala
            325                 330                 335 ttc cct gcc ccc atc gag aaa acc atc tcc aaa acc aaa ggc aga ccg    1056
Phe Pro Ala Pro Ile Glu Lys Thr Ile Ser Lys Thr Lys Gly Arg Pro
        340                 345                 350 aag gct cca cag gtg tac acc att cca cct ccc aag gag cag atg gcc    1104
Lys Ala Pro Gln Val Tyr Thr Ile Pro Pro Pro Lys Glu Gln Met Ala
    355                 360                 365 aag gat aaa gtc agt ctg acc tgc atg ata aca gac ttc ttc cct gaa    1152
Lys Asp Lys Val Ser Leu Thr Cys Met Ile Thr Asp Phe Phe Pro Glu
370                 375                 380 gac att act gtg gag tgg cag tgg aat ggg cag cca gcg gag aac tac    1200
Asp Ile Thr Val Glu Trp Gln Trp Asn Gly Gln Pro Ala Glu Asn Tyr
385                 390                 395                 400 aag aac act cag ccc atc atg gac aca gat ggc tct tac ttc gtc tac    1248
Lys Asn Thr Gln Pro Ile Met Asp Thr Asp Gly Ser Tyr Phe Val Tyr
                405                 410                 415 agc aag ctc aat gtg cag aag agc aac tgg gag gca gga aat act ttc    1296
Ser Lys Leu Asn Val Gln Lys Ser Asn Trp Glu Ala Gly Asn Thr Phe
            420                 425                 430 acc tgc tct gtg tta cat gag ggc ctg cac aac cac cat act gag aag    1344
Thr Cys Ser Val Leu His Glu Gly Leu His Asn His His Thr Glu Lys
        435                 440                 445 agc ctc tcc cac tct cct ggt aaa tga                                1371
Ser Leu Ser His Ser Pro Gly Lys
    450                 455

<210> SEQ ID NO 2
<211> LENGTH: 456
<212> TYPE: PRT
<213> ORGANISM: Mus musculus

<400> SEQUENCE: 2

Met Gly Trp Ser Ser Ile Ile Leu Phe Leu Val Ala Thr Thr Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Phe Ser Phe
        35                  40                  45

Thr Thr Tyr Trp Ile Thr Trp Val Lys Gln Arg Pro Gly Gln Gly Leu
    50                  55                  60

Glu Trp Ile Gly Met Ile His Pro Ser Asp Ser Glu Thr Arg Leu Ser
65                  70                  75                  80

Gln Thr Phe Lys Asp Lys Ala Thr Leu Thr Val Asp Lys Ser Ser Asn
                85                  90                  95

Thr Ala Tyr Met Gln Phe Ser Ser Pro Thr Ser Glu Asp Ser Ala Val
            100                 105                 110
```

```
Tyr Tyr Cys Val Arg Asp Phe Asp Val Trp Gly Ala Gly Thr Thr Val
            115                 120                 125

Thr Val Ser Ser Ala Lys Thr Thr Pro Pro Ser Val Tyr Pro Leu Ala
130                 135                 140

Pro Gly Ser Ala Ala Gln Thr Asn Ser Met Val Thr Leu Gly Cys Leu
145                 150                 155                 160

Val Lys Gly Tyr Phe Pro Glu Pro Val Thr Val Thr Trp Asn Ser Gly
                165                 170                 175

Ser Leu Ser Ser Gly Val His Thr Phe Pro Ala Val Leu Gln Ser Asp
            180                 185                 190

Leu Tyr Thr Leu Ser Ser Val Thr Val Pro Ser Ser Thr Trp Pro
        195                 200                 205

Ser Glu Thr Val Thr Cys Asn Val Ala His Pro Ala Ser Ser Thr Lys
210                 215                 220

Val Asp Lys Lys Ile Val Pro Arg Asp Cys Gly Cys Lys Pro Cys Ile
225                 230                 235                 240

Cys Thr Val Pro Glu Val Ser Ser Val Phe Ile Phe Pro Pro Lys Pro
                245                 250                 255

Lys Asp Val Leu Thr Ile Thr Leu Thr Pro Lys Val Thr Cys Val Val
            260                 265                 270

Val Asp Ile Ser Lys Asp Asp Pro Glu Val Gln Phe Ser Trp Phe Val
275                 280                 285

Asp Asp Val Glu Val His Thr Ala Gln Thr Gln Pro Arg Glu Glu Gln
        290                 295                 300

Phe Asn Ser Thr Phe Arg Ser Val Ser Glu Leu Pro Ile Met His Gln
305                 310                 315                 320

Asp Trp Leu Asn Gly Lys Glu Phe Lys Cys Arg Val Asn Ser Ala Ala
                325                 330                 335

Phe Pro Ala Pro Ile Glu Lys Thr Ile Ser Lys Thr Lys Gly Arg Pro
            340                 345                 350

Lys Ala Pro Gln Val Tyr Thr Ile Pro Pro Lys Glu Gln Met Ala
        355                 360                 365

Lys Asp Lys Val Ser Leu Thr Cys Met Ile Thr Asp Phe Phe Pro Glu
370                 375                 380

Asp Ile Thr Val Glu Trp Gln Trp Asn Gly Gln Pro Ala Glu Asn Tyr
385                 390                 395                 400

Lys Asn Thr Gln Pro Ile Met Asp Thr Asp Gly Ser Tyr Phe Val Tyr
                405                 410                 415

Ser Lys Leu Asn Val Gln Lys Ser Asn Trp Glu Ala Gly Asn Thr Phe
            420                 425                 430

Thr Cys Ser Val Leu His Glu Gly Leu His Asn His Thr Glu Lys
        435                 440                 445

Ser Leu Ser His Ser Pro Gly Lys
450                 455

<210> SEQ ID NO 3
<211> LENGTH: 717
<212> TYPE: DNA
<213> ORGANISM: Mus musculus
<220> FEATURE:
<221> NAME/KEY: CDS
<222> LOCATION: (1)..(714)

<400> SEQUENCE: 3 atg aag ttg cct gtt agg ctg ttg gtg ctg atg ttc tgg att cct gct     48
Met Lys Leu Pro Val Arg Leu Leu Val Leu Met Phe Trp Ile Pro Ala
```

```
1               5                   10                  15
tcc atc agt gat gtt ttg atg acc caa act cca ctc tcc ctg cct gtc         96
Ser Ile Ser Asp Val Leu Met Thr Gln Thr Pro Leu Ser Leu Pro Val
            20                  25                  30 agt ctg gga gat caa gcc tcc atc tct tgc aga tct agt cag aac att        144
Ser Leu Gly Asp Gln Ala Ser Ile Ser Cys Arg Ser Ser Gln Asn Ile
        35                  40                  45 gta cat aat aat gga aac acc tat tta gga tgg tac ctg cag aaa cca        192
Val His Asn Asn Gly Asn Thr Tyr Leu Gly Trp Tyr Leu Gln Lys Pro
50                  55                  60 ggc cag tct cca aag ctc ctg atc ttc aaa gtt tcc aac cga ttt tct        240
Gly Gln Ser Pro Lys Leu Leu Ile Phe Lys Val Ser Asn Arg Phe Ser
65                  70                  75                  80 ggg gtc cca gac agg ttc agt ggc agt ggg tca ggg aca gat ttc aca        288
Gly Val Pro Asp Arg Phe Ser Gly Ser Gly Ser Gly Thr Asp Phe Thr
                85                  90                  95 ctc aag atc agc aga gtg gag gct gag gat ctg gga gtt tat tac tgc        336
Leu Lys Ile Ser Arg Val Glu Ala Glu Asp Leu Gly Val Tyr Tyr Cys
            100                 105                 110 ttt caa ggt tca cat att cct cgg acg ttc ggt gga ggc acc agg ctg        384
Phe Gln Gly Ser His Ile Pro Arg Thr Phe Gly Gly Gly Thr Arg Leu
        115                 120                 125 gaa atc aaa cgg gct gat gct gca cca act gta tcc atc ttc cca cca        432
Glu Ile Lys Arg Ala Asp Ala Ala Pro Thr Val Ser Ile Phe Pro Pro
130                 135                 140 tcc agt gag cag tta aca tct gga ggt gcc tca gtc gtg tgc ttc ttg        480
Ser Ser Glu Gln Leu Thr Ser Gly Gly Ala Ser Val Val Cys Phe Leu
145                 150                 155                 160 aac aac ttc tac ccc aaa gac atc aat gtc aag tgg aag att gat ggc        528
Asn Asn Phe Tyr Pro Lys Asp Ile Asn Val Lys Trp Lys Ile Asp Gly
                165                 170                 175 agt gaa cga caa aat ggc gtc ctg aac agt tgg act gat cag gac agc        576
Ser Glu Arg Gln Asn Gly Val Leu Asn Ser Trp Thr Asp Gln Asp Ser
            180                 185                 190 aaa gac agc acc tac agc atg agc agc acc ctc acg ttg acc aag gac        624
Lys Asp Ser Thr Tyr Ser Met Ser Ser Thr Leu Thr Leu Thr Lys Asp
        195                 200                 205 gag tat gaa cga cat aac agc tat acc tgt gag gcc act cac aag aca        672
Glu Tyr Glu Arg His Asn Ser Tyr Thr Cys Glu Ala Thr His Lys Thr
210                 215                 220 tca act tca ccc att gtc aag agc ttc aac agg aat gag tgt tag             717
Ser Thr Ser Pro Ile Val Lys Ser Phe Asn Arg Asn Glu Cys
225                 230                 235

<210> SEQ ID NO 4
<211> LENGTH: 238
<212> TYPE: PRT
<213> ORGANISM: Mus musculus

<400> SEQUENCE: 4

Met Lys Leu Pro Val Arg Leu Leu Val Leu Met Phe Trp Ile Pro Ala
1               5                   10                  15

Ser Ile Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Asn Ile
        35                  40                  45

Val His Asn Asn Gly Asn Thr Tyr Leu Gly Trp Tyr Leu Gln Lys Pro
    50                  55                  60

Gly Gln Ser Pro Lys Leu Leu Ile Phe Lys Val Ser Asn Arg Phe Ser
```

```
            65                  70                  75                  80
Gly Val Pro Asp Arg Phe Ser Gly Ser Gly Ser Gly Thr Asp Phe Thr
                    85                  90                  95

Leu Lys Ile Ser Arg Val Glu Ala Glu Asp Leu Gly Val Tyr Tyr Cys
                100                 105                 110

Phe Gln Gly Ser His Ile Pro Arg Thr Phe Gly Gly Gly Thr Arg Leu
                115                 120                 125

Glu Ile Lys Arg Ala Asp Ala Ala Pro Thr Val Ser Ile Phe Pro Pro
            130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
                180                 185                 190

Lys Asp Ser Thr Tyr Ser Met Ser Ser Thr Leu Thr Leu Thr Lys Asp
                195                 200                 205

Glu Tyr Glu Arg His Asn Ser Tyr Thr Cys Glu Ala Thr His Lys Thr
            210                 215                 220

Ser Thr Ser Pro Ile Val Lys Ser Phe Asn Arg Asn Glu Cys
225                 230                 235
```

```
<210> SEQ ID NO 5
<211> LENGTH: 18
<212> TYPE: DNA
<213> ORGANISM: Mus musculus
<220> FEATURE:
<221> NAME/KEY: CDS
<222> LOCATION: (1)..(18)

<400> SEQUENCE: 5 acc acc tac tgg ata acc                                                  18
Thr Thr Tyr Trp Ile Thr
1               5

<210> SEQ ID NO 6
<211> LENGTH: 6
<212> TYPE: PRT
<213> ORGANISM: Mus musculus

<400> SEQUENCE: 6

Thr Thr Tyr Trp Ile Thr
1               5

<210> SEQ ID NO 7
<211> LENGTH: 39
<212> TYPE: DNA
<213> ORGANISM: Mus musculus
<220> FEATURE:
<221> NAME/KEY: CDS
<222> LOCATION: (1)..(39)

<400> SEQUENCE: 7 tgg att ggc atg att cat cct tcc gat agt gaa act agg                      39
Trp Ile Gly Met Ile His Pro Ser Asp Ser Glu Thr Arg
1               5                   10

<210> SEQ ID NO 8
<211> LENGTH: 13
<212> TYPE: PRT
<213> ORGANISM: Mus musculus
```

<400> SEQUENCE: 8

Trp Ile Gly Met Ile His Pro Ser Asp Ser Glu Thr Arg
1               5                   10

<210> SEQ ID NO 9
<211> LENGTH: 15
<212> TYPE: DNA
<213> ORGANISM: Mus musculus
<220> FEATURE:
<221> NAME/KEY: CDS
<222> LOCATION: (1)..(15)

<400> SEQUENCE: 9 gtg aga gac ttc gat                                              15
Val Arg Asp Phe Asp
1               5

<210> SEQ ID NO 10
<211> LENGTH: 5
<212> TYPE: PRT
<213> ORGANISM: Mus musculus

<400> SEQUENCE: 10

Val Arg Asp Phe Asp
1               5

<210> SEQ ID NO 11
<211> LENGTH: 48
<212> TYPE: DNA
<213> ORGANISM: Mus musculus
<220> FEATURE:
<221> NAME/KEY: CDS
<222> LOCATION: (1)..(48)

<400> SEQUENCE: 11 aga tct agt cag aac att gta cat aat aat gga aac acc tat tta gga       48
Arg Ser Ser Gln Asn Ile Val His Asn Asn Gly Asn Thr Tyr Leu Gly
1               5                   10                  15

<210> SEQ ID NO 12
<211> LENGTH: 16
<212> TYPE: PRT
<213> ORGANISM: Mus musculus

<400> SEQUENCE: 12

Arg Ser Ser Gln Asn Ile Val His Asn Asn Gly Asn Thr Tyr Leu Gly
1               5                   10                  15

<210> SEQ ID NO 13
<211> LENGTH: 24
<212> TYPE: DNA
<213> ORGANISM: Mus musculus
<220> FEATURE:
<221> NAME/KEY: CDS
<222> LOCATION: (1)..(24)

<400> SEQUENCE: 13 ttc aaa gtt tcc aac cga ttt tct                                  24
Phe Lys Val Ser Asn Arg Phe Ser
1               5

<210> SEQ ID NO 14
<211> LENGTH: 8
<212> TYPE: PRT
<213> ORGANISM: Mus musculus

<400> SEQUENCE: 14

```
Phe Lys Val Ser Asn Arg Phe Ser
1               5

<210> SEQ ID NO 15
<211> LENGTH: 32
<212> TYPE: DNA
<213> ORGANISM: Mus musculus
<220> FEATURE:
<221> NAME/KEY: CDS
<222> LOCATION: (1)..(24)

<400> SEQUENCE: 15 ttt caa ggt tca cat att cct cgg acgttcgg                            32
Phe Gln Gly Ser His Ile Pro Arg
1               5

<210> SEQ ID NO 16
<211> LENGTH: 8
<212> TYPE: PRT
<213> ORGANISM: Mus musculus

<400> SEQUENCE: 16

Phe Gln Gly Ser His Ile Pro Arg
1               5

<210> SEQ ID NO 17
<211> LENGTH: 4110
<212> TYPE: DNA
<213> ORGANISM: Homo sapiens
<220> FEATURE:
<221> NAME/KEY: CDS
<222> LOCATION: (1)..(4107)

<400> SEQUENCE: 17 atg gcc tcg ccg cgc gcc tcg cgg tgg ccg ccg ccg ctc ctg ctg ctg    48
Met Ala Ser Pro Arg Ala Ser Arg Trp Pro Pro Pro Leu Leu Leu Leu
1               5                   10                  15 ttg ctg ccg ctg ctg ctg ctg ccg ccg gcg gcc ccc ggg acg cgg gac    96
Leu Leu Pro Leu Leu Leu Leu Pro Pro Ala Ala Pro Gly Thr Arg Asp
                20                  25                  30 ccg ccg cct tcc ccg gct cgc cgc gcg ctg agc ctg gcg ccc ctc gcg   144
Pro Pro Pro Ser Pro Ala Arg Arg Ala Leu Ser Leu Ala Pro Leu Ala
            35                  40                  45 gga gcg ggg ctg gag ctg cag ctg gag cgc cgc ccg gag cgc gag ccg   192
Gly Ala Gly Leu Glu Leu Gln Leu Glu Arg Arg Pro Glu Arg Glu Pro
        50                  55                  60 ccg ccc acg ccg ccc cgg gag cgc cgc ggg ccc gcg acc ccc ggc ccc   240
Pro Pro Thr Pro Pro Arg Glu Arg Arg Gly Pro Ala Thr Pro Gly Pro
65                  70                  75                  80 agc tac agg gcc cct gag cca ggc gcc gcg aca cag cgg gga ccc tcc   288
Ser Tyr Arg Ala Pro Glu Pro Gly Ala Ala Thr Gln Arg Gly Pro Ser
                85                  90                  95 ggc cgg gcc ccc aga ggc ggg agc gcg gat gct gcc tgg aaa cat tgg   336
Gly Arg Ala Pro Arg Gly Gly Ser Ala Asp Ala Ala Trp Lys His Trp
                100                 105                 110 cca gaa agt aac act gag gcc cat gta gaa aac atc acc ttc tat cag   384
Pro Glu Ser Asn Thr Glu Ala His Val Glu Asn Ile Thr Phe Tyr Gln
            115                 120                 125 aat caa gag gac ttt tca aca gtg tcc tcc aaa gag ggc gtg atg gtt   432
Asn Gln Glu Asp Phe Ser Thr Val Ser Ser Lys Glu Gly Val Met Val
        130                 135                 140 cag acc tct ggg aag agc cat gct gct tcg gat gct cca gaa aac ctc   480
Gln Thr Ser Gly Lys Ser His Ala Ala Ser Asp Ala Pro Glu Asn Leu
```

```
                 145                 150                 155                 160
     act cta ctc gct gaa aca gca gat gct aga gga agg agc ggc tct tca         528
     Thr Leu Leu Ala Glu Thr Ala Asp Ala Arg Gly Arg Ser Gly Ser Ser
                     165                 170                 175 agt aga aca aac ttc acc att ttg cct gtt ggg tac tca ctg gag ata         576
     Ser Arg Thr Asn Phe Thr Ile Leu Pro Val Gly Tyr Ser Leu Glu Ile
                 180                 185                 190 gca aca gct ctg act tcc cag agt ggc aac tta gcc tcg gaa agt ctt         624
     Ala Thr Ala Leu Thr Ser Gln Ser Gly Asn Leu Ala Ser Glu Ser Leu
                     195                 200                 205 cac ctg cca tcc agc agt tca gag ttc gat gaa aga att gcc gct ttt         672
     His Leu Pro Ser Ser Ser Ser Glu Phe Asp Glu Arg Ile Ala Ala Phe
                 210                 215                 220 caa aca aag agt gga aca gcc tcg gag atg gga aca gag agg gcg atg         720
     Gln Thr Lys Ser Gly Thr Ala Ser Glu Met Gly Thr Glu Arg Ala Met
     225                 230                 235                 240 ggg ctg tca gaa gaa tgg act gtg cac agc caa gag gcc acc act tcg         768
     Gly Leu Ser Glu Glu Trp Thr Val His Ser Gln Glu Ala Thr Thr Ser
                     245                 250                 255 gct tgg agc ccg tcc ttt ctt cct gct ttg gag atg gga gag ctg acc         816
     Ala Trp Ser Pro Ser Phe Leu Pro Ala Leu Glu Met Gly Glu Leu Thr
                 260                 265                 270 acg cct tct agg aag aga aat tcc tca gga cca gat ctc tcc tgg ctg         864
     Thr Pro Ser Arg Lys Arg Asn Ser Ser Gly Pro Asp Leu Ser Trp Leu
                     275                 280                 285 cat ttc tac agg aca gca gct tcc tct cct ctc tta gac ctt tcc tca         912
     His Phe Tyr Arg Thr Ala Ala Ser Ser Pro Leu Leu Asp Leu Ser Ser
                 290                 295                 300 tct tct gaa agt aca gag aag ctt aac aac tcc act ggc ctc cag agc         960
     Ser Ser Glu Ser Thr Glu Lys Leu Asn Asn Ser Thr Gly Leu Gln Ser
     305                 310                 315                 320 tcc tca gtc agt caa aca aag aca atg cat gtt gcc acc gtg ttc act        1008
     Ser Ser Val Ser Gln Thr Lys Thr Met His Val Ala Thr Val Phe Thr
                     325                 330                 335 gat ggt ggc ccg aga acg ctg cga tct ttg acg gtc agt ctg gga cct        1056
     Asp Gly Gly Pro Arg Thr Leu Arg Ser Leu Thr Val Ser Leu Gly Pro
                 340                 345                 350 gtg agc aag aca gaa ggc ttc ccc aag gac tcc aga att gcc acg act        1104
     Val Ser Lys Thr Glu Gly Phe Pro Lys Asp Ser Arg Ile Ala Thr Thr
                     355                 360                 365 tca tcc tca gtc ctt ctt tca ccc tct gca gtg aa tcg aga aga aac        1152
     Ser Ser Ser Val Leu Leu Ser Pro Ser Ala Val Glu Ser Arg Arg Asn
                 370                 375                 380 agt aga gta act ggg aat cca ggg gat gag gaa ttc att gaa cca tcc        1200
     Ser Arg Val Thr Gly Asn Pro Gly Asp Glu Glu Phe Ile Glu Pro Ser
     385                 390                 395                 400 aca gaa aat gaa ttt gga ctt acg tct ttg cgt tgg caa aat gat tcc        1248
     Thr Glu Asn Glu Phe Gly Leu Thr Ser Leu Arg Trp Gln Asn Asp Ser
                     405                 410                 415 cca acc ttt gga gaa cat cag ctt gcc agc agc tct gag gtg caa aat        1296
     Pro Thr Phe Gly Glu His Gln Leu Ala Ser Ser Ser Glu Val Gln Asn
                 420                 425                 430 gga agt ccc atg tct cag act gag act gtg tct agg tca gtc gca ccc        1344
     Gly Ser Pro Met Ser Gln Thr Glu Thr Val Ser Arg Ser Val Ala Pro
                     435                 440                 445 atg aga ggt gga gag atc act gca cac tgg ctc ttg acc aac agc aca        1392
     Met Arg Gly Gly Glu Ile Thr Ala His Trp Leu Leu Thr Asn Ser Thr
                 450                 455                 460 aca tct gca gat gtg aca gga agc tct gct tca tat cct gaa ggt gtg        1440
```

```
Thr Ser Ala Asp Val Thr Gly Ser Ser Ala Ser Tyr Pro Glu Gly Val
465                 470                 475                 480 aat gct tca gtg ttg acc cag ttc tca gac tct act gta cag tct gga    1488
Asn Ala Ser Val Leu Thr Gln Phe Ser Asp Ser Thr Val Gln Ser Gly
                485                 490                 495 gga agt cac aca gca ttg gga gat agg agt tat tca gag tct tca tct    1536
Gly Ser His Thr Ala Leu Gly Asp Arg Ser Tyr Ser Glu Ser Ser Ser
            500                 505                 510 aca tct tcc tcg gaa agc ttg aat tca tca gca cca cgt gga gaa cgt    1584
Thr Ser Ser Ser Glu Ser Leu Asn Ser Ser Ala Pro Arg Gly Glu Arg
        515                 520                 525 tcg acc ttg gaa gac agc cga gag cca ggc caa gca cta ggt gac agt    1632
Ser Thr Leu Glu Asp Ser Arg Glu Pro Gly Gln Ala Leu Gly Asp Ser
    530                 535                 540 tcc gcc aat gca gag gac agg act tct ggg gtg ccc tct ctc ggc acc    1680
Ser Ala Asn Ala Glu Asp Arg Thr Ser Gly Val Pro Ser Leu Gly Thr
545                 550                 555                 560 cac acc ttg gct act gtc act gga aac ggg gaa cgc aca ctg cgg tct    1728
His Thr Leu Ala Thr Val Thr Gly Asn Gly Glu Arg Thr Leu Arg Ser
                565                 570                 575 gtc acc ctc acc aac acc agc atg agc acg act tct ggg gaa gca ggc    1776
Val Thr Leu Thr Asn Thr Ser Met Ser Thr Thr Ser Gly Glu Ala Gly
            580                 585                 590 agc cct gca gcg gcc atg ccc caa gaa aca gag ggt gcc tct ctg cac    1824
Ser Pro Ala Ala Ala Met Pro Gln Glu Thr Glu Gly Ala Ser Leu His
        595                 600                 605 gta aac gtg acg gac gac atg ggc ctg gtc tca cgg tca ctg gcc gcc    1872
Val Asn Val Thr Asp Asp Met Gly Leu Val Ser Arg Ser Leu Ala Ala
    610                 615                 620 tcc agt gca ctc gga gtc gct ggg att agc tac ggt caa gtg cgt ggc    1920
Ser Ser Ala Leu Gly Val Ala Gly Ile Ser Tyr Gly Gln Val Arg Gly
625                 630                 635                 640 aca gct att gaa caa agg act tcc agc gac cac aca gac cac acc tac    1968
Thr Ala Ile Glu Gln Arg Thr Ser Ser Asp His Thr Asp His Thr Tyr
                645                 650                 655 ctg tca tct act ttc acc aaa gga gaa cgg gcg tta ctg tcc att aca    2016
Leu Ser Ser Thr Phe Thr Lys Gly Glu Arg Ala Leu Leu Ser Ile Thr
            660                 665                 670 gat aac agt tca tcc tca gac att gtg gag agc tca act tct tat att    2064
Asp Asn Ser Ser Ser Ser Asp Ile Val Glu Ser Ser Thr Ser Tyr Ile
        675                 680                 685 aaa atc tca aac tct tca cat tca gag tat tcc tcc ttt ttt cat gct    2112
Lys Ile Ser Asn Ser Ser His Ser Glu Tyr Ser Ser Phe Phe His Ala
    690                 695                 700 cag act gag aga agt aac atc tca tcc tat gac ggg gaa tat gct cag    2160
Gln Thr Glu Arg Ser Asn Ile Ser Ser Tyr Asp Gly Glu Tyr Ala Gln
705                 710                 715                 720 cct tct act gag tcg cca gtt ctg cat aca tcc aac ctt ccg tcc tac    2208
Pro Ser Thr Glu Ser Pro Val Leu His Thr Ser Asn Leu Pro Ser Tyr
                725                 730                 735 aca ccc acc att aat atg ccg aac act tcg gtt gtt ctg gac act gat    2256
Thr Pro Thr Ile Asn Met Pro Asn Thr Ser Val Val Leu Asp Thr Asp
            740                 745                 750 gct gag ttt gtt agt gac tcc tcc tcc tcc tct tcc tcc tcc tcc tcc    2304
Ala Glu Phe Val Ser Asp Ser Ser Ser Ser Ser Ser Ser Ser Ser Ser
        755                 760                 765 tct tcc tcc tcc tcc tct tct tct tct tca ggg cct cct ttg cct ctg    2352
Ser Ser Ser Ser Ser Ser Ser Ser Ser Gly Pro Pro Leu Pro Leu
770                 775                 780
```

| | |
|---|---|
| ccc tct gtg tca caa tcc cac cat tta ttt tca tca att tta cca tca<br>Pro Ser Val Ser Gln Ser His His Leu Phe Ser Ser Ile Leu Pro Ser<br>785                       790                  795                 800 | 2400 |
| acc agg gcc tct gtg cat cta cta aag tct acc tct gat gca tcc aca<br>Thr Arg Ala Ser Val His Leu Leu Lys Ser Thr Ser Asp Ala Ser Thr<br>                    805                  810                 815 | 2448 |
| cca tgg tct tcc tca cca tca cct tta cca gta tcc tta acg aca tct<br>Pro Trp Ser Ser Ser Pro Ser Pro Leu Pro Val Ser Leu Thr Thr Ser<br>         820                   825                 830 | 2496 |
| aca tct gcc cca ctt tct gtc tca caa aca acc ttg cca cag tca tct<br>Thr Ser Ala Pro Leu Ser Val Ser Gln Thr Thr Leu Pro Gln Ser Ser<br>             835                  840               845 | 2544 |
| tct acc cct gtc ctg ccc agg gca agg gag act cct gtg act tca ttt<br>Ser Thr Pro Val Leu Pro Arg Ala Arg Glu Thr Pro Val Thr Ser Phe<br>850                       855                  860 | 2592 |
| cag aca tca aca atg aca tca ttc atg aca atg ctc cat agt agt caa<br>Gln Thr Ser Thr Met Thr Ser Phe Met Thr Met Leu His Ser Ser Gln<br>865                       870                  875                 880 | 2640 |
| act gca gac ctt aag agc cag agc acc cca cac caa gag aaa gtc att<br>Thr Ala Asp Leu Lys Ser Gln Ser Thr Pro His Gln Glu Lys Val Ile<br>                    885                  890                 895 | 2688 |
| aca gaa tca aag tca cca agc ctg gtg tct ctg ccc aca gag tcc acc<br>Thr Glu Ser Lys Ser Pro Ser Leu Val Ser Leu Pro Thr Glu Ser Thr<br>         900                   905                 910 | 2736 |
| aaa gct gta aca aca aac tct cct ttg cct cca tcc tta aca gag tcc<br>Lys Ala Val Thr Thr Asn Ser Pro Leu Pro Pro Ser Leu Thr Glu Ser<br>             915                  920               925 | 2784 |
| tcc aca gag caa acc ctt cca gcc aca agc acc aac tta gca caa atg<br>Ser Thr Glu Gln Thr Leu Pro Ala Thr Ser Thr Asn Leu Ala Gln Met<br>930                       935                  940 | 2832 |
| tct cca act ttc aca act acc att ctg aag acc tct cag cct ctt atg<br>Ser Pro Thr Phe Thr Thr Thr Ile Leu Lys Thr Ser Gln Pro Leu Met<br>945                       950                  955                 960 | 2880 |
| acc act cct ggc acc ctg tca agc aca gca tct ctg gtc act ggc cct<br>Thr Thr Pro Gly Thr Leu Ser Ser Thr Ala Ser Leu Val Thr Gly Pro<br>                    965                  970                 975 | 2928 |
| ata gcc gta cag act aca gct gga aaa cag ctc tcg ctg acc cat cct<br>Ile Ala Val Gln Thr Thr Ala Gly Lys Gln Leu Ser Leu Thr His Pro<br>         980                   985                 990 | 2976 |
| gaa ata cta gtt cct caa atc tca  aca gaa ggt ggc atc  agc aca gaa<br>Glu Ile Leu Val Pro Gln Ile Ser  Thr Glu Gly Gly Ile  Ser Thr Glu<br>             995                  1000               1005 | 3024 |
| agg aac cga gtg att gtg gat gct acc tct gga ttg  atc cct ttg<br>Arg Asn Arg Val Ile Val Asp Ala Thr Ser Gly Leu  Ile Pro Leu<br>1010                     1015                1020 | 3069 |
| acc agt gta ccc aca tca gca aaa gaa atg acc aca  aag ctt ggc<br>Thr Ser Val Pro Thr Ser Ala Lys Glu Met Thr Thr  Lys Leu Gly<br>1025                     1030                1035 | 3114 |
| gtt aca gca gag tac agc cca gct tca cgt tcc ctc  gga aca tct<br>Val Thr Ala Glu Tyr Ser Pro Ala Ser Arg Ser Leu  Gly Thr Ser<br>1040                     1045                1050 | 3159 |
| cct tct ccc caa acc aca gtt gtt tcc acg gct gaa  gac ttg gct<br>Pro Ser Pro Gln Thr Thr Val Val Ser Thr Ala Glu  Asp Leu Ala<br>1055                     1060                1065 | 3204 |
| ccc aaa tct gcc acc ttt gct gtt cag agc agc aca  cag tca cca<br>Pro Lys Ser Ala Thr Phe Ala Val Gln Ser Ser Thr  Gln Ser Pro<br>1070                     1075                1080 | 3249 |
| aca aca ctg tcc tct tca gcc tca gtc aac agc tgt  gct gtg aac<br>Thr Thr Leu Ser Ser Ser Ala Ser Val Asn Ser Cys  Ala Val Asn<br>1085                     1090                1095 | 3294 |

```
cct tgt ctt cac aat ggc gaa tgc gtc gca gac aac acc agc cgt      3339
Pro Cys Leu His Asn Gly Glu Cys Val Ala Asp Asn Thr Ser Arg
    1100                1105                1110 ggc tac cac tgc agg tgc ccg cct tcc tgg caa ggg gat gat tgc      3384
Gly Tyr His Cys Arg Cys Pro Pro Ser Trp Gln Gly Asp Asp Cys
    1115                1120                1125 agt gtg gat gtg aat gag tgc ctg tcg aac ccc tgc cca tcc aca      3429
Ser Val Asp Val Asn Glu Cys Leu Ser Asn Pro Cys Pro Ser Thr
    1130                1135                1140 gcc atg tgc aac aat act cag gga tcc ttt atc tgc aaa tgc ccg      3474
Ala Met Cys Asn Asn Thr Gln Gly Ser Phe Ile Cys Lys Cys Pro
    1145                1150                1155 gtt ggg tac cag ttg gaa aaa ggg ata tgc aat ttg gtt aga acc      3519
Val Gly Tyr Gln Leu Glu Lys Gly Ile Cys Asn Leu Val Arg Thr
    1160                1165                1170 ttc gtg aca gag ttt aaa tta aag aga act ttt ctt aat aca act      3564
Phe Val Thr Glu Phe Lys Leu Lys Arg Thr Phe Leu Asn Thr Thr
    1175                1180                1185 gtg gaa aaa cat tca gac cta caa gaa gtt gaa aat gag atc acc      3609
Val Glu Lys His Ser Asp Leu Gln Glu Val Glu Asn Glu Ile Thr
    1190                1195                1200 aaa acg tta aat atg tgt ttt tca gcg tta cct agt tac atc cga      3654
Lys Thr Leu Asn Met Cys Phe Ser Ala Leu Pro Ser Tyr Ile Arg
    1205                1210                1215 tct aca gtt cac gcc tct agg gag tcc aac gcg gtg gtg atc tca      3699
Ser Thr Val His Ala Ser Arg Glu Ser Asn Ala Val Val Ile Ser
    1220                1225                1230 ctg caa aca acc ttt tcc ctg gcc tcc aat gtg acg cta ttt gac      3744
Leu Gln Thr Thr Phe Ser Leu Ala Ser Asn Val Thr Leu Phe Asp
    1235                1240                1245 ctg gct gat agg atg cag aaa tgt gtc aac tcc tgc aag tcc tct      3789
Leu Ala Asp Arg Met Gln Lys Cys Val Asn Ser Cys Lys Ser Ser
    1250                1255                1260 gct gag gtc tgc cag ctc ttg gga tct cag agg cgg atc ttt aga      3834
Ala Glu Val Cys Gln Leu Leu Gly Ser Gln Arg Arg Ile Phe Arg
    1265                1270                1275 gcg ggc agc ttg tgc aag cgg aag agt ccc gaa tgt gac aaa gac      3879
Ala Gly Ser Leu Cys Lys Arg Lys Ser Pro Glu Cys Asp Lys Asp
    1280                1285                1290 acc tcc atc tgc act gac ctg gac ggc gtt gcc ctg tgc cag tgc      3924
Thr Ser Ile Cys Thr Asp Leu Asp Gly Val Ala Leu Cys Gln Cys
    1295                1300                1305 aag tcg gga tac ttt cag ttc aac aag atg gac cac tcc tgc cga      3969
Lys Ser Gly Tyr Phe Gln Phe Asn Lys Met Asp His Ser Cys Arg
    1310                1315                1320 gca tgt gaa gat gga tat agg ctt gaa aat gaa acc tgc atg agt      4014
Ala Cys Glu Asp Gly Tyr Arg Leu Glu Asn Glu Thr Cys Met Ser
    1325                1330                1335 tgc cca ttt ggc ctt ggt ggt ctc aac tgt gga aac ccc tat cag      4059
Cys Pro Phe Gly Leu Gly Gly Leu Asn Cys Gly Asn Pro Tyr Gln
    1340                1345                1350 gct agc gac tac aag gat gac gat gac aaa cac cat cac cat cac      4104
Ala Ser Asp Tyr Lys Asp Asp Asp Asp Lys His His His His His
    1355                1360                1365 cat taa                                                           4110
His

<210> SEQ ID NO 18
<211> LENGTH: 1369
```

```
<212> TYPE: PRT
<213> ORGANISM: Homo sapiens

<400> SEQUENCE: 18

Met Ala Ser Pro Arg Ala Ser Arg Trp Pro Pro Leu Leu Leu Leu
1               5                   10                  15

Leu Leu Pro Leu Leu Leu Pro Ala Ala Pro Gly Thr Arg Asp
            20                  25                  30

Pro Pro Pro Ser Pro Ala Arg Arg Ala Leu Ser Leu Ala Pro Leu Ala
                35                  40                  45

Gly Ala Gly Leu Glu Leu Gln Leu Glu Arg Arg Pro Glu Arg Glu Pro
    50                  55                  60

Pro Pro Thr Pro Pro Arg Glu Arg Arg Gly Pro Ala Thr Pro Gly Pro
65                  70                  75                  80

Ser Tyr Arg Ala Pro Glu Pro Gly Ala Ala Thr Gln Arg Gly Pro Ser
                85                  90                  95

Gly Arg Ala Pro Arg Gly Gly Ser Ala Asp Ala Ala Trp Lys His Trp
                100                 105                 110

Pro Glu Ser Asn Thr Glu Ala His Val Glu Asn Ile Thr Phe Tyr Gln
                115                 120                 125

Asn Gln Glu Asp Phe Ser Thr Val Ser Ser Lys Glu Gly Val Met Val
130                 135                 140

Gln Thr Ser Gly Lys Ser His Ala Ala Ser Asp Ala Pro Glu Asn Leu
145                 150                 155                 160

Thr Leu Leu Ala Glu Thr Ala Asp Ala Arg Gly Arg Ser Gly Ser Ser
                165                 170                 175

Ser Arg Thr Asn Phe Thr Ile Leu Pro Val Gly Tyr Ser Leu Glu Ile
                180                 185                 190

Ala Thr Ala Leu Thr Ser Gln Ser Gly Asn Leu Ala Ser Glu Ser Leu
                195                 200                 205

His Leu Pro Ser Ser Ser Glu Phe Asp Gly Arg Ile Ala Ala Phe
                210                 215                 220

Gln Thr Lys Ser Gly Thr Ala Ser Glu Met Gly Thr Glu Arg Ala Met
225                 230                 235                 240

Gly Leu Ser Glu Glu Trp Thr Val His Ser Gln Glu Ala Thr Thr Ser
                245                 250                 255

Ala Trp Ser Pro Ser Phe Leu Pro Ala Leu Glu Met Gly Glu Leu Thr
                260                 265                 270

Thr Pro Ser Arg Lys Arg Asn Ser Ser Gly Pro Asp Leu Ser Trp Leu
                275                 280                 285

His Phe Tyr Arg Thr Ala Ala Ser Ser Pro Leu Leu Asp Leu Ser Ser
                290                 295                 300

Ser Ser Glu Ser Thr Glu Lys Leu Asn Asn Ser Thr Gly Leu Gln Ser
305                 310                 315                 320

Ser Ser Val Ser Gln Thr Lys Thr Met His Val Ala Thr Val Phe Thr
                325                 330                 335

Asp Gly Gly Pro Arg Thr Leu Arg Ser Leu Thr Val Ser Leu Gly Pro
                340                 345                 350

Val Ser Lys Thr Glu Gly Phe Pro Lys Asp Ser Arg Ile Ala Thr Thr
                355                 360                 365

Ser Ser Ser Val Leu Leu Ser Pro Ser Ala Val Glu Ser Arg Arg Asn
                370                 375                 380

Ser Arg Val Thr Gly Asn Pro Gly Asp Glu Glu Phe Ile Glu Pro Ser
385                 390                 395                 400
```

```
Thr Glu Asn Glu Phe Gly Leu Thr Ser Leu Arg Trp Gln Asn Asp Ser
            405                 410                 415

Pro Thr Phe Gly Glu His Gln Leu Ala Ser Ser Glu Val Gln Asn
        420                 425                 430

Gly Ser Pro Met Ser Gln Thr Glu Thr Val Ser Arg Ser Val Ala Pro
            435                 440                 445

Met Arg Gly Gly Glu Ile Thr Ala His Trp Leu Leu Thr Asn Ser Thr
    450                 455                 460

Thr Ser Ala Asp Val Thr Gly Ser Ser Ala Ser Tyr Pro Glu Gly Val
465                 470                 475                 480

Asn Ala Ser Val Leu Thr Gln Phe Ser Asp Ser Thr Val Gln Ser Gly
                485                 490                 495

Gly Ser His Thr Ala Leu Gly Asp Arg Ser Tyr Ser Glu Ser Ser Ser
            500                 505                 510

Thr Ser Ser Ser Glu Ser Leu Asn Ser Ser Ala Pro Arg Gly Glu Arg
        515                 520                 525

Ser Thr Leu Glu Asp Ser Arg Glu Pro Gly Gln Ala Leu Gly Asp Ser
        530                 535                 540

Ser Ala Asn Ala Glu Asp Arg Thr Ser Gly Val Pro Ser Leu Gly Thr
545                 550                 555                 560

His Thr Leu Ala Thr Val Thr Gly Asn Gly Glu Arg Thr Leu Arg Ser
                565                 570                 575

Val Thr Leu Thr Asn Thr Ser Met Ser Thr Thr Ser Gly Glu Ala Gly
            580                 585                 590

Ser Pro Ala Ala Ala Met Pro Gln Glu Thr Glu Gly Ala Ser Leu His
        595                 600                 605

Val Asn Val Thr Asp Asp Met Gly Leu Val Ser Arg Ser Leu Ala Ala
    610                 615                 620

Ser Ser Ala Leu Gly Val Ala Gly Ile Ser Tyr Gly Gln Val Arg Gly
625                 630                 635                 640

Thr Ala Ile Glu Gln Arg Thr Ser Ser Asp His Thr Asp His Thr Tyr
                645                 650                 655

Leu Ser Ser Thr Phe Thr Lys Gly Glu Arg Ala Leu Leu Ser Ile Thr
            660                 665                 670

Asp Asn Ser Ser Ser Ser Asp Ile Val Glu Ser Ser Thr Ser Tyr Ile
        675                 680                 685

Lys Ile Ser Asn Ser Ser His Ser Glu Tyr Ser Ser Phe His Ala
        690                 695                 700

Gln Thr Glu Arg Ser Asn Ile Ser Ser Tyr Asp Gly Glu Tyr Ala Gln
705                 710                 715                 720

Pro Ser Thr Glu Ser Pro Val Leu His Thr Ser Asn Leu Pro Ser Tyr
                725                 730                 735

Thr Pro Thr Ile Asn Met Pro Asn Thr Ser Val Val Leu Asp Thr Asp
            740                 745                 750

Ala Glu Phe Val Ser Asp Ser Ser Ser Ser Ser Ser Ser Ser Ser
        755                 760                 765

Ser Ser Ser Ser Ser Ser Ser Ser Ser Gly Pro Pro Leu Pro Leu
770                 775                 780

Pro Ser Val Ser Gln Ser His His Leu Phe Ser Ser Ile Leu Pro Ser
785                 790                 795                 800

Thr Arg Ala Ser Val His Leu Leu Lys Ser Thr Ser Asp Ala Ser Thr
                805                 810                 815
```

-continued

```
Pro Trp Ser Ser Ser Pro Ser Pro Leu Pro Val Ser Leu Thr Thr Ser
            820                 825                 830

Thr Ser Ala Pro Leu Ser Val Ser Gln Thr Thr Leu Pro Gln Ser Ser
        835                 840                 845

Ser Thr Pro Val Leu Pro Arg Ala Arg Glu Thr Pro Val Thr Ser Phe
850                 855                 860

Gln Thr Ser Thr Met Thr Ser Phe Met Thr Met Leu His Ser Ser Gln
865                 870                 875                 880

Thr Ala Asp Leu Lys Ser Gln Ser Thr Pro His Gln Glu Lys Val Ile
                885                 890                 895

Thr Glu Ser Lys Ser Pro Ser Leu Val Ser Leu Pro Thr Glu Ser Thr
        900                 905                 910

Lys Ala Val Thr Thr Asn Ser Pro Leu Pro Pro Ser Leu Thr Glu Ser
        915                 920                 925

Ser Thr Glu Gln Thr Leu Pro Ala Thr Ser Thr Asn Leu Ala Gln Met
930                 935                 940

Ser Pro Thr Phe Thr Thr Thr Ile Leu Lys Thr Ser Gln Pro Leu Met
945                 950                 955                 960

Thr Thr Pro Gly Thr Leu Ser Ser Thr Ala Ser Leu Val Thr Gly Pro
        965                 970                 975

Ile Ala Val Gln Thr Thr Ala Gly Lys Gln Leu Ser Leu Thr His Pro
        980                 985                 990

Glu Ile Leu Val Pro Gln Ile Ser  Thr Glu Gly Gly Ile  Ser Thr Glu
            995                1000                1005

Arg Asn Arg Val Ile Val Asp Ala Thr Ser Gly Leu Ile Pro Leu
        1010                1015                1020

Thr Ser Val Pro Thr Ser Ala Lys Glu Met Thr Thr Lys Leu Gly
        1025                1030                1035

Val Thr Ala Glu Tyr Ser Pro Ala Ser Arg Ser Leu Gly Thr Ser
        1040                1045                1050

Pro Ser Pro Gln Thr Thr Val Val Ser Thr Ala Glu Asp Leu Ala
        1055                1060                1065

Pro Lys Ser Ala Thr Phe Ala Val Gln Ser Ser Thr Gln Ser Pro
        1070                1075                1080

Thr Thr Leu Ser Ser Ser Ala Ser Val Asn Ser Cys Ala Val Asn
        1085                1090                1095

Pro Cys Leu His Asn Gly Glu Cys Val Ala Asp Asn Thr Ser Arg
        1100                1105                1110

Gly Tyr His Cys Arg Cys Pro Pro Ser Trp Gln Gly Asp Asp Cys
        1115                1120                1125

Ser Val Asp Val Asn Glu Cys Leu Ser Asn Pro Cys Pro Ser Thr
        1130                1135                1140

Ala Met Cys Asn Asn Thr Gln Gly Ser Phe Ile Cys Lys Cys Pro
        1145                1150                1155

Val Gly Tyr Gln Leu Glu Lys Gly Ile Cys Asn Leu Val Arg Thr
        1160                1165                1170

Phe Val Thr Glu Phe Lys Leu Lys Arg Thr Phe Leu Asn Thr Thr
        1175                1180                1185

Val Glu Lys His Ser Asp Leu Gln Glu Val Glu Asn Glu Ile Thr
        1190                1195                1200

Lys Thr Leu Asn Met Cys Phe Ser Ala Leu Pro Ser Tyr Ile Arg
        1205                1210                1215

Ser Thr Val His Ala Ser Arg Glu Ser Asn Ala Val Val Ile Ser
```

```
            1220                1225                1230
Leu Gln Thr Thr Phe Ser Leu Ala Ser Asn Val Thr Leu Phe Asp
        1235                1240                1245
Leu Ala Asp Arg Met Gln Lys Cys Val Asn Ser Cys Lys Ser Ser
        1250                1255                1260
Ala Glu Val Cys Gln Leu Leu Gly Ser Gln Arg Arg Ile Phe Arg
        1265                1270                1275
Ala Gly Ser Leu Cys Lys Arg Lys Ser Pro Glu Cys Asp Lys Asp
        1280                1285                1290
Thr Ser Ile Cys Thr Asp Leu Asp Gly Val Ala Leu Cys Gln Cys
        1295                1300                1305
Lys Ser Gly Tyr Phe Gln Phe Asn Lys Met Asp His Ser Cys Arg
        1310                1315                1320
Ala Cys Glu Asp Gly Tyr Arg Leu Glu Asn Glu Thr Cys Met Ser
        1325                1330                1335
Cys Pro Phe Gly Leu Gly Gly Leu Asn Cys Gly Asn Pro Tyr Gln
        1340                1345                1350
Ala Ser Asp Tyr Lys Asp Asp Asp Lys His His His His His
        1355                1360                1365
His

<210> SEQ ID NO 19
<211> LENGTH: 942
<212> TYPE: DNA
<213> ORGANISM: Homo sapiens
<220> FEATURE:
<221> NAME/KEY: CDS
<222> LOCATION: (1)..(939)

<400> SEQUENCE: 19 atg aac caa ctc agc ttc ctg ctg ttt ctc ata gcg acc acc aga gga     48
Met Asn Gln Leu Ser Phe Leu Leu Phe Leu Ile Ala Thr Thr Arg Gly
1               5                   10                  15 tgg agt aca gat gag gct aat act tac ttc aag gaa tgg acc tgt tct     96
Trp Ser Thr Asp Glu Ala Asn Thr Tyr Phe Lys Glu Trp Thr Cys Ser
            20                  25                  30 tcg tct cca tct ctg ccc aga agc tgc aag gaa atc aaa gac gaa tgt    144
Ser Ser Pro Ser Leu Pro Arg Ser Cys Lys Glu Ile Lys Asp Glu Cys
        35                  40                  45 cct agt gca ttt gat ggc ctg tat ttt ctc cgc act gag aat ggt gtt    192
Pro Ser Ala Phe Asp Gly Leu Tyr Phe Leu Arg Thr Glu Asn Gly Val
    50                  55                  60 atc tac cag acc ttc tgt gac atg acc tct ggg ggt ggc ggc tgg acc    240
Ile Tyr Gln Thr Phe Cys Asp Met Thr Ser Gly Gly Gly Gly Trp Thr
65                  70                  75                  80 ctg gtg gcc agc gtg cat gag aat gac atg cgt ggg aag tgc acg gtg    288
Leu Val Ala Ser Val His Glu Asn Asp Met Arg Gly Lys Cys Thr Val
                85                  90                  95 ggc gat cgc tgg tcc agt cag cag ggc agc aaa gca gac tac cca gag    336
Gly Asp Arg Trp Ser Ser Gln Gln Gly Ser Lys Ala Asp Tyr Pro Glu
            100                 105                 110 ggg gac ggc aac tgg gcc aac tac aac acc ttt gga tct gca gag gcg    384
Gly Asp Gly Asn Trp Ala Asn Tyr Asn Thr Phe Gly Ser Ala Glu Ala
        115                 120                 125 gcc acg agc gat gac tac aag aac cct ggc tac tac gac atc cag gcc    432
Ala Thr Ser Asp Asp Tyr Lys Asn Pro Gly Tyr Tyr Asp Ile Gln Ala
    130                 135                 140 aag gac ctg ggc atc tgg cac gtg ccc aat aag tcc ccc atg cag cac    480
```

```
Lys Asp Leu Gly Ile Trp His Val Pro Asn Lys Ser Pro Met Gln His
145                 150                 155                 160 tgg aga aac agc tcc ctg ctg agg tac cgc acg gac act ggc ttc ctc      528
Trp Arg Asn Ser Ser Leu Leu Arg Tyr Arg Thr Asp Thr Gly Phe Leu
                165                 170                 175 cag aca ctg gga cat aat ctg ttt ggc atc tac cag aaa tat cca gtg      576
Gln Thr Leu Gly His Asn Leu Phe Gly Ile Tyr Gln Lys Tyr Pro Val
            180                 185                 190 aaa tat gga gaa gga aag tgt tgg act gac aac ggc ccg gtg atc cct      624
Lys Tyr Gly Glu Gly Lys Cys Trp Thr Asp Asn Gly Pro Val Ile Pro
        195                 200                 205 gtg gtc tat gat ttt ggc gac gcc cag aaa aca gca tct tat tac tca      672
Val Val Tyr Asp Phe Gly Asp Ala Gln Lys Thr Ala Ser Tyr Tyr Ser
    210                 215                 220 ccc tat ggc cag cgg gaa ttc act gcg gga ttt gtt cag ttc agg gta      720
Pro Tyr Gly Gln Arg Glu Phe Thr Ala Gly Phe Val Gln Phe Arg Val
225                 230                 235                 240 ttt aat aac gag aga gca gcc aac gcc ttg tgt gct gga atg agg gtc      768
Phe Asn Asn Glu Arg Ala Ala Asn Ala Leu Cys Ala Gly Met Arg Val
                245                 250                 255 acc gga tgt aac act gag cac cac tgc att ggt gga gga gga tac ttt      816
Thr Gly Cys Asn Thr Glu His His Cys Ile Gly Gly Gly Gly Tyr Phe
            260                 265                 270 cca gag gcc agt ccc cag cag tgt gga gat ttt tct ggt ttt gat tgg      864
Pro Glu Ala Ser Pro Gln Gln Cys Gly Asp Phe Ser Gly Phe Asp Trp
        275                 280                 285 agt gga tat gga act cat gtt ggt tac agc agc agc cgt gag ata act      912
Ser Gly Tyr Gly Thr His Val Gly Tyr Ser Ser Ser Arg Glu Ile Thr
    290                 295                 300 gag gca gct gtg ctt cta ttc tat cgt tga                              942
Glu Ala Ala Val Leu Leu Phe Tyr Arg
305                 310

<210> SEQ ID NO 20
<211> LENGTH: 313
<212> TYPE: PRT
<213> ORGANISM: Homo sapiens

<400> SEQUENCE: 20

Met Asn Gln Leu Ser Phe Leu Leu Phe Leu Ile Ala Thr Thr Arg Gly
1               5                   10                  15

Trp Ser Thr Asp Glu Ala Asn Thr Tyr Phe Lys Glu Trp Thr Cys Ser
                20                  25                  30

Ser Ser Pro Ser Leu Pro Arg Ser Cys Lys Glu Ile Lys Asp Glu Cys
            35                  40                  45

Pro Ser Ala Phe Asp Gly Leu Tyr Phe Leu Arg Thr Glu Asn Gly Val
        50                  55                  60

Ile Tyr Gln Thr Phe Cys Asp Met Thr Ser Gly Gly Gly Gly Trp Thr
65                  70                  75                  80

Leu Val Ala Ser Val His Glu Asn Asp Met Arg Gly Lys Cys Thr Val
                85                  90                  95

Gly Asp Arg Trp Ser Ser Gln Gln Gly Ser Lys Ala Asp Tyr Pro Glu
            100                 105                 110

Gly Asp Gly Asn Trp Ala Asn Tyr Asn Thr Phe Gly Ser Ala Glu Ala
        115                 120                 125

Ala Thr Ser Asp Asp Tyr Lys Asn Pro Gly Tyr Tyr Asp Ile Gln Ala
    130                 135                 140

Lys Asp Leu Gly Ile Trp His Val Pro Asn Lys Ser Pro Met Gln His
145                 150                 155                 160
```

```
                145                 150                 155                 160
Trp Arg Asn Ser Ser Leu Leu Arg Tyr Arg Thr Asp Thr Gly Phe Leu
                    165                 170                 175

Gln Thr Leu Gly His Asn Leu Phe Gly Ile Tyr Gln Lys Tyr Pro Val
                180                 185                 190

Lys Tyr Gly Glu Gly Lys Cys Trp Thr Asp Asn Gly Pro Val Ile Pro
            195                 200                 205

Val Val Tyr Asp Phe Gly Asp Ala Gln Lys Thr Ala Ser Tyr Tyr Ser
        210                 215                 220

Pro Tyr Gly Gln Arg Glu Phe Thr Ala Gly Phe Val Gln Phe Arg Val
225                 230                 235                 240

Phe Asn Asn Glu Arg Ala Ala Asn Ala Leu Cys Ala Gly Met Arg Val
                245                 250                 255

Thr Gly Cys Asn Thr Glu His His Cys Ile Gly Gly Gly Tyr Phe
                260                 265                 270

Pro Glu Ala Ser Pro Gln Gln Cys Gly Asp Phe Ser Gly Phe Asp Trp
            275                 280                 285

Ser Gly Tyr Gly Thr His Val Gly Tyr Ser Ser Arg Glu Ile Thr
        290                 295                 300

Glu Ala Ala Val Leu Leu Phe Tyr Arg
305                 310
```

<210> SEQ ID NO 21
<211> LENGTH: 1593
<212> TYPE: DNA
<213> ORGANISM: Artificial Sequence
<220> FEATURE:
<223> OTHER INFORMATION: H chain in SKM9-2 INTL-1
<220> FEATURE:
<221> NAME/KEY: CDS
<222> LOCATION: (1)..(1590)

<400> SEQUENCE: 21

```
atg gga tgg agc tct atc atc ctc ttc ttg gta gca aca act aca ggt      48
Met Gly Trp Ser Ser Ile Ile Leu Phe Leu Val Ala Thr Thr Thr Gly
1               5                   10                  15 gtc cac tcc cag gtc caa ctg cag cag cct ggg gct gag ctg gtg agg      96
Val His Ser Gln Val Gln Leu Gln Gln Pro Gly Ala Glu Leu Val Arg
            20                  25                  30 cct gga gct tca gtg aaa ctg tcc tgt aag gct tct ggc ttc tcc ttc     144
Pro Gly Ala Ser Val Lys Leu Ser Cys Lys Ala Ser Gly Phe Ser Phe
        35                  40                  45 acc acc tac tgg ata acc tgg gtg aaa cag agg cct gga caa ggc ctt     192
Thr Thr Tyr Trp Ile Thr Trp Val Lys Gln Arg Pro Gly Gln Gly Leu
    50                  55                  60 gag tgg att ggc atg att cat cct tcc gat agt gaa act agg tta agt     240
Glu Trp Ile Gly Met Ile His Pro Ser Asp Ser Glu Thr Arg Leu Ser
65                  70                  75                  80 cag acg ttc aag gac aag gcc aca ttg act gta gac aag tcc tcc aac     288
Gln Thr Phe Lys Asp Lys Ala Thr Leu Thr Val Asp Lys Ser Ser Asn
                85                  90                  95 aca gcc tac atg caa ttc agt agt ccg aca tct gag gac tct gcg gtc     336
Thr Ala Tyr Met Gln Phe Ser Ser Pro Thr Ser Glu Asp Ser Ala Val
            100                 105                 110 tat tac tgt gtg aga gac ttc gat gtc tgg ggc gca ggg acc acg gtc     384
Tyr Tyr Cys Val Arg Asp Phe Asp Val Trp Gly Ala Gly Thr Thr Val
        115                 120                 125 acc gtc tcc tca gcc aaa acg aca ccc cca tct gtc tat cca ctg gcc     432
Thr Val Ser Ser Ala Lys Thr Thr Pro Pro Ser Val Tyr Pro Leu Ala
```

```
                130             135             140
cct gga tct gct gcc caa act aac tcc atg gtg acc ctg gga tgc ctg    480
Pro Gly Ser Ala Ala Gln Thr Asn Ser Met Val Thr Leu Gly Cys Leu
145                 150                 155                 160 gtc aag ggc tat ttc cct gag cca gtg aca gtg acc tgg aac tct gga    528
Val Lys Gly Tyr Phe Pro Glu Pro Val Thr Val Thr Trp Asn Ser Gly
                165                 170                 175 tcc ctg tcc agc ggt gtg cac acc ttc cca gct gtc ctg cag tct gac    576
Ser Leu Ser Ser Gly Val His Thr Phe Pro Ala Val Leu Gln Ser Asp
            180                 185                 190 ctc tac act ctg agc agc tca gtg act gtc ccc tcc agc acc tgg ccc    624
Leu Tyr Thr Leu Ser Ser Ser Val Thr Val Pro Ser Ser Thr Trp Pro
        195                 200                 205 agc gag acc gtc acc tgc aac gtt gcc cac ccg gcc agc agc acc aag    672
Ser Glu Thr Val Thr Cys Asn Val Ala His Pro Ala Ser Ser Thr Lys
    210                 215                 220 gtg gac aag aaa att gtg ccc agg gat tgt ggt acc gat gag gct aat    720
Val Asp Lys Lys Ile Val Pro Arg Asp Cys Gly Thr Asp Glu Ala Asn
225                 230                 235                 240 act tac ttc aag gaa tgg acc tgt tct tcg tct cca tct ctg ccc aga    768
Thr Tyr Phe Lys Glu Trp Thr Cys Ser Ser Ser Pro Ser Leu Pro Arg
                245                 250                 255 agc tgc aag gaa atc aaa gac gaa tgt cct agt gca ttt gat ggc ctg    816
Ser Cys Lys Glu Ile Lys Asp Glu Cys Pro Ser Ala Phe Asp Gly Leu
            260                 265                 270 tat ttt ctc cgc act gag aat ggt gtt atc tac cag acc ttc tgt gac    864
Tyr Phe Leu Arg Thr Glu Asn Gly Val Ile Tyr Gln Thr Phe Cys Asp
        275                 280                 285 atg acc tct ggg ggt ggc ggc tgg acc ctg gtg gcc agc gtg cat gag    912
Met Thr Ser Gly Gly Gly Gly Trp Thr Leu Val Ala Ser Val His Glu
    290                 295                 300 aat gac atg cgt ggg aag tgc acg gtg ggc gat cgc tgg tcc agt cag    960
Asn Asp Met Arg Gly Lys Cys Thr Val Gly Asp Arg Trp Ser Ser Gln
305                 310                 315                 320 cag ggc agc aaa gca gac tac cca gag ggg gac ggc aac tgg gcc aac    1008
Gln Gly Ser Lys Ala Asp Tyr Pro Glu Gly Asp Gly Asn Trp Ala Asn
                325                 330                 335 tac aac acc ttt gga tct gca gag gcg gcc acg agc gat gac tac aag    1056
Tyr Asn Thr Phe Gly Ser Ala Glu Ala Ala Thr Ser Asp Asp Tyr Lys
            340                 345                 350 aac cct ggc tac tac gac atc cag gcc aag gac ctg ggc atc tgg cac    1104
Asn Pro Gly Tyr Tyr Asp Ile Gln Ala Lys Asp Leu Gly Ile Trp His
        355                 360                 365 gtg ccc aat aag tcc ccc atg cag cac tgg aga aac agc gcc ctg ctg    1152
Val Pro Asn Lys Ser Pro Met Gln His Trp Arg Asn Ser Ala Leu Leu
    370                 375                 380 agg tat cgc acg gac act ggc ttc ctc cag aca ctg gga cat aat ctg    1200
Arg Tyr Arg Thr Asp Thr Gly Phe Leu Gln Thr Leu Gly His Asn Leu
385                 390                 395                 400 ttt ggc atc tac cag aaa tat cca gtg aaa tat gga gaa gga aag tgt    1248
Phe Gly Ile Tyr Gln Lys Tyr Pro Val Lys Tyr Gly Glu Gly Lys Cys
                405                 410                 415 tgg act gac aac ggc ccg gtg atc cct gtg gtc tat gat ttt ggc gac    1296
Trp Thr Asp Asn Gly Pro Val Ile Pro Val Val Tyr Asp Phe Gly Asp
            420                 425                 430 gcc cag aaa aca gca tct tat tac tca ccc tat ggc cag cgg gaa ttc    1344
Ala Gln Lys Thr Ala Ser Tyr Tyr Ser Pro Tyr Gly Gln Arg Glu Phe
        435                 440                 445 act gcg gga ttt gtt cag ttc agg gta ttt aat aac gag aga gca gcc    1392
```

```
Thr Ala Gly Phe Val Gln Phe Arg Val Phe Asn Asn Glu Arg Ala Ala
        450                 455                 460 aac gcc ttg tgt gct gga atg agg gtc acc gga tgt aac act gag cac      1440
Asn Ala Leu Cys Ala Gly Met Arg Val Thr Gly Cys Asn Thr Glu His
465                 470                 475                 480 cac tgc att ggt gga gga gga tac ttt cca gag gcc agt ccc cag cag      1488
His Cys Ile Gly Gly Gly Gly Tyr Phe Pro Glu Ala Ser Pro Gln Gln
                485                 490                 495 tgt gga gat ttt tct ggt ttt gat tgg agt gga tat gga act cat gtt      1536
Cys Gly Asp Phe Ser Gly Phe Asp Trp Ser Gly Tyr Gly Thr His Val
            500                 505                 510 ggt tac agc agc agc cgt gag ata act gag gca gct gtg ctt cta ttc      1584
Gly Tyr Ser Ser Ser Arg Glu Ile Thr Glu Ala Ala Val Leu Leu Phe
        515                 520                 525 tat cgt tga                                                           1593
Tyr Arg
    530

<210> SEQ ID NO 22
<211> LENGTH: 530
<212> TYPE: PRT
<213> ORGANISM: Artificial Sequence
<220> FEATURE:
<223> OTHER INFORMATION: Synthetic Construct

<400> SEQUENCE: 22

Met Gly Trp Ser Ser Ile Ile Leu Phe Leu Val Ala Thr Thr Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Phe Ser Phe
        35                  40                  45

Thr Thr Tyr Trp Ile Thr Trp Val Lys Gln Arg Pro Gly Gln Gly Leu
    50                  55                  60

Glu Trp Ile Gly Met Ile His Pro Ser Asp Ser Glu Thr Arg Leu Ser
65                  70                  75                  80

Gln Thr Phe Lys Asp Lys Ala Thr Leu Thr Val Asp Lys Ser Ser Asn
                85                  90                  95

Thr Ala Tyr Met Gln Phe Ser Ser Pro Thr Ser Glu Asp Ser Ala Val
            100                 105                 110

Tyr Tyr Cys Val Arg Asp Phe Asp Val Trp Gly Ala Gly Thr Thr Val
        115                 120                 125

Thr Val Ser Ser Ala Lys Thr Thr Pro Pro Ser Val Tyr Pro Leu Ala
    130                 135                 140

Pro Gly Ser Ala Ala Gln Thr Asn Ser Met Val Thr Leu Gly Cys Leu
145                 150                 155                 160

Val Lys Gly Tyr Phe Pro Glu Pro Val Thr Val Thr Trp Asn Ser Gly
                165                 170                 175

Ser Leu Ser Ser Gly Val His Thr Phe Pro Ala Val Leu Gln Ser Asp
            180                 185                 190

Leu Tyr Thr Leu Ser Ser Ser Val Thr Val Pro Ser Ser Thr Trp Pro
        195                 200                 205

Ser Glu Thr Val Thr Cys Asn Val Ala His Pro Ala Ser Ser Thr Lys
    210                 215                 220

Val Asp Lys Lys Ile Val Pro Arg Asp Cys Gly Thr Asp Glu Ala Asn
225                 230                 235                 240

Thr Tyr Phe Lys Glu Trp Thr Cys Ser Ser Ser Pro Ser Leu Pro Arg
```

245                 250                 255
Ser Cys Lys Glu Ile Lys Asp Glu Cys Pro Ser Ala Phe Asp Gly Leu
            260                 265                 270

Tyr Phe Leu Arg Thr Glu Asn Gly Val Ile Tyr Gln Thr Phe Cys Asp
        275                 280                 285

Met Thr Ser Gly Gly Gly Trp Thr Leu Val Ala Ser Val His Glu
    290                 295                 300

Asn Asp Met Arg Gly Lys Cys Thr Val Gly Asp Arg Trp Ser Ser Gln
305                 310                 315                 320

Gln Gly Ser Lys Ala Asp Tyr Pro Glu Gly Asp Gly Asn Trp Ala Asn
                325                 330                 335

Tyr Asn Thr Phe Gly Ser Ala Glu Ala Thr Ser Asp Asp Tyr Lys
            340                 345                 350

Asn Pro Gly Tyr Tyr Asp Ile Gln Ala Lys Asp Leu Gly Ile Trp His
        355                 360                 365

Val Pro Asn Lys Ser Pro Met Gln His Trp Arg Asn Ser Ala Leu Leu
    370                 375                 380

Arg Tyr Arg Thr Asp Thr Gly Phe Leu Gln Thr Leu Gly His Asn Leu
385                 390                 395                 400

Phe Gly Ile Tyr Gln Lys Tyr Pro Val Lys Tyr Gly Glu Gly Lys Cys
                405                 410                 415

Trp Thr Asp Asn Gly Pro Val Ile Pro Val Val Tyr Asp Phe Gly Asp
            420                 425                 430

Ala Gln Lys Thr Ala Ser Tyr Tyr Ser Pro Tyr Gly Gln Arg Glu Phe
        435                 440                 445

Thr Ala Gly Phe Val Gln Phe Arg Val Phe Asn Asn Glu Arg Ala Ala
    450                 455                 460

Asn Ala Leu Cys Ala Gly Met Arg Val Thr Gly Cys Asn Thr Glu His
465                 470                 475                 480

His Cys Ile Gly Gly Gly Gly Tyr Phe Pro Glu Ala Ser Pro Gln Gln
                485                 490                 495

Cys Gly Asp Phe Ser Gly Phe Asp Trp Ser Gly Tyr Gly Thr His Val
            500                 505                 510

Gly Tyr Ser Ser Ser Arg Glu Ile Thr Glu Ala Ala Val Leu Leu Phe
        515                 520                 525

Tyr Arg
    530

<210> SEQ ID NO 23
<211> LENGTH: 21
<212> TYPE: RNA
<213> ORGANISM: Artificial Sequence
<220> FEATURE:
<223> OTHER INFORMATION: H1097, sense

<400> SEQUENCE: 23
gaucuuugac ggucagucug g                                            21

<210> SEQ ID NO 24
<211> LENGTH: 21
<212> TYPE: RNA
<213> ORGANISM: Artificial Sequence
<220> FEATURE:
<223> OTHER INFORMATION: H1097, antisense

<400> SEQUENCE: 24
agacugaccg ucaaagaucg c                                            21

```
<210> SEQ ID NO 25
<211> LENGTH: 21
<212> TYPE: RNA
<213> ORGANISM: Artificial Sequence
<220> FEATURE:
<223> OTHER INFORMATION: H2674, sense

<400> SEQUENCE: 25
ccuauagccg uacagacuac a                                              21

<210> SEQ ID NO 26
<211> LENGTH: 21
<212> TYPE: RNA
<213> ORGANISM: Artificial Sequence
<220> FEATURE:
<223> OTHER INFORMATION: H2674, antisense

<400> SEQUENCE: 26
uagucuguac ggcuauaggg c                                              21

<210> SEQ ID NO 27
<211> LENGTH: 21
<212> TYPE: RNA
<213> ORGANISM: Artificial Sequence
<220> FEATURE:
<223> OTHER INFORMATION: H3671, sense

<400> SEQUENCE: 27
gcaagucggg auacuuucag u                                              21

<210> SEQ ID NO 28
<211> LENGTH: 21
<212> TYPE: RNA
<213> ORGANISM: Artificial Sequence
<220> FEATURE:
<223> OTHER INFORMATION: H3671, antisense

<400> SEQUENCE: 28
ugaaaguauc ccgacuugca c                                              21

<210> SEQ ID NO 29
<211> LENGTH: 9156
<212> TYPE: DNA
<213> ORGANISM: Homo sapiens
<220> FEATURE:
<221> NAME/KEY: CDS
<222> LOCATION: (69)..(4214)

<400> SEQUENCE: 29
ccgctgcccg ctgcccgctg ccctcgcccc gcgcgccggg catgtgagcg cgggcgggcg    60 ccgtcacc atg gcc tcg ccg cgc gcc tcg cgg tgg ccg ccg ccg ctc ctg   110
         Met Ala Ser Pro Arg Ala Ser Arg Trp Pro Pro Pro Leu Leu
         1               5                   10 ctg ctg ttg ctg ccg ctg ctg ctg ccg ccg gcg gcc ccc ggg acg        158
Leu Leu Leu Leu Pro Leu Leu Leu Pro Pro Ala Ala Pro Gly Thr
 15                  20                  25                  30 cgg gac ccg ccg cct tcc ccg gct cgc cgc gcg ctg agc ctg gcg ccc    206
Arg Asp Pro Pro Pro Ser Pro Ala Arg Arg Ala Leu Ser Leu Ala Pro
                 35                  40                  45 ctc gcg gga gcg ggg ctg gag ctg cag ctg gag cgc cgc ccg gag cgc    254
Leu Ala Gly Ala Gly Leu Glu Leu Gln Leu Glu Arg Arg Pro Glu Arg
             50                  55                  60 gag ccg ccg ccc acg ccg ccc cgg gag cgc cgc ggg ccc gcg acc ccc    302
```

|   |   |   |   |   |   |   |   |   |   |   |   |   |   |
|---|---|---|---|---|---|---|---|---|---|---|---|---|---|
| Glu | Pro | Pro | Thr | Pro | Pro | Arg | Glu | Arg | Gly | Pro | Ala | Thr | Pro |
|     |     | 65  |     |     |     | 70  |     |     |     | 75  |     |     |     |

```
ggc ccc agc tac agg gcc cct gag cca ggc gcc gcg aca cag cgg gga      350
Gly Pro Ser Tyr Arg Ala Pro Glu Pro Gly Ala Ala Thr Gln Arg Gly
 80              85                  90 ccc tcc ggc cgg gcc ccc aga ggc ggg agc gcg gat gct gcc tgg aaa      398
Pro Ser Gly Arg Ala Pro Arg Gly Gly Ser Ala Asp Ala Ala Trp Lys
 95                  100                 105                 110 cat tgg cca gaa agt aac act gag gcc cat gta gaa aac atc acc ttc      446
His Trp Pro Glu Ser Asn Thr Glu Ala His Val Glu Asn Ile Thr Phe
                 115                 120                 125 tat cag aat caa gag gac ttt tca aca gtg tcc tcc aaa gag ggc gtg      494
Tyr Gln Asn Gln Glu Asp Phe Ser Thr Val Ser Ser Lys Glu Gly Val
         130                 135                 140 atg gtt cag acc tct ggg aag agc cat gct gct tcg gat gct cca gaa      542
Met Val Gln Thr Ser Gly Lys Ser His Ala Ala Ser Asp Ala Pro Glu
             145                 150                 155 aac ctc act cta ctc gct gaa aca gca gat gct aga gga agg agc ggc      590
Asn Leu Thr Leu Leu Ala Glu Thr Ala Asp Ala Arg Gly Arg Ser Gly
                 160                 165                 170 tct tca agt aga aca aac ttc acc att ttg cct gtt ggg tac tca ctg      638
Ser Ser Ser Arg Thr Asn Phe Thr Ile Leu Pro Val Gly Tyr Ser Leu
175                 180                 185                 190 gag ata gca aca gct ctg act tcc cag agt ggc aac tta gcc tca gaa      686
Glu Ile Ala Thr Ala Leu Thr Ser Gln Ser Gly Asn Leu Ala Ser Glu
             195                 200                 205 agt ctt cac ctg cca tcc agc agt tca gag ttc gat gaa aga att gcc      734
Ser Leu His Leu Pro Ser Ser Ser Ser Glu Phe Asp Glu Arg Ile Ala
                 210                 215                 220 gct ttt caa aca aag agt gga aca gcc tcg gag atg gga aca gag agg      782
Ala Phe Gln Thr Lys Ser Gly Thr Ala Ser Glu Met Gly Thr Glu Arg
         225                 230                 235 gcg atg ggg ctg tca gaa gaa tgg act gtg cac agc caa gag gcc acc      830
Ala Met Gly Leu Ser Glu Glu Trp Thr Val His Ser Gln Glu Ala Thr
240                 245                 250 act tcg gct tgg agc ccg tcc ttt ctt cct gct ttg gag atg gga gag      878
Thr Ser Ala Trp Ser Pro Ser Phe Leu Pro Ala Leu Glu Met Gly Glu
255                 260                 265                 270 ctg acc acg cct tct agg aag aga aat tcc tca gga cca gat ctc tcc      926
Leu Thr Thr Pro Ser Arg Lys Arg Asn Ser Ser Gly Pro Asp Leu Ser
             275                 280                 285 tgg ctg cat ttc tac agg aca gca gct tcc tct cct ctc tta gac ctt      974
Trp Leu His Phe Tyr Arg Thr Ala Ala Ser Ser Pro Leu Leu Asp Leu
                 290                 295                 300 tcc tca tct tct gaa agt aca gag aag ctt aac aac tcc act ggc ctc     1022
Ser Ser Ser Ser Glu Ser Thr Glu Lys Leu Asn Asn Ser Thr Gly Leu
                 305                 310                 315 cag agc tcc tca gtc agt caa aca aag aca atg cat gtt gcc acc gtg     1070
Gln Ser Ser Ser Val Ser Gln Thr Lys Thr Met His Val Ala Thr Val
         320                 325                 330 ttc act gat ggt ggc ccg aga acg ctg cga tct ttg acg gtc agt ctg     1118
Phe Thr Asp Gly Gly Pro Arg Thr Leu Arg Ser Leu Thr Val Ser Leu
335                 340                 345                 350 gga cct gtg agc aag aca gaa ggc ttc ccc aag gac tcc aga att gcc     1166
Gly Pro Val Ser Lys Thr Glu Gly Phe Pro Lys Asp Ser Arg Ile Ala
             355                 360                 365 acg act tca tcc tca gtc ctt ctt tca ccc tct gca gtg gaa tcg aga     1214
Thr Thr Ser Ser Ser Val Leu Leu Ser Pro Ser Ala Val Glu Ser Arg
                 370                 375                 380
```

```
aga aac agt aga gta act ggg aat cca ggg gat gag gaa ttc att gaa        1262
Arg Asn Ser Arg Val Thr Gly Asn Pro Gly Asp Glu Glu Phe Ile Glu
            385                 390                 395 cca tcc aca gaa aat gaa ttt gga ctt acg tct ttg cgt tgg caa aat        1310
Pro Ser Thr Glu Asn Glu Phe Gly Leu Thr Ser Leu Arg Trp Gln Asn
400                 405                 410 gat tcc cca acc ttt gga gaa cat cag ctt gcc agc agc tct gag gtg        1358
Asp Ser Pro Thr Phe Gly Glu His Gln Leu Ala Ser Ser Ser Glu Val
415                 420                 425                 430 caa aat gga agt ccc atg tct cag act gag act gtg tct agg tca gtc        1406
Gln Asn Gly Ser Pro Met Ser Gln Thr Glu Thr Val Ser Arg Ser Val
                435                 440                 445 gca ccc atg aga ggt gga gag atc act gca cac tgg ctc ttg acc aac        1454
Ala Pro Met Arg Gly Gly Glu Ile Thr Ala His Trp Leu Leu Thr Asn
    450                 455                 460 agc aca aca tct gca gat gtg aca gga agc tct gct tca tat cct gaa        1502
Ser Thr Thr Ser Ala Asp Val Thr Gly Ser Ser Ala Ser Tyr Pro Glu
                465                 470                 475 ggt gtg aat gct tca gtg ttg acc cag ttc tca gac tct act gta cag        1550
Gly Val Asn Ala Ser Val Leu Thr Gln Phe Ser Asp Ser Thr Val Gln
480                 485                 490 tct gga gga agt cac aca gca ttg gga gat agg agt tat tca gag tct        1598
Ser Gly Gly Ser His Thr Ala Leu Gly Asp Arg Ser Tyr Ser Glu Ser
495                 500                 505                 510 tca tct aca tct tcc tcg gaa agc ttg aat tca tca gca cca cgt gga        1646
Ser Ser Thr Ser Ser Ser Glu Ser Leu Asn Ser Ser Ala Pro Arg Gly
                515                 520                 525 gaa cgt tcg atc gct ggg att agc tac ggt caa gtg cgt ggc aca gct        1694
Glu Arg Ser Ile Ala Gly Ile Ser Tyr Gly Gln Val Arg Gly Thr Ala
                530                 535                 540 att gaa caa agg act tcc agc gac cac aca gac cac acc tac ctg tca        1742
Ile Glu Gln Arg Thr Ser Ser Asp His Thr Asp His Thr Tyr Leu Ser
            545                 550                 555 tct act ttc acc aaa gga gaa cgg gcg tta ctg tcc att aca gat aac        1790
Ser Thr Phe Thr Lys Gly Glu Arg Ala Leu Leu Ser Ile Thr Asp Asn
560                 565                 570 agt tca tcc tca gac att gtg gag agc tca act tct tat att aaa atc        1838
Ser Ser Ser Ser Asp Ile Val Glu Ser Ser Thr Ser Tyr Ile Lys Ile
575                 580                 585                 590 tca aac tct tca cat tca gag tat tcc tcc ttt ttt cat gct cag act        1886
Ser Asn Ser Ser His Ser Glu Tyr Ser Ser Phe Phe His Ala Gln Thr
                595                 600                 605 gag aga agt aac atc tca tcc tat gac ggg gaa tat gct cag cct tct        1934
Glu Arg Ser Asn Ile Ser Ser Tyr Asp Gly Glu Tyr Ala Gln Pro Ser
                610                 615                 620 act gag tcg cca gtt ctg cat aca tcc aac ctt ccg tcc tac aca ccc        1982
Thr Glu Ser Pro Val Leu His Thr Ser Asn Leu Pro Ser Tyr Thr Pro
            625                 630                 635 acc att aat atg ccg aac act tcg gtt gtt ctg gac act gat gct gag        2030
Thr Ile Asn Met Pro Asn Thr Ser Val Val Leu Asp Thr Asp Ala Glu
640                 645                 650 ttt gtt agt gac tcc tcc tcc tct tcc tcc tcc tct tct tct                2078
Phe Val Ser Asp Ser Ser Ser Ser Ser Ser Ser Ser Ser Ser Ser
655                 660                 665                 670 tct tca ggg cct cct ttg cct ctg ccc tct gtg tca caa tcc cac cat        2126
Ser Ser Gly Pro Pro Leu Pro Leu Pro Ser Val Ser Gln Ser His His
                675                 680                 685 tta ttt tca tca att tta cca tca acc agg gcc tct gtg cat cta cta        2174
Leu Phe Ser Ser Ile Leu Pro Ser Thr Arg Ala Ser Val His Leu Leu
            690                 695                 700
```

```
aag tct acc tct gat gca tcc aca cca tgg tct tcc tca cca tca cct      2222
Lys Ser Thr Ser Asp Ala Ser Thr Pro Trp Ser Ser Ser Pro Ser Pro
            705                 710                 715 tta cca gta tcc tta acg aca tct aca tct gcc cca ctt tct gtc tca      2270
Leu Pro Val Ser Leu Thr Thr Ser Thr Ser Ala Pro Leu Ser Val Ser
        720                 725                 730 caa aca acc ttg cca cag tca tct tct acc cct gtc ctg ccc agg gca      2318
Gln Thr Thr Leu Pro Gln Ser Ser Ser Thr Pro Val Leu Pro Arg Ala
735                 740                 745                 750 agg gag act cct gtg act tca ttt cag aca tca aca atg aca tca ttc      2366
Arg Glu Thr Pro Val Thr Ser Phe Gln Thr Ser Thr Met Thr Ser Phe
                755                 760                 765 atg aca atg ctc cat agt agt caa act gca gac ctt aag agc cag agc      2414
Met Thr Met Leu His Ser Ser Gln Thr Ala Asp Leu Lys Ser Gln Ser
            770                 775                 780 acc cca cac caa gag aaa gtc att aca gaa tca aag tca cca agc ctg      2462
Thr Pro His Gln Glu Lys Val Ile Thr Glu Ser Lys Ser Pro Ser Leu
        785                 790                 795 gtg tct ctg ccc aca gag tcc acc aaa gct gta aca aca aac tct cct      2510
Val Ser Leu Pro Thr Glu Ser Thr Lys Ala Val Thr Thr Asn Ser Pro
    800                 805                 810 ttg cct cca tcc tta aca gag tcc tcc aca gag caa acc ctt cca gcc      2558
Leu Pro Pro Ser Leu Thr Glu Ser Ser Thr Glu Gln Thr Leu Pro Ala
815                 820                 825                 830 aca agc acc aac tta gca caa atg tct cca act ttc aca act acc att      2606
Thr Ser Thr Asn Leu Ala Gln Met Ser Pro Thr Phe Thr Thr Thr Ile
                835                 840                 845 ctg aag acc tct cag cct ctt atg acc act cct ggc acc ctg tca agc      2654
Leu Lys Thr Ser Gln Pro Leu Met Thr Thr Pro Gly Thr Leu Ser Ser
            850                 855                 860 aca gca tct ctg gtc act ggc cct ata gcc gta cag act aca gct gga      2702
Thr Ala Ser Leu Val Thr Gly Pro Ile Ala Val Gln Thr Thr Ala Gly
        865                 870                 875 aaa cag ctc tcg ctg acc cat cct gaa ata cta gtt cct caa atc tca      2750
Lys Gln Leu Ser Leu Thr His Pro Glu Ile Leu Val Pro Gln Ile Ser
    880                 885                 890 aca gaa ggt ggc atc agc aca gaa agg aac cga gtg att gtg gat gct      2798
Thr Glu Gly Gly Ile Ser Thr Glu Arg Asn Arg Val Ile Val Asp Ala
895                 900                 905                 910 acc act gga ttg atc cct ttg acc agt gta ccc aca tca gca aaa gaa      2846
Thr Thr Gly Leu Ile Pro Leu Thr Ser Val Pro Thr Ser Ala Lys Glu
                915                 920                 925 atg acc aca aag ctt ggc gtt aca gca gag tac agc cca gct tca cgt      2894
Met Thr Thr Lys Leu Gly Val Thr Ala Glu Tyr Ser Pro Ala Ser Arg
            930                 935                 940 tcc ctc gga aca tct cct tct ccc caa acc aca gtt gtt tcc acg gct      2942
Ser Leu Gly Thr Ser Pro Ser Pro Gln Thr Thr Val Val Ser Thr Ala
        945                 950                 955 gaa gac ttg gct ccc aaa tct gcc acc ttt gct gtt cag agc agc aca      2990
Glu Asp Leu Ala Pro Lys Ser Ala Thr Phe Ala Val Gln Ser Ser Thr
    960                 965                 970 cag tca cca aca aca gtg tcc tct tca gcc tca gtc aac agc tgt gct      3038
Gln Ser Pro Thr Thr Val Ser Ser Ser Ala Ser Val Asn Ser Cys Ala
975                 980                 985                 990 gtg aac cct tgt ctt cac aat ggc gaa tgc gtc gca gac aac acc agc      3086
Val Asn Pro Cys Leu His Asn Gly Glu Cys Val Ala Asp Asn Thr Ser
                995                 1000                1005 cgt ggc tac cac tgc agg tgc ccg cct tcc tgg caa ggg gat gat           3131
Arg Gly Tyr His Cys Arg Cys Pro Pro Ser Trp Gln Gly Asp Asp
```

|  |  |  |  |  |  |  |  |  |  |  |  |  |  |  |
|---|---|---|---|---|---|---|---|---|---|---|---|---|---|---|
|  | 1010 |  |  |  | 1015 |  |  |  | 1020 |  |  |  |  |  |
| tgc | agt | gtg | gat | gtg | aat | gag | tgc | ctg | tcg | aac | ccc | tgc | cca | tcc | 3176 |
| Cys | Ser | Val | Asp | Val | Asn | Glu | Cys | Leu | Ser | Asn | Pro | Cys | Pro | Ser |  |
|  |  | 1025 |  |  |  | 1030 |  |  |  | 1035 |  |  |  |  |  |
| aca | gcc | atg | tgc | aac | aat | act | cag | gga | tcc | ttt | atc | tgc | aaa | tgc | 3221 |
| Thr | Ala | Met | Cys | Asn | Asn | Thr | Gln | Gly | Ser | Phe | Ile | Cys | Lys | Cys |  |
|  |  | 1040 |  |  |  | 1045 |  |  |  | 1050 |  |  |  |  |  |
| ccg | gtt | ggg | tac | cag | ttg | gaa | aaa | ggg | ata | tgc | aat | ttg | gtt | aga | 3266 |
| Pro | Val | Gly | Tyr | Gln | Leu | Glu | Lys | Gly | Ile | Cys | Asn | Leu | Val | Arg |  |
|  |  | 1055 |  |  |  | 1060 |  |  |  | 1065 |  |  |  |  |  |
| acc | ttc | gtg | aca | gag | ttt | aaa | tta | aag | aga | act | ttt | ctt | aat | aca | 3311 |
| Thr | Phe | Val | Thr | Glu | Phe | Lys | Leu | Lys | Arg | Thr | Phe | Leu | Asn | Thr |  |
|  |  | 1070 |  |  |  | 1075 |  |  |  | 1080 |  |  |  |  |  |
| act | gtg | gaa | aaa | cat | tca | gac | cta | caa | gaa | gtt | gaa | aat | gag | atc | 3356 |
| Thr | Val | Glu | Lys | His | Ser | Asp | Leu | Gln | Glu | Val | Glu | Asn | Glu | Ile |  |
|  |  | 1085 |  |  |  | 1090 |  |  |  | 1095 |  |  |  |  |  |
| acc | aaa | acg | tta | aat | atg | tgt | ttt | tca | gcg | tta | cct | agt | tac | atc | 3401 |
| Thr | Lys | Thr | Leu | Asn | Met | Cys | Phe | Ser | Ala | Leu | Pro | Ser | Tyr | Ile |  |
|  |  | 1100 |  |  |  | 1105 |  |  |  | 1110 |  |  |  |  |  |
| cga | tct | aca | gtt | cac | gcc | tct | agg | gag | tcc | aac | gcg | gtg | gtg | atc | 3446 |
| Arg | Ser | Thr | Val | His | Ala | Ser | Arg | Glu | Ser | Asn | Ala | Val | Val | Ile |  |
|  |  | 1115 |  |  |  | 1120 |  |  |  | 1125 |  |  |  |  |  |
| tca | ctg | caa | aca | acc | ttt | tcc | ctg | gcc | tcc | aat | gtg | acg | cta | ttt | 3491 |
| Ser | Leu | Gln | Thr | Thr | Phe | Ser | Leu | Ala | Ser | Asn | Val | Thr | Leu | Phe |  |
|  |  | 1130 |  |  |  | 1135 |  |  |  | 1140 |  |  |  |  |  |
| gac | ctg | gct | gat | agg | atg | cag | aaa | tgt | gtc | aac | tcc | tgc | aag | tcc | 3536 |
| Asp | Leu | Ala | Asp | Arg | Met | Gln | Lys | Cys | Val | Asn | Ser | Cys | Lys | Ser |  |
|  |  | 1145 |  |  |  | 1150 |  |  |  | 1155 |  |  |  |  |  |
| tct | gct | gag | gtc | tgc | cag | ctc | ttg | gga | tct | cag | agg | cgg | atc | ttt | 3581 |
| Ser | Ala | Glu | Val | Cys | Gln | Leu | Leu | Gly | Ser | Gln | Arg | Arg | Ile | Phe |  |
|  |  | 1160 |  |  |  | 1165 |  |  |  | 1170 |  |  |  |  |  |
| aga | gcg | ggc | agc | ttg | tgc | aag | cgg | aag | agt | ccc | gaa | tgt | gac | aaa | 3626 |
| Arg | Ala | Gly | Ser | Leu | Cys | Lys | Arg | Lys | Ser | Pro | Glu | Cys | Asp | Lys |  |
|  |  | 1175 |  |  |  | 1180 |  |  |  | 1185 |  |  |  |  |  |
| gac | acc | tcc | atc | tgc | act | gac | ctg | gac | ggc | gtt | gcc | ctg | tgc | cag | 3671 |
| Asp | Thr | Ser | Ile | Cys | Thr | Asp | Leu | Asp | Gly | Val | Ala | Leu | Cys | Gln |  |
|  |  | 1190 |  |  |  | 1195 |  |  |  | 1200 |  |  |  |  |  |
| tgc | aag | tcg | gga | tac | ttt | cag | ttc | aac | aag | atg | gac | cac | tcc | tgc | 3716 |
| Cys | Lys | Ser | Gly | Tyr | Phe | Gln | Phe | Asn | Lys | Met | Asp | His | Ser | Cys |  |
|  |  | 1205 |  |  |  | 1210 |  |  |  | 1215 |  |  |  |  |  |
| cga | gca | tgt | gaa | gat | gga | tat | agg | ctt | gaa | aat | gaa | acc | tgc | atg | 3761 |
| Arg | Ala | Cys | Glu | Asp | Gly | Tyr | Arg | Leu | Glu | Asn | Glu | Thr | Cys | Met |  |
|  |  | 1220 |  |  |  | 1225 |  |  |  | 1230 |  |  |  |  |  |
| agt | tgc | cca | ttt | ggc | ctt | ggt | ggt | ctc | aac | tgt | gga | aac | ccc | tat | 3806 |
| Ser | Cys | Pro | Phe | Gly | Leu | Gly | Gly | Leu | Asn | Cys | Gly | Asn | Pro | Tyr |  |
|  |  | 1235 |  |  |  | 1240 |  |  |  | 1245 |  |  |  |  |  |
| cag | ctt | atc | act | gtg | gtg | atc | gca | gcc | gcg | gga | ggt | ggg | ctc | ctg | 3851 |
| Gln | Leu | Ile | Thr | Val | Val | Ile | Ala | Ala | Ala | Gly | Gly | Gly | Leu | Leu |  |
|  |  | 1250 |  |  |  | 1255 |  |  |  | 1260 |  |  |  |  |  |
| ctc | atc | cta | ggc | atc | gca | ctg | att | gtt | acc | tgt | tgc | aga | aag | aat | 3896 |
| Leu | Ile | Leu | Gly | Ile | Ala | Leu | Ile | Val | Thr | Cys | Cys | Arg | Lys | Asn |  |
|  |  | 1265 |  |  |  | 1270 |  |  |  | 1275 |  |  |  |  |  |
| aaa | aat | gac | ata | agc | aaa | ctc | atc | ttc | aaa | agt | gga | gat | ttc | caa | 3941 |
| Lys | Asn | Asp | Ile | Ser | Lys | Leu | Ile | Phe | Lys | Ser | Gly | Asp | Phe | Gln |  |
|  |  | 1280 |  |  |  | 1285 |  |  |  | 1290 |  |  |  |  |  |
| atg | tcc | ccg | tat | gct | gaa | tac | ccc | aaa | aat | cct | cgc | tca | caa | gaa | 3986 |
| Met | Ser | Pro | Tyr | Ala | Glu | Tyr | Pro | Lys | Asn | Pro | Arg | Ser | Gln | Glu |  |
|  |  | 1295 |  |  |  | 1300 |  |  |  | 1305 |  |  |  |  |  |
| tgg | ggc | cga | gaa | gct | att | gaa | atg | cat | gag | aat | gga | agt | acc | aaa | 4031 |

|     |     |     |     |     |     |     |     |     |     |     |     |     |
| --- | --- | --- | --- | --- | --- | --- | --- | --- | --- | --- | --- | --- |
| Trp | Gly | Arg | Glu | Ala | Ile | Glu | Met | His | Glu | Asn | Gly | Ser | Thr | Lys |
|     |     |     | 1310 |     |     |     |     | 1315 |     |     |     | 1320 |

```
aac ctc ctc cag atg acg gat gtg tac tac tcg cct aca agt gta      4076
Asn Leu Leu Gln Met Thr Asp Val Tyr Tyr Ser Pro Thr Ser Val
        1325                1330                1335 agg aat cca gaa ctt gaa cga aac gga ctc tac ccg gcc tac act      4121
Arg Asn Pro Glu Leu Glu Arg Asn Gly Leu Tyr Pro Ala Tyr Thr
        1340                1345                1350 gga ctg cca gga tca cgg cat tct tgc att ttc ccc gga cag tat      4166
Gly Leu Pro Gly Ser Arg His Ser Cys Ile Phe Pro Gly Gln Tyr
        1355                1360                1365 aac ccg tct ttc atc agt gat gaa agc aga aga aga gac tac ttt      4211
Asn Pro Ser Phe Ile Ser Asp Glu Ser Arg Arg Arg Asp Tyr Phe
        1370                1375                1380 taa gtccaggaga gagagggact cattgctctg agccagtcac ctgggacctc       4264
tgctcagagg accgcaccag gaggctgcgc ccaggatttg tcgggagcca cgctgagtgg  4324
caagcaggaa gagggacagg catgcggggc gtgaccacag tggaggagac aggtggatgt  4384
ggaaccacag gctgctcatt cagcaccttt gttgttactg tgaacgtgaa tgtgggccag  4444
tatcaagaga gtctctctga gtgactgcac catggcactg gcaccagggc gactattagc  4504
cagggcagac cactagactt cagtgcaggg acctggtttt cccttcgttt gcactttagt  4564
aaattgggtg ggaggtttcc ttttggatct gttttgagac tgttccagaa agaaggcttc  4624
ctttcccgag acacttccat aggcagcaat ttggtgattc atttgcagca aaatactggc  4684
ttgttaatta ttttcctgcc cagcgcctgc gtgctaaaca acagatgagg atgagcgtac  4744
cactgaagtc tgaagatgtc gccattgaac ggacagtgtt ttcatatgtt tctaggttgt  4804
cttatgctac agtttccaag ccagccccca cagtgaggaa atgtgtgagg caccgcacac  4864
aactgcaatg tgttttttaa gtcaaggtga cacatgtatt taagattttt tttttaaatc  4924
tctttgcagt taaatctcac tttttcaaac aagcctggat cagggcaaaa caacttatat  4984 ttggtttttag ctggaggctc agcaggcaga ttgcaggcag gggggcactt ttcatccatg  5044
agggcccagc ctggggcctg ggactcgatc accattgtgg aggccagagg cagctgcgta  5104
tggaggagaa atgtcaaact gaacgcaggt ttcaccactc taggaaagca gcttgttgag  5164
cccctgcagc tggatgtggt tagagggatg ggctgaatag gcaggttaga tttcctgcat  5224
caacagtgct ttgggaagct gtgtggattc ctgaggaaga acaggagcc gagatggagc   5284 cacacatgag tttgctcacc ggctactgca gcactttgta cccagaatct catgtccaca   5344
aaccccatgt aaactttcaa ccactcaaag ctgtttattc ggctgaagaa ataacttttt   5404
tttctcaccc agtcatttgt acctcttcat atggctatgt cgcaccctcc agaaacgtgg   5464
ttatacttcc agtcagtgtg ggagaactga agacttccgg ttggtcgagg aactgagggt   5524
tgaccttcgg gaaggaagtt ccactcatct tatttattat gcctgtgatg tgggtcctgc   5584
cagggagaca tccagtactc ggtgtcttta attgccacct ggggaactgt gtttattggc   5644
cttctttggg gcatcctggt tttggatgaa gtgagggaa tacagaggta aaagaattgt    5704
ctccaccctg aagcggggag tcccgcttca catttctgga aatggtgcag ccactgggga   5764
cagttctgcc ccgggcatgg ttgtttcttc aaggtcctct aaatataatc cctattctta   5824
cataatcctt ggccctgatg gttttaagca agaactcctg tgtcccatgg tctccaccac   5884
tcaccatcac cctgctgtag caagagtcct agtcagggga ggtgcatttt agtagttaca   5944
ttgcacttat ccatgagata aataaaagga gaactgtttt tatcagtgga ggctaaccta   6004
```

```
aaatttcaaa gtgtcgcctt tttgaaatct tgggcctctc tctctgtaga accaatggcc   6064
ctttgtggct cacggcctcg cacctaactg gagagttctg agctcctgca gctcacctga   6124
gcccacagac taggcttctt ggctccttcc gcagcatgcc tgctcacccc cagaacccgc   6184
agctgtggga gagccatgt agggaggcta ttcccaggca tacacttcca ctgccttcag    6244
ctgacgtcac agctgacaaa tcatctcctc tatcggagcc agaagacttc agctccacaa   6304
aatgaagtgt tctgtcctga aaacattctt gggaagaatc ccaacatcga gaaacggtg    6364 tcctgtgagt tccaacaatg cttcttgttc atgggtttct tccgtatgga gtggattaag   6424 agtgtttat tttgttgttc taactgagaa aaaaaggagg cacccacaag gttgaggtca    6484
cacagtctcc acagtttcca ggaggcgttt gggggtgggg aaggcacctc cagagcatga   6544
ggctctaagg ggacatgagt aaagcatgtc tgtgacccag tgaggaaggg agaggccagc   6604
tgcactcctg cacggggttc ctagctgcag aagggtcccg cctaggccga ggggaaacac   6664
ctgatagcag aagaggcctg gatgcacacc tggcacgccg aggctctccg cccagacaca   6724
gtgctccatg tcagccctg cacctggggt gtgtgattca cgtgcacaga tgccacaatc    6784
ctgcaccaat atcccacaga tgggggaagg tgagaggaag gggcaagtga tgtgtaactg   6844
ctcaagagat gcttaaacct ccatagagag gagccgggcg caggggcatc tgtgtgtccc   6904
gtcacacact gcagcaggga agggtggctg gctggctccc tggcatcagt ggtttggttt   6964
aagctccaga gggtcttatt gccattgtct tttcctctgc cccttgagcc agcctaaggc   7024
cctggagtct gtttctttag gcggatgaac tgacatgctc ctaccatgac caggctctgg   7084
gcaaggctcc tcacagtatc cttgagaggt gggcatggaa gtgcccattt ctcaggtaca   7144
gaaaccttca gagaggataa atagcttgcc ctgtagaagc aggactgaaa cccttgtctg   7204
cctgactccc ccagctactc tgcccactgt agcccctgc cttactgtcc tggcacaccc    7264
ctcaccatcc tgtataccat aaatatcaaa gagggcaaga gagaaagggc tttaaagata   7324
agttattttt ttaaggaacc ttaatattat ttttaagaag taaccaaatt agtgacgtga   7384
aatgcaaaaa aaaaaaaaa aaaatgctga ctacccttt gaaaatgtgc tttcagattg     7444 tttttatat gtaattctta gacacttgtc attaagaaaa tagtggctgg cttgtgctca    7504
gcaagaagca cactggcacg tggctttggt ataggaagtg gaaggcaagg acctgggttt   7564
ctgacaagtg cagtcagaca tacacatcca tctgagagct gcttgccttg ttcccgtggt   7624
aaggccatgg ctcccacata ctggaagcat attttgtga actgttttca gaattgggaa    7684
catattcagt ggaatgtctt aaacgctgac acatcttcct cctttgaggg gaagtatatt   7744
ttcagaagca gctaagacat ttagagccaa aattgctgat aggtggttca gtcaagttgg   7804
ctgatggcat ctgaggtcaa aaactaagat gtgacgattg agttcttaaa gaggtaactc   7864
ttaaagtggg cccaagggag aaggcagcat ctttggactc ctaggctgga tggctaccca   7924
agaatatgcc attgaaggat gacacctatt cagatgtgaa agttcccaga gcaggcacct   7984
ttgggtcacc caccacgtgt ggcttttggg tgcctgcatg aaactgtgtt gcccctggt    8044 gagatgcccg ggtgtcctgt aagccgattt aactctgcct gaggaagagg agctgtccac   8104
tccagttgcc cttggctaag tttagcctaa cacacagggt tttgacccat agttctaaaa   8164
tacacaaatt ttgagactac agcacttctt tggaaagagg aagaatgcaa agttcagtat   8224
ttcaatactt tgtattttac ttgaaattac ccttagtagc atctttttt tcctgtctga    8284 aagcttttgt gtggatgaga agggacattt catttcctcc cttaacaaag tgtcattctg   8344
aggttctcat gtgtgttttt ggaaatagag atactggttt tgtagagttt gcctttgggt   8404
```

```
atgtttctt tttttcttaa atctccaagg aagagaactg actaaaatag taggaacatg    8464
aaagtattaa atgccaatta atttgttgta gtaaagtatc ttcattagcg ttatactcca    8524
tcatatctgg tgtaaactgc tcacagaaaa ccctatgaaa ccaaagggg accattcagg     8584 tctaaaaagc gacaggtccg agactgggtc tgtcacctgg gcattttcaa agaggacatt    8644
ttgaagaatt tgcatattca gattttaaa atgcacttaa catacttcat tacagatttc     8704
ttgggtaggg aggatgggat aggccaggga tgggatggag tcagttctgc ctgggaaact    8764
aatccgaatc atttaccttt ctgtattaac cttggcctgt cctaaaaaga gaacgactgt    8824
ttcatcatga gttgctctga gttttgttaa tgtttgtgtt ggtggattga cggttaaatg    8884
aagcatttag ctggaatatg aactttggga gttttcatgt tgtcctggat ttctctttgt    8944
aaacctttaa accttagccc ctggttgatt gtgttaaacc cattatgaga atgttatta    9004 aagttgtatt ataattgcaa cctccactaa ttattcagta ctgtagcagc aaagtattat    9064
ttgtaagaat ttggttattt ttatacttat atccactcta agtctggcgt tctagtcagt    9124
aaaatgatgc aataaaatta atatcattt ca                                   9156
```

<210> SEQ ID NO 30
<211> LENGTH: 1381
<212> TYPE: PRT
<213> ORGANISM: Homo sapiens

<400> SEQUENCE: 30

```
Met Ala Ser Pro Arg Ala Ser Arg Trp Pro Pro Leu Leu Leu Leu
1               5                   10                  15

Leu Leu Pro Leu Leu Leu Pro Pro Ala Ala Pro Gly Thr Arg Asp
                20                  25                  30

Pro Pro Pro Ser Pro Ala Arg Arg Ala Leu Ser Leu Ala Pro Leu Ala
            35                  40                  45

Gly Ala Gly Leu Glu Leu Gln Leu Glu Arg Arg Pro Glu Arg Glu Pro
        50                  55                  60

Pro Pro Thr Pro Pro Arg Glu Arg Arg Gly Pro Ala Thr Pro Gly Pro
65                  70                  75                  80

Ser Tyr Arg Ala Pro Glu Pro Gly Ala Ala Thr Gln Arg Gly Pro Ser
                85                  90                  95

Gly Arg Ala Pro Arg Gly Gly Ser Ala Asp Ala Ala Trp Lys His Trp
            100                 105                 110

Pro Glu Ser Asn Thr Glu Ala His Val Glu Asn Ile Thr Phe Tyr Gln
        115                 120                 125

Asn Gln Glu Asp Phe Ser Thr Val Ser Ser Lys Glu Gly Val Met Val
    130                 135                 140

Gln Thr Ser Gly Lys Ser His Ala Ala Ser Asp Ala Pro Glu Asn Leu
145                 150                 155                 160

Thr Leu Leu Ala Glu Thr Ala Asp Ala Arg Gly Arg Ser Gly Ser Ser
                165                 170                 175

Ser Arg Thr Asn Phe Thr Ile Leu Pro Val Gly Tyr Ser Leu Glu Ile
            180                 185                 190

Ala Thr Ala Leu Thr Ser Gln Ser Gly Asn Leu Ala Ser Glu Ser Leu
        195                 200                 205

His Leu Pro Ser Ser Ser Glu Phe Asp Glu Arg Ile Ala Ala Phe
    210                 215                 220

Gln Thr Lys Ser Gly Thr Ala Ser Glu Met Gly Thr Glu Arg Ala Met
225                 230                 235                 240
```

```
Gly Leu Ser Glu Glu Trp Thr Val His Ser Gln Ala Thr Thr Ser
                245                 250                 255

Ala Trp Ser Pro Ser Phe Leu Pro Ala Leu Glu Met Gly Glu Leu Thr
                260                 265                 270

Thr Pro Ser Arg Lys Arg Asn Ser Ser Gly Pro Asp Leu Ser Trp Leu
                275                 280                 285

His Phe Tyr Arg Thr Ala Ala Ser Ser Pro Leu Leu Asp Leu Ser Ser
                290                 295                 300

Ser Ser Glu Ser Thr Glu Lys Leu Asn Asn Ser Thr Gly Leu Gln Ser
305                 310                 315                 320

Ser Ser Val Ser Gln Thr Lys Thr Met His Val Ala Thr Val Phe Thr
                325                 330                 335

Asp Gly Gly Pro Arg Thr Leu Arg Ser Leu Thr Val Ser Leu Gly Pro
                340                 345                 350

Val Ser Lys Thr Glu Gly Phe Pro Lys Asp Ser Arg Ile Ala Thr Thr
                355                 360                 365

Ser Ser Ser Val Leu Leu Ser Pro Ala Val Glu Ser Arg Arg Asn
                370                 375                 380

Ser Arg Val Thr Gly Asn Pro Gly Asp Glu Glu Phe Ile Glu Pro Ser
385                 390                 395                 400

Thr Glu Asn Glu Phe Gly Leu Thr Ser Leu Arg Trp Gln Asn Asp Ser
                405                 410                 415

Pro Thr Phe Gly Glu His Gln Leu Ala Ser Ser Glu Val Gln Asn
                420                 425                 430

Gly Ser Pro Met Ser Gln Thr Glu Thr Val Ser Arg Ser Val Ala Pro
                435                 440                 445

Met Arg Gly Gly Glu Ile Thr Ala His Trp Leu Leu Thr Asn Ser Thr
450                 455                 460

Thr Ser Ala Asp Val Thr Gly Ser Ser Ala Ser Tyr Pro Glu Gly Val
465                 470                 475                 480

Asn Ala Ser Val Leu Thr Gln Phe Ser Asp Ser Thr Val Gln Ser Gly
                485                 490                 495

Gly Ser His Thr Ala Leu Gly Asp Arg Ser Tyr Ser Gly Ser Ser Ser
                500                 505                 510

Thr Ser Ser Ser Glu Ser Leu Asn Ser Ser Ala Pro Arg Gly Glu Arg
                515                 520                 525

Ser Ile Ala Gly Ile Ser Tyr Gly Gln Val Arg Gly Thr Ala Ile Glu
530                 535                 540

Gln Arg Thr Ser Ser Asp His Thr Asp His Thr Tyr Leu Ser Ser Thr
545                 550                 555                 560

Phe Thr Lys Gly Glu Arg Ala Leu Leu Ser Ile Thr Asp Asn Ser Ser
                565                 570                 575

Ser Ser Asp Ile Val Glu Ser Ser Thr Ser Tyr Ile Lys Ile Ser Asn
                580                 585                 590

Ser Ser His Ser Glu Tyr Ser Ser Phe Phe His Ala Gln Thr Glu Arg
                595                 600                 605

Ser Asn Ile Ser Ser Tyr Asp Gly Glu Tyr Ala Gln Pro Ser Thr Glu
                610                 615                 620

Ser Pro Val Leu His Thr Ser Asn Leu Pro Ser Tyr Thr Pro Thr Ile
625                 630                 635                 640

Asn Met Pro Asn Thr Ser Val Val Leu Asp Thr Asp Ala Glu Phe Val
                645                 650                 655
```

```
Ser Asp Ser Ser Ser Ser Ser Ser Ser Ser Ser Ser Ser Ser
        660                 665                 670

Gly Pro Pro Leu Pro Leu Pro Ser Val Ser Gln Ser His His Leu Phe
        675                 680                 685

Ser Ser Ile Leu Pro Ser Thr Arg Ala Ser Val His Leu Leu Lys Ser
        690                 695                 700

Thr Ser Asp Ala Ser Thr Pro Trp Ser Ser Pro Ser Pro Leu Pro
705                 710                 715                 720

Val Ser Leu Thr Thr Ser Thr Ser Ala Pro Leu Ser Val Ser Gln Thr
                    725                 730                 735

Thr Leu Pro Gln Ser Ser Ser Thr Pro Val Leu Pro Arg Ala Arg Glu
            740                 745                 750

Thr Pro Val Thr Ser Phe Gln Thr Ser Thr Met Thr Ser Phe Met Thr
            755                 760                 765

Met Leu His Ser Ser Gln Thr Ala Asp Leu Lys Ser Gln Ser Thr Pro
        770                 775                 780

His Gln Glu Lys Val Ile Thr Glu Ser Lys Ser Pro Ser Leu Val Ser
785                 790                 795                 800

Leu Pro Thr Glu Ser Thr Lys Ala Val Thr Thr Asn Ser Pro Leu Pro
                805                 810                 815

Pro Ser Leu Thr Glu Ser Ser Thr Glu Gln Thr Leu Pro Ala Thr Ser
            820                 825                 830

Thr Asn Leu Ala Gln Met Ser Pro Thr Phe Thr Thr Ile Leu Lys
        835                 840                 845

Thr Ser Gln Pro Leu Met Thr Thr Pro Gly Thr Leu Ser Ser Thr Ala
    850                 855                 860

Ser Leu Val Thr Gly Pro Ile Ala Val Gln Thr Thr Ala Gly Lys Gln
865                 870                 875                 880

Leu Ser Leu Thr His Pro Glu Ile Leu Val Pro Gln Ile Ser Thr Glu
                885                 890                 895

Gly Gly Ile Ser Thr Glu Arg Asn Arg Val Ile Val Asp Ala Thr Thr
                900                 905                 910

Gly Leu Ile Pro Leu Thr Ser Val Pro Thr Ser Ala Lys Glu Met Thr
        915                 920                 925

Thr Lys Leu Gly Val Thr Ala Glu Tyr Ser Pro Ala Ser Arg Ser Leu
930                 935                 940

Gly Thr Ser Pro Ser Pro Gln Thr Thr Val Val Ser Thr Ala Glu Asp
945                 950                 955                 960

Leu Ala Pro Lys Ser Ala Thr Phe Ala Val Gln Ser Ser Thr Gln Ser
                965                 970                 975

Pro Thr Thr Val Ser Ser Ser Ala Ser Val Asn Ser Cys Ala Val Asn
            980                 985                 990

Pro Cys Leu His Asn Gly Glu Cys Val Ala Asp Asn Thr Ser Arg Gly
        995                 1000                1005

Tyr His Cys Arg Cys Pro Pro Ser Trp Gln Gly Asp Asp Cys Ser
    1010                1015                1020

Val Asp Val Asn Glu Cys Leu Ser Asn Pro Cys Pro Ser Thr Ala
    1025                1030                1035

Met Cys Asn Asn Thr Gln Gly Ser Phe Ile Cys Lys Cys Pro Val
    1040                1045                1050

Gly Tyr Gln Leu Glu Lys Gly Ile Cys Asn Leu Val Arg Thr Phe
    1055                1060                1065

Val Thr Glu Phe Lys Leu Lys Arg Thr Phe Leu Asn Thr Thr Val
```

```
                1070                1075                1080
Glu Lys His Ser Asp Leu Gln Glu Val Glu Asn Glu Ile Thr Lys
        1085                1090                1095

Thr Leu Asn Met Cys Phe Ser Ala Leu Pro Ser Tyr Ile Arg Ser
        1100                1105                1110

Thr Val His Ala Ser Arg Glu Ser Asn Ala Val Val Ile Ser Leu
        1115                1120                1125

Gln Thr Thr Phe Ser Leu Ala Ser Asn Val Thr Leu Phe Asp Leu
        1130                1135                1140

Ala Asp Arg Met Gln Lys Cys Val Asn Ser Cys Lys Ser Ser Ala
        1145                1150                1155

Glu Val Cys Gln Leu Leu Gly Ser Gln Arg Arg Ile Phe Arg Ala
        1160                1165                1170

Gly Ser Leu Cys Lys Arg Lys Ser Pro Glu Cys Asp Lys Asp Thr
        1175                1180                1185

Ser Ile Cys Thr Asp Leu Asp Gly Val Ala Leu Cys Gln Cys Lys
        1190                1195                1200

Ser Gly Tyr Phe Gln Phe Asn Lys Met Asp His Ser Cys Arg Ala
        1205                1210                1215

Cys Glu Asp Gly Tyr Arg Leu Glu Asn Glu Thr Cys Met Ser Cys
        1220                1225                1230

Pro Phe Gly Leu Gly Gly Leu Asn Cys Gly Asn Pro Tyr Gln Leu
        1235                1240                1245

Ile Thr Val Val Ile Ala Ala Ala Gly Gly Gly Leu Leu Leu Ile
        1250                1255                1260

Leu Gly Ile Ala Leu Ile Val Thr Cys Cys Arg Lys Asn Lys Asn
        1265                1270                1275

Asp Ile Ser Lys Leu Ile Phe Lys Ser Gly Asp Phe Gln Met Ser
        1280                1285                1290

Pro Tyr Ala Glu Tyr Pro Lys Asn Pro Arg Ser Gln Glu Trp Gly
        1295                1300                1305

Arg Glu Ala Ile Glu Met His Glu Asn Gly Ser Thr Lys Asn Leu
        1310                1315                1320

Leu Gln Met Thr Asp Val Tyr Tyr Ser Pro Thr Ser Val Arg Asn
        1325                1330                1335

Pro Glu Leu Glu Arg Asn Gly Leu Tyr Pro Ala Tyr Thr Gly Leu
        1340                1345                1350

Pro Gly Ser Arg His Ser Cys Ile Phe Pro Gly Gln Tyr Asn Pro
        1355                1360                1365

Ser Phe Ile Ser Asp Glu Ser Arg Arg Arg Asp Tyr Phe
        1370                1375                1380

<210> SEQ ID NO 31
<211> LENGTH: 1012
<212> TYPE: PRT
<213> ORGANISM: Homo sapiens

<400> SEQUENCE: 31

Met Ala Ser Pro Arg Ala Ser Arg Trp Pro Pro Leu Leu Leu Leu
1               5                   10                  15

Leu Leu Pro Leu Leu Leu Leu Pro Ala Ala Pro Gly Thr Arg Asp
                20                  25                  30

Pro Pro Pro Ser Pro Ala Arg Arg Ala Leu Ser Leu Ala Pro Leu Ala
                35                  40                  45
```

```
Gly Ala Gly Leu Glu Leu Gln Leu Glu Arg Arg Pro Glu Arg Glu Pro
     50              55                  60
Pro Pro Thr Pro Pro Arg Glu Arg Arg Gly Pro Ala Thr Pro Gly Pro
 65              70                  75                  80
Ser Tyr Arg Ala Pro Glu Pro Gly Ala Ala Thr Gln Arg Gly Pro Ser
                 85                  90                  95
Gly Arg Ala Pro Arg Gly Gly Ser Ala Asp Ala Ala Trp Lys His Trp
                100                 105                 110
Pro Glu Ser Asn Thr Glu Ala His Val Glu Asn Ile Thr Phe Tyr Gln
                115                 120                 125
Asn Gln Glu Asp Phe Ser Thr Val Ser Ser Lys Glu Gly Val Met Val
            130                 135                 140
Gln Thr Ser Gly Lys Ser His Ala Ala Ser Asp Ala Pro Glu Asn Leu
145                 150                 155                 160
Thr Leu Leu Ala Glu Thr Ala Asp Ala Arg Gly Arg Ser Gly Ser Ser
                165                 170                 175
Ser Arg Thr Asn Phe Thr Ile Leu Pro Val Gly Tyr Ser Leu Glu Ile
                180                 185                 190
Ala Thr Ala Leu Thr Ser Gln Ser Gly Asn Leu Ala Ser Glu Ser Leu
            195                 200                 205
His Leu Pro Ser Ser Ser Glu Phe Asp Glu Arg Ile Ala Ala Phe
210                 215                 220
Gln Thr Lys Ser Gly Thr Ala Ser Glu Met Gly Thr Glu Arg Ala Met
225                 230                 235                 240
Gly Leu Ser Glu Glu Trp Thr Val His Ser Gln Glu Ala Thr Thr Ser
                245                 250                 255
Ala Trp Ser Pro Ser Phe Leu Pro Ala Leu Glu Met Gly Glu Leu Thr
                260                 265                 270
Thr Pro Ser Arg Lys Arg Asn Ser Ser Gly Pro Asp Leu Ser Trp Leu
                275                 280                 285
His Phe Tyr Arg Thr Ala Ala Ser Ser Pro Leu Leu Asp Leu Ser Ser
            290                 295                 300
Ser Ser Glu Ser Thr Glu Lys Leu Asn Asn Ser Thr Gly Leu Gln Ser
305                 310                 315                 320
Ser Ser Val Ser Gln Thr Lys Thr Met His Val Ala Thr Val Phe Thr
                325                 330                 335
Asp Gly Gly Pro Arg Thr Leu Arg Ser Leu Thr Val Ser Leu Gly Pro
                340                 345                 350
Val Ser Lys Thr Glu Gly Phe Pro Lys Asp Ser Arg Ile Ala Thr Thr
            355                 360                 365
Ser Ser Ser Val Leu Leu Ser Pro Ser Ala Val Glu Ser Arg Arg Asn
370                 375                 380
Ser Arg Val Thr Gly Asn Pro Gly Asp Glu Glu Phe Ile Glu Pro Ser
385                 390                 395                 400
Thr Glu Asn Glu Phe Gly Leu Thr Ser Leu Arg Trp Gln Asn Asp Ser
                405                 410                 415
Pro Thr Phe Gly Glu His Gln Leu Ala Ser Ser Glu Val Gln Asn
                420                 425                 430
Gly Ser Pro Met Ser Gln Thr Glu Thr Val Ser Arg Ser Val Ala Pro
            435                 440                 445
Met Arg Gly Gly Glu Ile Thr Ala His Trp Leu Leu Thr Asn Ser Thr
450                 455                 460
Thr Ser Ala Asp Val Thr Gly Ser Ser Ala Ser Tyr Pro Glu Gly Val
```

```
            465                 470                 475                 480
Asn Ala Ser Val Leu Thr Gln Phe Ser Asp Ser Thr Val Gln Ser Gly
                    485                 490                 495

Gly Ser His Thr Ala Leu Gly Asp Arg Ser Tyr Ser Glu Ser Ser Ser
                500                 505                 510

Thr Ser Ser Ser Glu Ser Leu Asn Ser Ser Ala Pro Arg Gly Glu Arg
            515                 520                 525

Ser Ile Ala Gly Ile Ser Tyr Gly Gln Val Arg Gly Thr Ala Ile Glu
        530                 535                 540

Gln Arg Thr Ser Ser Asp His Thr Asp His Thr Tyr Leu Ser Ser Thr
545                 550                 555                 560

Phe Thr Lys Gly Glu Arg Ala Leu Leu Ser Ile Thr Asp Asn Ser Ser
                565                 570                 575

Ser Ser Asp Ile Val Glu Ser Ser Ser Tyr Ile Lys Ile Ser Asn
                580                 585                 590

Ser Ser His Ser Glu Tyr Ser Ser Phe Phe His Ala Gln Thr Glu Arg
                595                 600                 605

Ser Asn Ile Ser Ser Tyr Asp Gly Glu Tyr Ala Gln Pro Ser Thr Glu
        610                 615                 620

Ser Pro Val Leu His Thr Ser Asn Leu Pro Ser Tyr Thr Pro Thr Ile
625                 630                 635                 640

Asn Met Pro Asn Thr Ser Val Val Leu Asp Thr Asp Ala Glu Phe Val
                645                 650                 655

Ser Asp Ser Ser Ser Ser Ser Ser Ser Ser Ser Ser Ser Ser Ser Ser
                660                 665                 670

Gly Pro Pro Leu Pro Leu Pro Ser Val Ser Gln Ser His His Leu Phe
            675                 680                 685

Ser Ser Ile Leu Pro Ser Thr Arg Ala Ser Val His Leu Leu Lys Ser
        690                 695                 700

Thr Ser Asp Ala Ser Thr Pro Trp Ser Ser Ser Pro Ser Pro Leu Pro
705                 710                 715                 720

Val Ser Leu Thr Thr Ser Thr Ser Ala Pro Leu Ser Val Ser Gln Thr
                725                 730                 735

Thr Leu Pro Gln Ser Ser Ser Thr Pro Val Leu Pro Arg Ala Arg Glu
            740                 745                 750

Thr Pro Val Thr Ser Phe Gln Thr Ser Thr Met Thr Ser Phe Met Thr
        755                 760                 765

Met Leu His Ser Ser Gln Thr Ala Asp Leu Lys Ser Gln Ser Thr Pro
770                 775                 780

His Gln Glu Lys Val Ile Thr Glu Ser Lys Ser Pro Ser Leu Val Ser
785                 790                 795                 800

Leu Pro Thr Glu Ser Thr Lys Ala Val Thr Thr Asn Ser Pro Leu Pro
                805                 810                 815

Pro Ser Leu Thr Glu Ser Ser Thr Glu Gln Thr Leu Pro Ala Thr Ser
            820                 825                 830

Thr Asn Leu Ala Gln Met Ser Pro Thr Phe Thr Thr Ile Leu Lys
        835                 840                 845

Thr Ser Gln Pro Leu Met Thr Pro Gly Thr Leu Ser Ser Thr Ala
            850                 855                 860

Ser Leu Val Thr Gly Pro Ile Ala Val Gln Thr Thr Ala Gly Lys Gln
865                 870                 875                 880

Leu Ser Leu Thr His Pro Glu Ile Leu Val Pro Gln Ile Ser Thr Glu
                885                 890                 895
```

```
Gly Gly Ile Ser Thr Glu Arg Asn Arg Val Ile Val Asp Ala Thr Thr
            900                 905                 910

Gly Leu Ile Pro Leu Thr Ser Val Pro Thr Ser Ala Lys Glu Met Thr
            915                 920                 925

Thr Lys Leu Gly Val Thr Ala Glu Tyr Ser Pro Ala Ser Arg Ser Leu
            930                 935                 940

Gly Thr Ser Pro Ser Pro Gln Thr Thr Val Val Ser Thr Ala Glu Asp
945                 950                 955                 960

Leu Ala Pro Lys Ser Ala Thr Phe Ala Val Gln Ser Thr Gln Ser
            965                 970                 975

Pro Thr Thr Val Ser Ser Ser Ala Ser Gly Lys Thr Gln Ser His Lys
            980                 985                 990

His Met Leu Thr Ala Arg Pro Ser Pro Ala Leu Arg Ala Thr Trp Gly
            995                 1000                1005

Ser Gly Phe Met
    1010
```

<210> SEQ ID NO 32
<211> LENGTH: 4464
<212> TYPE: DNA
<213> ORGANISM: Homo sapiens
<220> FEATURE:
<221> NAME/KEY: CDS
<222> LOCATION: (1)..(4461)

<400> SEQUENCE: 32

```
atg gcc tcg ccg cgc gcc tcg cgg tgg ccg ccg ccg ctc ctg ctg ctg      48
Met Ala Ser Pro Arg Ala Ser Arg Trp Pro Pro Pro Leu Leu Leu Leu
1               5                   10                  15 ttg ctg ccg ctg ctg ctg ctg ccg ccg gcg gcc ccc ggg acg cgg gac      96
Leu Leu Pro Leu Leu Leu Leu Pro Pro Ala Ala Pro Gly Thr Arg Asp
                20                  25                  30 ccg ccg cct tcc ccg gct cgc cgc gcg ctg agc ctg gcg ccc ctc gcg     144
Pro Pro Pro Ser Pro Ala Arg Arg Ala Leu Ser Leu Ala Pro Leu Ala
            35                  40                  45 gga gcg ggg ctg gag ctg cag ctg gag cgc cgc ccg gag cgc gag ccg     192
Gly Ala Gly Leu Glu Leu Gln Leu Glu Arg Arg Pro Glu Arg Glu Pro
        50                  55                  60 ccg ccc acg ccg ccc cgg gag cgc cgc ggg ccc gcg acc ccc ggc ccc     240
Pro Pro Thr Pro Pro Arg Glu Arg Arg Gly Pro Ala Thr Pro Gly Pro
65                  70                  75                  80 agc tac agg gcc cct gag cca ggc gcc gcg aca cag cgg gga ccc tcc     288
Ser Tyr Arg Ala Pro Glu Pro Gly Ala Ala Thr Gln Arg Gly Pro Ser
                85                  90                  95 ggc cgg gcc ccc aga ggc ggg agc gcg gat gct gcc tgg aaa cat tgg     336
Gly Arg Ala Pro Arg Gly Gly Ser Ala Asp Ala Ala Trp Lys His Trp
            100                 105                 110 cca gaa agt aac act gag gcc cat gta gaa aac atc acc ttc tat cag     384
Pro Glu Ser Asn Thr Glu Ala His Val Glu Asn Ile Thr Phe Tyr Gln
        115                 120                 125 aat caa gag gac ttt tca aca gtg tcc tcc aaa gag ggc gtg atg gtt     432
Asn Gln Glu Asp Phe Ser Thr Val Ser Ser Lys Glu Gly Val Met Val
    130                 135                 140 cag acc tct ggg aag agc cat gct gct tcg gat gct cca gaa aac ctc     480
Gln Thr Ser Gly Lys Ser His Ala Ala Ser Asp Ala Pro Glu Asn Leu
145                 150                 155                 160 act cta ctc gct gaa aca gca gat gct aga gga agg agc ggc tct tca     528
Thr Leu Leu Ala Glu Thr Ala Asp Ala Arg Gly Arg Ser Gly Ser Ser
                165                 170                 175
```

```
agt aga aca aac ttc acc att ttg cct gtt ggg tac tca ctg gag ata      576
Ser Arg Thr Asn Phe Thr Ile Leu Pro Val Gly Tyr Ser Leu Glu Ile
            180                 185                 190 gca aca gct ctg act tcc cag agt ggc aac tta gcc tcg gaa agt ctt      624
Ala Thr Ala Leu Thr Ser Gln Ser Gly Asn Leu Ala Ser Glu Ser Leu
            195                 200                 205 cac ctg cca tcc agc agt tca gag ttc gat gaa aga att gcc gct ttt      672
His Leu Pro Ser Ser Ser Ser Glu Phe Asp Glu Arg Ile Ala Ala Phe
            210                 215                 220 caa aca aag agt gga aca gcc tcg gag atg gga aca gag agg gcg atg      720
Gln Thr Lys Ser Gly Thr Ala Ser Glu Met Gly Thr Glu Arg Ala Met
225                 230                 235                 240 ggg ctg tca gaa gaa tgg act gtg cac agc caa gag gcc acc act tcg      768
Gly Leu Ser Glu Glu Trp Thr Val His Ser Gln Glu Ala Thr Thr Ser
                245                 250                 255 gct tgg agc ccg tcc ttt ctt cct gct ttg gag atg gga gag ctg acc      816
Ala Trp Ser Pro Ser Phe Leu Pro Ala Leu Glu Met Gly Glu Leu Thr
                260                 265                 270 acg cct tct agg aag aga aat tcc tca gga cca gat ctc tcc tgg ctg      864
Thr Pro Ser Arg Lys Arg Asn Ser Ser Gly Pro Asp Leu Ser Trp Leu
            275                 280                 285 cat ttc tac agg aca gca gct tcc tct cct ctc tta gac ctt tcc tca      912
His Phe Tyr Arg Thr Ala Ala Ser Ser Pro Leu Leu Asp Leu Ser Ser
            290                 295                 300 tct tct gaa agt aca gag aag ctt aac aac tcc act ggc ctc cag agc      960
Ser Ser Glu Ser Thr Glu Lys Leu Asn Asn Ser Thr Gly Leu Gln Ser
305                 310                 315                 320 tcc tca gtc agt caa aca aag aca atg cat gtt gcc acc gtg ttc act     1008
Ser Ser Val Ser Gln Thr Lys Thr Met His Val Ala Thr Val Phe Thr
                325                 330                 335 gat ggt ggc ccg aga acg ctg cga tct ttg acg gtc agt ctg gga cct     1056
Asp Gly Gly Pro Arg Thr Leu Arg Ser Leu Thr Val Ser Leu Gly Pro
                340                 345                 350 gtg agc aag aca gaa ggc ttc ccc aag gac tcc aga att gcc acg act     1104
Val Ser Lys Thr Glu Gly Phe Pro Lys Asp Ser Arg Ile Ala Thr Thr
            355                 360                 365 tca tcc tca gtc ctt ctt tca ccc tct gca gtg gaa tcg aga aga aac     1152
Ser Ser Ser Val Leu Leu Ser Pro Ser Ala Val Glu Ser Arg Arg Asn
            370                 375                 380 agt aga gta act ggg aat cca ggg gat gag gaa ttc att gaa cca tcc     1200
Ser Arg Val Thr Gly Asn Pro Gly Asp Glu Glu Phe Ile Glu Pro Ser
385                 390                 395                 400 aca gaa aat gaa ttt gga ctt acg tct ttg cgt tgg caa aat gat tcc     1248
Thr Glu Asn Glu Phe Gly Leu Thr Ser Leu Arg Trp Gln Asn Asp Ser
                405                 410                 415 cca acc ttt gga gaa cat cag ctt gcc agc agc tct gag gtg caa aat     1296
Pro Thr Phe Gly Glu His Gln Leu Ala Ser Ser Ser Glu Val Gln Asn
                420                 425                 430 gga agt ccc atg tct cag act gag act gtg tct agg tca gtc gca ccc     1344
Gly Ser Pro Met Ser Gln Thr Glu Thr Val Ser Arg Ser Val Ala Pro
            435                 440                 445 atg aga ggt gga gag atc act gca cac tgg ctc ttg acc aac agc aca     1392
Met Arg Gly Gly Glu Ile Thr Ala His Trp Leu Leu Thr Asn Ser Thr
450                 455                 460 aca tct gca gat gtg aca gga agc tct gct tca tat cct gaa ggt gtg     1440
Thr Ser Ala Asp Val Thr Gly Ser Ser Ala Ser Tyr Pro Glu Gly Val
465                 470                 475                 480 aat gct tca gtg ttg acc cag ttc tca gac tct act gta cag tct gga     1488
Asn Ala Ser Val Leu Thr Gln Phe Ser Asp Ser Thr Val Gln Ser Gly
```

-continued

```
              485                 490                 495
gga agt cac aca gca ttg gga gat agg agt tat tca gag tct tca tct      1536
Gly Ser His Thr Ala Leu Gly Asp Arg Ser Tyr Ser Glu Ser Ser Ser
            500                 505                 510 aca tct tcc tcg gaa agc ttg aat tca tca gca cca cgt gga gaa cgt      1584
Thr Ser Ser Ser Glu Ser Leu Asn Ser Ser Ala Pro Arg Gly Glu Arg
        515                 520                 525 tcg acc ttg gaa gac agc cga gag cca ggc caa gca cta ggt gac agt      1632
Ser Thr Leu Glu Asp Ser Arg Glu Pro Gly Gln Ala Leu Gly Asp Ser
    530                 535                 540 tcc gcc aat gca gag gac agg act tct ggg gtg ccc tct ctc ggc acc      1680
Ser Ala Asn Ala Glu Asp Arg Thr Ser Gly Val Pro Ser Leu Gly Thr
545                 550                 555                 560 cac acc ttg gct act gtc act gga aac ggg gaa cgc aca ctg cgg tct      1728
His Thr Leu Ala Thr Val Thr Gly Asn Gly Glu Arg Thr Leu Arg Ser
                565                 570                 575 gtc acc ctc acc aac acc agc atg agc acg act tct ggg gaa gca ggc      1776
Val Thr Leu Thr Asn Thr Ser Met Ser Thr Thr Ser Gly Glu Ala Gly
            580                 585                 590 agc cct gca gcg gcc atg ccc caa gaa aca gag ggt gcc tct ctg cac      1824
Ser Pro Ala Ala Ala Met Pro Gln Glu Thr Glu Gly Ala Ser Leu His
        595                 600                 605 gta aac gtg acg gac gac atg ggc ctg gtc tca cgg tca ctg gcc gcc      1872
Val Asn Val Thr Asp Asp Met Gly Leu Val Ser Arg Ser Leu Ala Ala
    610                 615                 620 tcc agt gca ctc gga gtc gct ggg att agc tac ggt caa gtg cgt ggc      1920
Ser Ser Ala Leu Gly Val Ala Gly Ile Ser Tyr Gly Gln Val Arg Gly
625                 630                 635                 640 aca gct att gaa caa agg act tcc agc gac cac aca gac cac acc tac      1968
Thr Ala Ile Glu Gln Arg Thr Ser Ser Asp His Thr Asp His Thr Tyr
                645                 650                 655 ctg tca tct act ttc acc aaa gga gaa cgg gcg tta ctg tcc att aca      2016
Leu Ser Ser Thr Phe Thr Lys Gly Glu Arg Ala Leu Leu Ser Ile Thr
            660                 665                 670 gat aac agt tca tcc tca gac att gtg gag agc tca act tct tat att      2064
Asp Asn Ser Ser Ser Ser Asp Ile Val Glu Ser Ser Thr Ser Tyr Ile
        675                 680                 685 aaa atc tca aac tct tca cat tca gag tat tcc tcc ttt ttt cat gct      2112
Lys Ile Ser Asn Ser Ser His Ser Glu Tyr Ser Ser Phe Phe His Ala
    690                 695                 700 cag act gag aga agt aac atc tca tcc tat gac ggg gaa tat gct cag      2160
Gln Thr Glu Arg Ser Asn Ile Ser Ser Tyr Asp Gly Glu Tyr Ala Gln
705                 710                 715                 720 cct tct act gag tcg cca gtt ctg cat aca tcc aac ctt ccg tcc tac      2208
Pro Ser Thr Glu Ser Pro Val Leu His Thr Ser Asn Leu Pro Ser Tyr
                725                 730                 735 aca ccc acc att aat atg ccg aac act tcg gtt gtt ctg gac act gat      2256
Thr Pro Thr Ile Asn Met Pro Asn Thr Ser Val Val Leu Asp Thr Asp
            740                 745                 750 gct gag ttt gtt agt gac tcc tcc tcc tct tcc tcc tcc tcc              2304
Ala Glu Phe Val Ser Asp Ser Ser Ser Ser Ser Ser Ser Ser
        755                 760                 765 tct tcc tcc tcc tcc tct tct tct tca ggg cct cct ttg cct ctg          2352
Ser Ser Ser Ser Ser Ser Ser Ser Ser Gly Pro Pro Leu Pro Leu
    770                 775                 780 ccc tct gtg tca caa tcc cac cat tta ttt tca tca att tta cca tca      2400
Pro Ser Val Ser Gln Ser His His Leu Phe Ser Ser Ile Leu Pro Ser
785                 790                 795                 800 acc agg gcc tct gtg cat cta cta aag tct acc tct gat gca tcc aca      2448
```

```
            Thr Arg Ala Ser Val His Leu Leu Lys Ser Thr Ser Asp Ala Ser Thr
                            805                 810                 815 cca tgg tct tcc tca cca tca cct tta cca gta tcc tta acg aca tct       2496
Pro Trp Ser Ser Ser Pro Ser Pro Leu Pro Val Ser Leu Thr Thr Ser
            820                 825                 830 aca tct gcc cca ctt tct gtc tca caa aca acc ttg cca cag tca tct       2544
Thr Ser Ala Pro Leu Ser Val Ser Gln Thr Thr Leu Pro Gln Ser Ser
            835                 840                 845 tct acc cct gtc ctg ccc agg gca agg gag act cct gtg act tca ttt       2592
Ser Thr Pro Val Leu Pro Arg Ala Arg Glu Thr Pro Val Thr Ser Phe
850                 855                 860 cag aca tca aca atg aca tca ttc atg aca atg ctc cat agt agt caa       2640
Gln Thr Ser Thr Met Thr Ser Phe Met Thr Met Leu His Ser Ser Gln
865                 870                 875                 880 act gca gac ctt aag agc cag agc acc cca cac caa gag aaa gtc att       2688
Thr Ala Asp Leu Lys Ser Gln Ser Thr Pro His Gln Glu Lys Val Ile
                885                 890                 895 aca gaa tca aag tca cca agc ctg gtg tct ctg ccc aca gag tcc acc       2736
Thr Glu Ser Lys Ser Pro Ser Leu Val Ser Leu Pro Thr Glu Ser Thr
            900                 905                 910 aaa gct gta aca aca aac tct cct ttg cct cca tcc tta aca gag tcc       2784
Lys Ala Val Thr Thr Asn Ser Pro Leu Pro Pro Ser Leu Thr Glu Ser
            915                 920                 925 tcc aca gag caa acc ctt cca gcc aca agc acc aac tta gca caa atg       2832
Ser Thr Glu Gln Thr Leu Pro Ala Thr Ser Thr Asn Leu Ala Gln Met
930                 935                 940 tct cca act ttc aca act acc att ctg aag acc tct cag cct ctt atg       2880
Ser Pro Thr Phe Thr Thr Thr Ile Leu Lys Thr Ser Gln Pro Leu Met
945                 950                 955                 960 acc act cct ggc acc ctg tca agc aca gca tct ctg gtc act ggc cct       2928
Thr Thr Pro Gly Thr Leu Ser Ser Thr Ala Ser Leu Val Thr Gly Pro
                965                 970                 975 ata gcc gta cag act aca gct gga aaa cag ctc tcg ctg acc cat cct       2976
Ile Ala Val Gln Thr Thr Ala Gly Lys Gln Leu Ser Leu Thr His Pro
            980                 985                 990 gaa ata cta gtt cct caa atc tca aca gaa ggt ggc atc agc aca gaa       3024
Glu Ile Leu Val Pro Gln Ile Ser Thr Glu Gly Gly Ile Ser Thr Glu
            995                 1000                1005 agg aac cga gtg att gtg gat gct acc tct gga ttg atc cct ttg          3069
Arg Asn Arg Val Ile Val Asp Ala Thr Ser Gly Leu Ile Pro Leu
        1010                1015                1020 acc agt gta ccc aca tca gca aaa gaa atg acc aca aag ctt ggc          3114
Thr Ser Val Pro Thr Ser Ala Lys Glu Met Thr Thr Lys Leu Gly
        1025                1030                1035 gtt aca gca gag tac agc cca gct tca cgt tcc ctc gga aca tct          3159
Val Thr Ala Glu Tyr Ser Pro Ala Ser Arg Ser Leu Gly Thr Ser
        1040                1045                1050 cct tct ccc caa acc aca gtt gtt tcc acg gct gaa gac ttg gct          3204
Pro Ser Pro Gln Thr Thr Val Val Ser Thr Ala Glu Asp Leu Ala
        1055                1060                1065 ccc aaa tct gcc acc ttt gct gtt cag agc agc aca cag tca cca          3249
Pro Lys Ser Ala Thr Phe Ala Val Gln Ser Ser Thr Gln Ser Pro
        1070                1075                1080 aca aca ctg tcc tct tca gcc tca gtc aac agc tgt gct gtg aac          3294
Thr Thr Leu Ser Ser Ser Ala Ser Val Asn Ser Cys Ala Val Asn
        1085                1090                1095 cct tgt ctt cac aat ggc gaa tgc gtc gca gac aac acc agc cgt          3339
Pro Cys Leu His Asn Gly Glu Cys Val Ala Asp Asn Thr Ser Arg
        1100                1105                1110
```

```
                                                           -continued ggc  tac  cac  tgc  agg  tgc  ccg  cct  tcc  tgg  caa  ggg  gat  gat  tgc    3384
Gly  Tyr  His  Cys  Arg  Cys  Pro  Pro  Ser  Trp  Gln  Gly  Asp  Asp  Cys
     1115                950       1120                          1125 agt  gtg  gat  gtg  aat  gag  tgc  ctg  tcg  aac  ccc  tgc  cca  tcc  aca    3429
Ser  Val  Asp  Val  Asn  Glu  Cys  Leu  Ser  Asn  Pro  Cys  Pro  Ser  Thr
     1130                      1135                          1140 gcc  atg  tgc  aac  aat  act  cag  gga  tcc  ttt  atc  tgc  aaa  tgc  ccg    3474
Ala  Met  Cys  Asn  Asn  Thr  Gln  Gly  Ser  Phe  Ile  Cys  Lys  Cys  Pro
     1145                      1150                          1155 gtt  ggg  tac  cag  ttg  gaa  aaa  gga  ata  tgc  aat  ttg  gtt  aga  acc    3519
Val  Gly  Tyr  Gln  Leu  Glu  Lys  Gly  Ile  Cys  Asn  Leu  Val  Arg  Thr
     1160                      1165                          1170 ttc  gtg  aca  gag  ttt  aaa  tta  aag  aga  act  ttt  ctt  aat  aca  act    3564
Phe  Val  Thr  Glu  Phe  Lys  Leu  Lys  Arg  Thr  Phe  Leu  Asn  Thr  Thr
     1175                      1180                          1185 gtg  gaa  aaa  cat  tca  gac  cta  caa  gaa  gtt  gaa  aat  gag  atc  acc    3609
Val  Glu  Lys  His  Ser  Asp  Leu  Gln  Glu  Val  Glu  Asn  Glu  Ile  Thr
     1190                      1195                          1200 aaa  acg  tta  aat  atg  tgt  ttt  tca  gcg  tta  cct  agt  tac  atc  cga    3654
Lys  Thr  Leu  Asn  Met  Cys  Phe  Ser  Ala  Leu  Pro  Ser  Tyr  Ile  Arg
     1205                      1210                          1215 tct  aca  gtt  cac  gcc  tct  agg  gag  tcc  aac  gcg  gtg  gtg  atc  tca    3699
Ser  Thr  Val  His  Ala  Ser  Arg  Glu  Ser  Asn  Ala  Val  Val  Ile  Ser
     1220                      1225                          1230 ctg  caa  aca  acc  ttt  tcc  ctg  gcc  tcc  aat  gtg  acg  cta  ttt  gac    3744
Leu  Gln  Thr  Thr  Phe  Ser  Leu  Ala  Ser  Asn  Val  Thr  Leu  Phe  Asp
     1235                      1240                          1245 ctg  gct  gat  agg  atg  cag  aaa  tgt  gtc  aac  tcc  tgc  aag  tcc  tct    3789
Leu  Ala  Asp  Arg  Met  Gln  Lys  Cys  Val  Asn  Ser  Cys  Lys  Ser  Ser
     1250                      1255                          1260 gct  gag  gtc  tgc  cag  ctc  ttg  gga  tct  cag  agg  cgg  atc  ttt  aga    3834
Ala  Glu  Val  Cys  Gln  Leu  Leu  Gly  Ser  Gln  Arg  Arg  Ile  Phe  Arg
     1265                      1270                          1275 gcg  ggc  agc  ttg  tgc  aag  cgg  aag  agt  ccc  gaa  tgt  gac  aaa  gac    3879
Ala  Gly  Ser  Leu  Cys  Lys  Arg  Lys  Ser  Pro  Glu  Cys  Asp  Lys  Asp
     1280                      1285                          1290 acc  tcc  atc  tgc  act  gac  ctg  gac  ggc  gtt  gcc  ctg  tgc  cag  tgc    3924
Thr  Ser  Ile  Cys  Thr  Asp  Leu  Asp  Gly  Val  Ala  Leu  Cys  Gln  Cys
     1295                      1300                          1305 aag  tcg  gga  tac  ttt  cag  ttc  aac  aag  atg  gac  cac  tcc  tgc  cga    3969
Lys  Ser  Gly  Tyr  Phe  Gln  Phe  Asn  Lys  Met  Asp  His  Ser  Cys  Arg
     1310                      1315                          1320 gca  tgt  gaa  gat  gga  tat  agg  ctt  gaa  aat  gaa  acc  tgc  atg  agt    4014
Ala  Cys  Glu  Asp  Gly  Tyr  Arg  Leu  Glu  Asn  Glu  Thr  Cys  Met  Ser
     1325                      1330                          1335 tgc  cca  ttt  ggc  ctt  ggt  ggt  ctc  aac  tgt  gga  aac  ccc  tat  cag    4059
Cys  Pro  Phe  Gly  Leu  Gly  Gly  Leu  Asn  Cys  Gly  Asn  Pro  Tyr  Gln
     1340                      1345                          1350 ctt  atc  act  gtg  gtg  atc  gca  gcc  gcg  gga  ggt  ggg  ctc  ctg  ctc    4104
Leu  Ile  Thr  Val  Val  Ile  Ala  Ala  Ala  Gly  Gly  Gly  Leu  Leu  Leu
     1355                      1360                          1365 atc  cta  ggc  atc  gca  ctg  att  gtt  acc  tgt  tgc  aga  aag  aat  aaa    4149
Ile  Leu  Gly  Ile  Ala  Leu  Ile  Val  Thr  Cys  Cys  Arg  Lys  Asn  Lys
     1370                      1375                          1380 aat  gac  ata  agc  aaa  ctc  atc  ttc  aaa  agt  gga  gat  ttc  caa  atg    4194
Asn  Asp  Ile  Ser  Lys  Leu  Ile  Phe  Lys  Ser  Gly  Asp  Phe  Gln  Met
     1385                      1390                          1395 tcc  cca  tat  gct  gaa  tac  ccc  aaa  aat  cct  cgc  tca  caa  gaa  tgg    4239
Ser  Pro  Tyr  Ala  Glu  Tyr  Pro  Lys  Asn  Pro  Arg  Ser  Gln  Glu  Trp
     1400                      1405                          1410
```

|  |  |  |  |  |  |  |  |  |  |  |  |
|---|---|---|---|---|---|---|---|---|---|---|---|
| ggc | cga | gaa | gct | att | gaa | atg | cat | gag | aat | gga | agt | acc | aaa | aac | 4284 |
| Gly | Arg | Glu | Ala | Ile | Glu | Met | His | Glu | Asn | Gly | Ser | Thr | Lys | Asn | |
| | 1415 | | | | 1420 | | | | | 1425 | | | | | |
| ctc | ctc | cag | atg | acg | gat | gtg | tac | tac | tcg | cct | aca | agt | gta | agg | 4329 |
| Leu | Leu | Gln | Met | Thr | Asp | Val | Tyr | Tyr | Ser | Pro | Thr | Ser | Val | Arg | |
| | 1430 | | | | 1435 | | | | | 1440 | | | | | |
| aat | cca | gaa | ctt | gaa | cga | aac | gga | ctc | tac | ccg | gcc | tac | act | gga | 4374 |
| Asn | Pro | Glu | Leu | Glu | Arg | Asn | Gly | Leu | Tyr | Pro | Ala | Tyr | Thr | Gly | |
| | 1445 | | | | 1450 | | | | | 1455 | | | | | |
| ctg | cca | gga | tca | cgg | cat | tct | tgc | att | ttc | ccc | gga | cag | tat | aac | 4419 |
| Leu | Pro | Gly | Ser | Arg | His | Ser | Cys | Ile | Phe | Pro | Gly | Gln | Tyr | Asn | |
| | 1460 | | | | 1465 | | | | | 1470 | | | | | |
| ccg | tct | ttc | atc | agt | gat | gaa | agc | aga | aga | aga | gac | tac | ttt | taa | 4464 |
| Pro | Ser | Phe | Ile | Ser | Asp | Glu | Ser | Arg | Arg | Arg | Asp | Tyr | Phe | | |
| | 1475 | | | | 1480 | | | | | 1485 | | | | | |

<210> SEQ ID NO 33
<211> LENGTH: 1487
<212> TYPE: PRT
<213> ORGANISM: Homo sapiens

<400> SEQUENCE: 33

Met Ala Ser Pro Arg Ala Ser Arg Trp Pro Pro Leu Leu Leu Leu
1               5                   10                  15

Leu Leu Pro Leu Leu Leu Pro Pro Ala Ala Pro Gly Thr Arg Asp
                20                  25                  30

Pro Pro Pro Ser Pro Ala Arg Arg Ala Leu Ser Leu Ala Pro Leu Ala
            35                  40                  45

Gly Ala Gly Leu Glu Leu Gln Leu Glu Arg Arg Pro Glu Arg Glu Pro
    50                  55                  60

Pro Pro Thr Pro Arg Glu Arg Arg Gly Pro Ala Thr Pro Gly Pro
65                  70                  75                  80

Ser Tyr Arg Ala Pro Glu Pro Gly Ala Ala Thr Gln Arg Gly Pro Ser
                85                  90                  95

Gly Arg Ala Pro Arg Gly Gly Ser Ala Asp Ala Ala Trp Lys His Trp
            100                 105                 110

Pro Glu Ser Asn Thr Glu Ala His Val Glu Asn Ile Thr Phe Tyr Gln
        115                 120                 125

Asn Gln Glu Asp Phe Ser Thr Val Ser Ser Lys Glu Gly Val Met Val
    130                 135                 140

Gln Thr Ser Gly Lys Ser His Ala Ala Ser Asp Ala Pro Glu Asn Leu
145                 150                 155                 160

Thr Leu Leu Ala Glu Thr Ala Asp Ala Arg Gly Arg Ser Gly Ser Ser
                165                 170                 175

Ser Arg Thr Asn Phe Thr Ile Leu Pro Val Gly Tyr Ser Leu Glu Ile
            180                 185                 190

Ala Thr Ala Leu Thr Ser Gln Ser Gly Asn Leu Ala Ser Glu Ser Leu
        195                 200                 205

His Leu Pro Ser Ser Ser Glu Phe Asp Glu Arg Ile Ala Ala Phe
    210                 215                 220

Gln Thr Lys Ser Gly Thr Ala Ser Glu Met Gly Thr Glu Arg Ala Met
225                 230                 235                 240

Gly Leu Ser Glu Glu Trp Thr Val His Ser Gln Glu Ala Thr Thr Ser
                245                 250                 255

Ala Trp Ser Pro Ser Phe Leu Pro Ala Leu Glu Met Gly Glu Leu Thr
            260                 265                 270

```
Thr Pro Ser Arg Lys Arg Asn Ser Ser Gly Pro Asp Leu Ser Trp Leu
            275                 280                 285

His Phe Tyr Arg Thr Ala Ala Ser Ser Pro Leu Leu Asp Leu Ser Ser
    290                 295                 300

Ser Ser Glu Ser Thr Glu Lys Leu Asn Asn Ser Thr Gly Leu Gln Ser
305                 310                 315                 320

Ser Ser Val Ser Gln Thr Lys Thr Met His Val Ala Thr Val Phe Thr
                325                 330                 335

Asp Gly Gly Pro Arg Thr Leu Arg Ser Leu Thr Val Ser Leu Gly Pro
                340                 345                 350

Val Ser Lys Thr Glu Gly Phe Pro Lys Asp Ser Arg Ile Ala Thr Thr
    355                 360                 365

Ser Ser Ser Val Leu Leu Ser Pro Ser Ala Val Glu Ser Arg Arg Asn
370                 375                 380

Ser Arg Val Thr Gly Asn Pro Gly Asp Glu Glu Phe Ile Glu Pro Ser
385                 390                 395                 400

Thr Glu Asn Glu Phe Gly Leu Thr Ser Leu Arg Trp Gln Asn Asp Ser
                405                 410                 415

Pro Thr Phe Gly Glu His Gln Leu Ala Ser Ser Glu Val Gln Asn
                420                 425                 430

Gly Ser Pro Met Ser Gln Thr Glu Thr Val Ser Arg Ser Val Ala Pro
            435                 440                 445

Met Arg Gly Gly Glu Ile Thr Ala His Trp Leu Leu Thr Asn Ser Thr
    450                 455                 460

Thr Ser Ala Asp Val Thr Gly Ser Ser Ala Ser Tyr Pro Glu Gly Val
465                 470                 475                 480

Asn Ala Ser Val Leu Thr Gln Phe Ser Asp Ser Thr Val Gln Ser Gly
                485                 490                 495

Gly Ser His Thr Ala Leu Gly Asp Arg Ser Tyr Ser Glu Ser Ser Ser
            500                 505                 510

Thr Ser Ser Ser Glu Ser Leu Asn Ser Ser Ala Pro Arg Gly Glu Arg
        515                 520                 525

Ser Thr Leu Glu Asp Ser Arg Glu Pro Gly Gln Ala Leu Gly Asp Ser
    530                 535                 540

Ser Ala Asn Ala Glu Asp Arg Thr Ser Gly Val Pro Ser Leu Gly Thr
545                 550                 555                 560

His Thr Leu Ala Thr Val Thr Gly Asn Gly Glu Arg Thr Leu Arg Ser
                565                 570                 575

Val Thr Leu Thr Asn Thr Ser Met Ser Thr Thr Ser Gly Glu Ala Gly
            580                 585                 590

Ser Pro Ala Ala Ala Met Pro Gln Glu Thr Glu Gly Ala Ser Leu His
    595                 600                 605

Val Asn Val Thr Asp Asp Met Gly Leu Val Ser Arg Ser Leu Ala Ala
610                 615                 620

Ser Ser Ala Leu Gly Val Ala Gly Ile Ser Tyr Gly Gln Val Arg Gly
625                 630                 635                 640

Thr Ala Ile Glu Gln Arg Thr Ser Ser Asp His Thr Asp His Thr Tyr
                645                 650                 655

Leu Ser Ser Thr Phe Thr Lys Gly Glu Arg Ala Leu Leu Ser Ile Thr
                660                 665                 670

Asp Asn Ser Ser Ser Ser Asp Ile Val Glu Ser Ser Thr Ser Tyr Ile
                675                 680                 685
```

```
Lys Ile Ser Asn Ser Ser His Ser Glu Tyr Ser Ser Phe Phe His Ala
690                 695                 700
Gln Thr Glu Arg Ser Asn Ile Ser Ser Tyr Asp Gly Glu Tyr Ala Gln
705                 710                 715                 720
Pro Ser Thr Glu Ser Pro Val Leu His Thr Ser Asn Leu Pro Ser Tyr
            725                 730                 735
Thr Pro Thr Ile Asn Met Pro Asn Thr Ser Val Val Leu Asp Thr Asp
            740                 745                 750
Ala Glu Phe Val Ser Asp Ser Ser Ser Ser Ser Ser Ser Ser Ser Ser
            755                 760                 765
Ser Ser Ser Ser Ser Ser Ser Ser Ser Gly Pro Pro Leu Pro Leu
770                 775                 780
Pro Ser Val Ser Gln Ser His His Leu Phe Ser Ser Ile Leu Pro Ser
785                 790                 795                 800
Thr Arg Ala Ser Val His Leu Leu Lys Ser Thr Ser Asp Ala Ser Thr
            805                 810                 815
Pro Trp Ser Ser Pro Ser Pro Leu Pro Val Ser Leu Thr Thr Ser
            820                 825                 830
Thr Ser Ala Pro Leu Ser Val Ser Gln Thr Thr Leu Pro Gln Ser Ser
            835                 840                 845
Ser Thr Pro Val Leu Pro Arg Ala Arg Glu Thr Pro Val Thr Ser Phe
850                 855                 860
Gln Thr Ser Thr Met Thr Ser Phe Met Thr Met Leu His Ser Ser Gln
865                 870                 875                 880
Thr Ala Asp Leu Lys Ser Gln Ser Thr Pro His Gln Glu Lys Val Ile
            885                 890                 895
Thr Glu Ser Lys Ser Pro Ser Leu Val Ser Leu Pro Thr Glu Ser Thr
            900                 905                 910
Lys Ala Val Thr Thr Asn Ser Pro Leu Pro Pro Ser Leu Thr Glu Ser
            915                 920                 925
Ser Thr Glu Gln Thr Leu Pro Ala Thr Ser Thr Asn Leu Ala Gln Met
930                 935                 940
Ser Pro Thr Phe Thr Thr Thr Ile Leu Lys Thr Ser Gln Pro Leu Met
945                 950                 955                 960
Thr Thr Pro Gly Thr Leu Ser Ser Thr Ala Ser Leu Val Thr Gly Pro
            965                 970                 975
Ile Ala Val Gln Thr Thr Ala Gly Lys Gln Leu Ser Leu Thr His Pro
            980                 985                 990
Glu Ile Leu Val Pro Gln Ile Ser Thr Glu Gly Gly Ile Ser Thr Glu
            995                 1000                1005
Arg Asn Arg Val Ile Val Asp Ala Thr Ser Gly Leu Ile Pro Leu
    1010                1015                1020
Thr Ser Val Pro Thr Ser Ala Lys Glu Met Thr Thr Lys Leu Gly
    1025                1030                1035
Val Thr Ala Glu Tyr Ser Pro Ala Ser Arg Ser Leu Gly Thr Ser
    1040                1045                1050
Pro Ser Pro Gln Thr Thr Val Val Ser Thr Ala Glu Asp Leu Ala
    1055                1060                1065
Pro Lys Ser Ala Thr Phe Ala Val Gln Ser Ser Thr Gln Ser Pro
    1070                1075                1080
Thr Thr Leu Ser Ser Ser Ala Ser Val Asn Ser Cys Ala Val Asn
    1085                1090                1095
Pro Cys Leu His Asn Gly Glu Cys Val Ala Asp Asn Thr Ser Arg
```

-continued

```
                1100                1105                1110
Gly Tyr His Cys Arg Cys Pro Pro Ser Trp Gln Gly Asp Asp Cys
            1115                1120                1125
Ser Val Asp Val Asn Glu Cys Leu Ser Asn Pro Cys Pro Ser Thr
            1130                1135                1140
Ala Met Cys Asn Asn Thr Gln Gly Ser Phe Ile Cys Lys Cys Pro
            1145                1150                1155
Val Gly Tyr Gln Leu Glu Lys Gly Ile Cys Asn Leu Val Arg Thr
            1160                1165                1170
Phe Val Thr Glu Phe Lys Leu Lys Arg Thr Phe Leu Asn Thr Thr
            1175                1180                1185
Val Glu Lys His Ser Asp Leu Gln Glu Val Glu Asn Glu Ile Thr
            1190                1195                1200
Lys Thr Leu Asn Met Cys Phe Ser Ala Leu Pro Ser Tyr Ile Arg
            1205                1210                1215
Ser Thr Val His Ala Ser Arg Glu Ser Asn Ala Val Val Ile Ser
            1220                1225                1230
Leu Gln Thr Thr Phe Ser Leu Ala Ser Asn Val Thr Leu Phe Asp
            1235                1240                1245
Leu Ala Asp Arg Met Gln Lys Cys Val Asn Ser Cys Lys Ser Ser
            1250                1255                1260
Ala Glu Val Cys Gln Leu Leu Gly Ser Gln Arg Arg Ile Phe Arg
            1265                1270                1275
Ala Gly Ser Leu Cys Lys Arg Lys Ser Pro Glu Cys Asp Lys Asp
            1280                1285                1290
Thr Ser Ile Cys Thr Asp Leu Asp Gly Val Ala Leu Cys Gln Cys
            1295                1300                1305
Lys Ser Gly Tyr Phe Gln Phe Asn Lys Met Asp His Ser Cys Arg
            1310                1315                1320
Ala Cys Glu Asp Gly Tyr Arg Leu Glu Asn Glu Thr Cys Met Ser
            1325                1330                1335
Cys Pro Phe Gly Leu Gly Gly Leu Asn Cys Gly Asn Pro Tyr Gln
            1340                1345                1350
Leu Ile Thr Val Val Ile Ala Ala Gly Gly Gly Leu Leu Leu
            1355                1360                1365
Ile Leu Gly Ile Ala Leu Ile Val Thr Cys Cys Arg Lys Asn Lys
            1370                1375                1380
Asn Asp Ile Ser Lys Leu Ile Phe Lys Ser Gly Asp Phe Gln Met
            1385                1390                1395
Ser Pro Tyr Ala Glu Tyr Pro Lys Asn Pro Arg Ser Gln Glu Trp
            1400                1405                1410
Gly Arg Glu Ala Ile Glu Met His Glu Asn Gly Ser Thr Lys Asn
            1415                1420                1425
Leu Leu Gln Met Thr Asp Val Tyr Tyr Ser Pro Thr Ser Val Arg
            1430                1435                1440
Asn Pro Glu Leu Glu Arg Asn Gly Leu Tyr Pro Ala Tyr Thr Gly
            1445                1450                1455
Leu Pro Gly Ser Arg His Ser Cys Ile Phe Pro Gly Gln Tyr Asn
            1460                1465                1470
Pro Ser Phe Ile Ser Asp Glu Ser Arg Arg Arg Asp Tyr Phe
            1475                1480                1485

<210> SEQ ID NO 34
```

```
<211> LENGTH: 4164
<212> TYPE: DNA
<213> ORGANISM: Homo sapiens
<220> FEATURE:
<221> NAME/KEY: CDS
<222> LOCATION: (1)..(4161)

<400> SEQUENCE: 34
```

| | | | | | | | | | | | | | | | | |
|---|---|---|---|---|---|---|---|---|---|---|---|---|---|---|---|---|
| atg | gcc | tcg | ccg | cgc | gcc | tcg | cgg | tgg | ccg | ccg | ccg | ctc | ctg | ctg | ctg | 48 |
| Met | Ala | Ser | Pro | Arg | Ala | Ser | Arg | Trp | Pro | Pro | Pro | Leu | Leu | Leu | Leu | |
| 1 | | | | 5 | | | | | 10 | | | | | 15 | | |
| ttg | ctg | ccg | ctg | ctg | ctg | ctg | ccg | ccg | gcg | gcc | ccc | ggg | acg | cgg | gac | 96 |
| Leu | Leu | Pro | Leu | Leu | Leu | Leu | Pro | Pro | Ala | Ala | Pro | Gly | Thr | Arg | Asp | |
| | | | 20 | | | | | 25 | | | | | 30 | | | |
| ccg | ccg | cct | tcc | ccg | gct | cgc | cgc | gcg | ctg | agc | ctg | gcg | ccc | ctc | gcg | 144 |
| Pro | Pro | Pro | Ser | Pro | Ala | Arg | Arg | Ala | Leu | Ser | Leu | Ala | Pro | Leu | Ala | |
| | | 35 | | | | | 40 | | | | | 45 | | | | |
| gga | gcg | ggg | ctg | gag | ctg | cag | ctg | gag | cgc | cgc | ccg | gag | cgc | gag | ccg | 192 |
| Gly | Ala | Gly | Leu | Glu | Leu | Gln | Leu | Glu | Arg | Arg | Pro | Glu | Arg | Glu | Pro | |
| 50 | | | | | 55 | | | | | 60 | | | | | | |
| ccg | ccc | acg | ccg | ccc | cgg | gag | cgc | cgc | ggg | ccc | gcg | acc | ccc | ggc | ccc | 240 |
| Pro | Pro | Thr | Pro | Pro | Arg | Glu | Arg | Arg | Gly | Pro | Ala | Thr | Pro | Gly | Pro | |
| 65 | | | | | 70 | | | | | 75 | | | | | 80 | |
| agc | tac | agg | gcc | cct | gag | cca | ggc | gcc | gcg | aca | cag | cgg | gga | ccc | tcc | 288 |
| Ser | Tyr | Arg | Ala | Pro | Glu | Pro | Gly | Ala | Ala | Thr | Gln | Arg | Gly | Pro | Ser | |
| | | | | 85 | | | | | 90 | | | | | 95 | | |
| ggc | cgg | gcc | ccc | aga | ggc | ggg | agc | gcg | gat | gct | gcc | tgg | aaa | cat | tgg | 336 |
| Gly | Arg | Ala | Pro | Arg | Gly | Gly | Ser | Ala | Asp | Ala | Ala | Trp | Lys | His | Trp | |
| | | | 100 | | | | | 105 | | | | | 110 | | | |
| cca | gaa | agt | aac | act | gag | gcc | cat | gta | gaa | aac | atc | acc | ttc | tat | cag | 384 |
| Pro | Glu | Ser | Asn | Thr | Glu | Ala | His | Val | Glu | Asn | Ile | Thr | Phe | Tyr | Gln | |
| | | 115 | | | | | 120 | | | | | 125 | | | | |
| aat | caa | gag | gac | ttt | tca | aca | gtg | tcc | tcc | aaa | gag | ggc | gtg | atg | gtt | 432 |
| Asn | Gln | Glu | Asp | Phe | Ser | Thr | Val | Ser | Ser | Lys | Glu | Gly | Val | Met | Val | |
| 130 | | | | | 135 | | | | | 140 | | | | | | |
| cag | acc | tct | ggg | aag | agc | cat | gct | gct | tcg | gat | gct | cca | gaa | aac | ctc | 480 |
| Gln | Thr | Ser | Gly | Lys | Ser | His | Ala | Ala | Ser | Asp | Ala | Pro | Glu | Asn | Leu | |
| 145 | | | | | 150 | | | | | 155 | | | | | 160 | |
| act | cta | ctc | gct | gaa | aca | gca | gat | gct | aga | gga | agg | agc | ggc | tct | tca | 528 |
| Thr | Leu | Leu | Ala | Glu | Thr | Ala | Asp | Ala | Arg | Gly | Arg | Ser | Gly | Ser | Ser | |
| | | | | 165 | | | | | 170 | | | | | 175 | | |
| agt | aga | aca | aac | ttc | acc | att | ttg | cct | gtt | ggg | tac | tca | ctg | gag | ata | 576 |
| Ser | Arg | Thr | Asn | Phe | Thr | Ile | Leu | Pro | Val | Gly | Tyr | Ser | Leu | Glu | Ile | |
| | | | 180 | | | | | 185 | | | | | 190 | | | |
| gca | aca | gct | ctg | act | tcc | cag | agt | ggc | aac | tta | gcc | tcg | gaa | agt | ctt | 624 |
| Ala | Thr | Ala | Leu | Thr | Ser | Gln | Ser | Gly | Asn | Leu | Ala | Ser | Glu | Ser | Leu | |
| | | 195 | | | | | 200 | | | | | 205 | | | | |
| cac | ctg | cca | tcc | agc | agt | tca | gag | ttc | gat | gaa | aga | att | gcc | gct | ttt | 672 |
| His | Leu | Pro | Ser | Ser | Ser | Ser | Glu | Phe | Asp | Glu | Arg | Ile | Ala | Ala | Phe | |
| | 210 | | | | | 215 | | | | | 220 | | | | | |
| caa | aca | aag | agt | gga | aca | gcc | tcg | gag | atg | gga | aca | gag | agg | gcg | atg | 720 |
| Gln | Thr | Lys | Ser | Gly | Thr | Ala | Ser | Glu | Met | Gly | Thr | Glu | Arg | Ala | Met | |
| 225 | | | | | 230 | | | | | 235 | | | | | 240 | |
| ggg | ctg | tca | gaa | gaa | tgg | act | gtg | cac | agc | caa | gag | gcc | acc | act | tcg | 768 |
| Gly | Leu | Ser | Glu | Glu | Trp | Thr | Val | His | Ser | Gln | Glu | Ala | Thr | Thr | Ser | |
| | | | | 245 | | | | | 250 | | | | | 255 | | |
| gct | tgg | agc | ccg | tcc | ttt | ctt | cct | gct | ttg | gag | atg | gga | gag | ctg | acc | 816 |
| Ala | Trp | Ser | Pro | Ser | Phe | Leu | Pro | Ala | Leu | Glu | Met | Gly | Glu | Leu | Thr | |
| | | | 260 | | | | | 265 | | | | | 270 | | | |
| acg | cct | tct | agg | aag | aga | aat | tcc | tca | gga | cca | gat | ctc | tcc | tgg | ctg | 864 |
| Thr | Pro | Ser | Arg | Lys | Arg | Asn | Ser | Ser | Gly | Pro | Asp | Leu | Ser | Trp | Leu | |

```
                275                 280                 285
cat ttc tac agg aca gca gct tcc tct cct ctc tta gac ctt tcc tca    912
His Phe Tyr Arg Thr Ala Ala Ser Ser Pro Leu Leu Asp Leu Ser Ser
    290                 295                 300 tct tct gaa agt aca gag aag ctt aac aac tcc act ggc ctc cag agc    960
Ser Ser Glu Ser Thr Glu Lys Leu Asn Asn Ser Thr Gly Leu Gln Ser
305                 310                 315                 320 tcc tca gtc agt caa aca aag aca atg cat gtt gcc acc gtg ttc act   1008
Ser Ser Val Ser Gln Thr Lys Thr Met His Val Ala Thr Val Phe Thr
        325                 330                 335 gat ggt ggc ccg aga acg ctg cga tct ttg acg gtc agt ctg gga cct   1056
Asp Gly Gly Pro Arg Thr Leu Arg Ser Leu Thr Val Ser Leu Gly Pro
            340                 345                 350 gtg agc aag aca gaa ggc ttc ccc aag gac tcc aga att gcc acg act   1104
Val Ser Lys Thr Glu Gly Phe Pro Lys Asp Ser Arg Ile Ala Thr Thr
                355                 360                 365 tca tcc tca gtc ctt ctt tca ccc tct gca gtg gaa tcg aga aga aac   1152
Ser Ser Ser Val Leu Leu Ser Pro Ser Ala Val Glu Ser Arg Arg Asn
370                 375                 380 agt aga gta act ggg aat cca ggg gat gag gaa ttc att gaa cca tcc   1200
Ser Arg Val Thr Gly Asn Pro Gly Asp Glu Glu Phe Ile Glu Pro Ser
385                 390                 395                 400 aca gaa aat gaa ttt gga ctt acg tct ttg cgt tgg caa aat gat tcc   1248
Thr Glu Asn Glu Phe Gly Leu Thr Ser Leu Arg Trp Gln Asn Asp Ser
        405                 410                 415 cca acc ttt gga gaa cat cag ctt gcc agc agc tct gag gtg caa aat   1296
Pro Thr Phe Gly Glu His Gln Leu Ala Ser Ser Ser Glu Val Gln Asn
            420                 425                 430 gga agt ccc atg tct cag act gag act gtg tct agg tca gtc gca ccc   1344
Gly Ser Pro Met Ser Gln Thr Glu Thr Val Ser Arg Ser Val Ala Pro
                435                 440                 445 atg aga ggt gga gag atc act gca cac tgg ctc ttg acc aac agc aca   1392
Met Arg Gly Gly Glu Ile Thr Ala His Trp Leu Leu Thr Asn Ser Thr
450                 455                 460 aca tct gca gat gtg aca gga agc tct gct tca tat cct gaa ggt gtg   1440
Thr Ser Ala Asp Val Thr Gly Ser Ser Ala Ser Tyr Pro Glu Gly Val
465                 470                 475                 480 aat gct tca gtg ttg acc cag ttc tca gac tct act gta cag tct gga   1488
Asn Ala Ser Val Leu Thr Gln Phe Ser Asp Ser Thr Val Gln Ser Gly
        485                 490                 495 gga agt cac aca gca ttg gga gat agg agt tat tca gag tct tca tct   1536
Gly Ser His Thr Ala Leu Gly Asp Arg Ser Tyr Ser Glu Ser Ser Ser
            500                 505                 510 aca tct tcc tcg gaa agc ttg aat tca tca gca cca cgt gga gaa cgt   1584
Thr Ser Ser Ser Glu Ser Leu Asn Ser Ser Ala Pro Arg Gly Glu Arg
                515                 520                 525 tcg atc gct ggg att agc tac ggt caa gtg cgt ggc aca gct att gaa   1632
Ser Ile Ala Gly Ile Ser Tyr Gly Gln Val Arg Gly Thr Ala Ile Glu
530                 535                 540 caa agg act tcc agc gac cac aca gac cac acc tac ctg tca tct act   1680
Gln Arg Thr Ser Ser Asp His Thr Asp His Thr Tyr Leu Ser Ser Thr
545                 550                 555                 560 ttc acc aaa gga gaa cgg gcg tta ctg tcc att aca gat aac agt tca   1728
Phe Thr Lys Gly Glu Arg Ala Leu Leu Ser Ile Thr Asp Asn Ser Ser
        565                 570                 575 tcc tca gac att gtg gag agc tca act tct tat att aaa atc tca aac   1776
Ser Ser Asp Ile Val Glu Ser Ser Thr Ser Tyr Ile Lys Ile Ser Asn
            580                 585                 590 tct tca cat tca gag tat tcc tcc ttt ttt cat gct cag act gag aga   1824
```

```
Ser Ser His Ser Glu Tyr Ser Ser Phe Phe His Ala Gln Thr Glu Arg
        595                 600                 605 agt aac atc tca tcc tat gac ggg gaa tat gct cag cct tct act gag      1872
Ser Asn Ile Ser Ser Tyr Asp Gly Glu Tyr Ala Gln Pro Ser Thr Glu
610                 615                 620 tcg cca gtt ctg cat aca tcc aac ctt ccg tcc tac aca ccc acc att      1920
Ser Pro Val Leu His Thr Ser Asn Leu Pro Ser Tyr Thr Pro Thr Ile
625                 630                 635                 640 aat atg ccg aac act tcg gtt gtt ctg gac act gat gct gag ttt gtt      1968
Asn Met Pro Asn Thr Ser Val Val Leu Asp Thr Asp Ala Glu Phe Val
                645                 650                 655 agt gac tcc tcc tcc tcc tct tcc tcc tcc tcc tcc tct tcc tcc tcc      2016
Ser Asp Ser Ser Ser Ser Ser Ser Ser Ser Ser Ser Ser Ser Ser Ser
                660                 665                 670 tcc tct tct tct tct tca ggg cct cct ttg cct ctg ccc tct gtg tca      2064
Ser Ser Ser Ser Ser Ser Gly Pro Pro Leu Pro Leu Pro Ser Val Ser
                675                 680                 685 caa tcc cac cat tta ttt tca tca att tta cca tca acc agg gcc tct      2112
Gln Ser His His Leu Phe Ser Ser Ile Leu Pro Ser Thr Arg Ala Ser
        690                 695                 700 gtg cat cta cta aag tct acc tct gat gca tcc aca cca tgg tct tcc      2160
Val His Leu Leu Lys Ser Thr Ser Asp Ala Ser Thr Pro Trp Ser Ser
705                 710                 715                 720 tca cca tca cct tta cca gta tcc tta acg aca tct aca tct gcc cca      2208
Ser Pro Ser Pro Leu Pro Val Ser Leu Thr Thr Ser Thr Ser Ala Pro
                725                 730                 735 ctt tct gtc tca caa aca acc ttg cca cag tca tct tct acc cct gtc      2256
Leu Ser Val Ser Gln Thr Thr Leu Pro Gln Ser Ser Ser Thr Pro Val
                740                 745                 750 ctg ccc agg gca agg gag act cct gtg act tca ttt cag aca tca aca      2304
Leu Pro Arg Ala Arg Glu Thr Pro Val Thr Ser Phe Gln Thr Ser Thr
                755                 760                 765 atg aca tca ttc atg aca atg ctc cat agt agt caa act gca gac ctt      2352
Met Thr Ser Phe Met Thr Met Leu His Ser Ser Gln Thr Ala Asp Leu
770                 775                 780 aag agc cag agc acc cca cac caa gag aaa gtc att aca gaa tca aag      2400
Lys Ser Gln Ser Thr Pro His Gln Glu Lys Val Ile Thr Glu Ser Lys
785                 790                 795                 800 tca cca agc ctg gtg tct ctg ccc aca gag tcc acc aaa gct gta aca      2448
Ser Pro Ser Leu Val Ser Leu Pro Thr Glu Ser Thr Lys Ala Val Thr
                805                 810                 815 aca aac tct cct ttg cct cca tcc tta aca gag tcc tcc aca gag caa      2496
Thr Asn Ser Pro Leu Pro Pro Ser Leu Thr Glu Ser Ser Thr Glu Gln
                820                 825                 830 acc ctt cca gcc aca agc acc aac tta gca caa atg tct cca act ttc      2544
Thr Leu Pro Ala Thr Ser Thr Asn Leu Ala Gln Met Ser Pro Thr Phe
        835                 840                 845 aca act acc att ctg aag acc tct cag cct ctt atg acc act cct ggc      2592
Thr Thr Thr Ile Leu Lys Thr Ser Gln Pro Leu Met Thr Thr Pro Gly
850                 855                 860 acc ctg tca agc aca gca tct ctg gtc act ggc cct ata gcc gta cag      2640
Thr Leu Ser Ser Thr Ala Ser Leu Val Thr Gly Pro Ile Ala Val Gln
865                 870                 875                 880 act aca gct gga aaa cag ctc tcg ctg acc cat cct gaa ata cta gtt      2688
Thr Thr Ala Gly Lys Gln Leu Ser Leu Thr His Pro Glu Ile Leu Val
                885                 890                 895 cct caa atc tca aca gaa ggt ggc atc agc aca gaa agg aac cga gtg      2736
Pro Gln Ile Ser Thr Glu Gly Gly Ile Ser Thr Glu Arg Asn Arg Val
                900                 905                 910
```

```
att gtg gat gct acc tct gga ttg atc cct ttg acc agt gta ccc aca         2784
Ile Val Asp Ala Thr Ser Gly Leu Ile Pro Leu Thr Ser Val Pro Thr
        915                 920                 925 tca gca aaa gaa atg acc aca aag ctt ggc gtt aca gca gag tac agc         2832
Ser Ala Lys Glu Met Thr Thr Lys Leu Gly Val Thr Ala Glu Tyr Ser
930                 935                 940 cca gct tca cgt tcc ctc gga aca tct cct tct ccc caa acc aca gtt         2880
Pro Ala Ser Arg Ser Leu Gly Thr Ser Pro Ser Pro Gln Thr Thr Val
945                 950                 955                 960 gtt tcc acg gct gaa gac ttg gct ccc aaa tct gcc acc ttt gct gtt         2928
Val Ser Thr Ala Glu Asp Leu Ala Pro Lys Ser Ala Thr Phe Ala Val
                965                 970                 975 cag agc agc aca cag tca cca aca aca ctg tcc tct tca gcc tca gtc         2976
Gln Ser Ser Thr Gln Ser Pro Thr Thr Leu Ser Ser Ser Ala Ser Val
            980                 985                 990 aac agc tgt gct gtg aac cct tgt ctt cac aat ggc gaa tgc gtc gca         3024
Asn Ser Cys Ala Val Asn Pro Cys Leu His Asn Gly Glu Cys Val Ala
        995                 1000                1005 gac aac acc agc cgt ggc tac cac tgc agg tgc ccg cct tcc tgg              3069
Asp Asn Thr Ser Arg Gly Tyr His Cys Arg Cys Pro Pro Ser Trp
1010                1015                1020 caa ggg gat gat tgc agt gtg gat gtg aat gag tgc ctg tcg aac              3114
Gln Gly Asp Asp Cys Ser Val Asp Val Asn Glu Cys Leu Ser Asn
1025                1030                1035 ccc tgc cca tcc aca gcc atg tgc aac aat act cag gga tcc ttt              3159
Pro Cys Pro Ser Thr Ala Met Cys Asn Asn Thr Gln Gly Ser Phe
1040                1045                1050 atc tgc aaa tgc ccg gtt ggg tac cag ttg gaa aaa ggg ata tgc              3204
Ile Cys Lys Cys Pro Val Gly Tyr Gln Leu Glu Lys Gly Ile Cys
1055                1060                1065 aat ttg gtt aga acc ttc gtg aca gag ttt aaa tta aag aga act              3249
Asn Leu Val Arg Thr Phe Val Thr Glu Phe Lys Leu Lys Arg Thr
1070                1075                1080 ttt ctt aat aca act gtg gaa aaa cat tca gac cta caa gaa gtt              3294
Phe Leu Asn Thr Thr Val Glu Lys His Ser Asp Leu Gln Glu Val
1085                1090                1095 gaa aat gag atc acc aaa acg tta aat atg tgt ttt tca gcg tta              3339
Glu Asn Glu Ile Thr Lys Thr Leu Asn Met Cys Phe Ser Ala Leu
1100                1105                1110 cct agt tac atc cga tct aca gtt cac gcc tct agg gag tcc aac              3384
Pro Ser Tyr Ile Arg Ser Thr Val His Ala Ser Arg Glu Ser Asn
1115                1120                1125 gcg gtg gtg atc tca ctg caa aca acc ttt tcc ctg gcc tcc aat              3429
Ala Val Val Ile Ser Leu Gln Thr Thr Phe Ser Leu Ala Ser Asn
1130                1135                1140 gtg acg cta ttt gac ctg gct gat agg atg cag aaa tgt gtc aac              3474
Val Thr Leu Phe Asp Leu Ala Asp Arg Met Gln Lys Cys Val Asn
1145                1150                1155 tcc tgc aag tcc tct gct gag gtc tgc cag ctc ttg gga tct cag              3519
Ser Cys Lys Ser Ser Ala Glu Val Cys Gln Leu Leu Gly Ser Gln
1160                1165                1170 agg cgg atc ttt aga gcg ggc agc ttg tgc aag cgg aag agt ccc              3564
Arg Arg Ile Phe Arg Ala Gly Ser Leu Cys Lys Arg Lys Ser Pro
1175                1180                1185 gaa tgt gac aaa gac acc tcc atc tgc act gac ctg gac ggc gtt              3609
Glu Cys Asp Lys Asp Thr Ser Ile Cys Thr Asp Leu Asp Gly Val
1190                1195                1200 gcc ctg tgc cag tgc aag tcg gga tac ttt cag ttc aac aag atg              3654
Ala Leu Cys Gln Cys Lys Ser Gly Tyr Phe Gln Phe Asn Lys Met
1205                1210                1215
```

```
gac cac tcc tgc cga gca tgt gaa gat gga tat agg ctt gaa aat        3699
Asp His Ser Cys Arg Ala Cys Glu Asp Gly Tyr Arg Leu Glu Asn
    1220            1225                1230 gaa acc tgc atg agt tgc cca ttt ggc ctt ggt ggt ctc aac tgt        3744
Glu Thr Cys Met Ser Cys Pro Phe Gly Leu Gly Gly Leu Asn Cys
    1235            1240                1245 gga aac ccc tat cag ctt atc act gtg gtg atc gca gcc gcg gga        3789
Gly Asn Pro Tyr Gln Leu Ile Thr Val Val Ile Ala Ala Ala Gly
    1250            1255                1260 ggt ggg ctc ctg ctc atc cta ggc atc gca ctg att gtt acc tgt        3834
Gly Gly Leu Leu Leu Ile Leu Gly Ile Ala Leu Ile Val Thr Cys
    1265            1270                1275 tgc aga aag aat aaa aat gac ata agc aaa ctc atc ttc aaa agt        3879
Cys Arg Lys Asn Lys Asn Asp Ile Ser Lys Leu Ile Phe Lys Ser
    1280            1285                1290 gga gat ttc caa atg tcc cca tat gct gaa tac ccc aaa aat cct        3924
Gly Asp Phe Gln Met Ser Pro Tyr Ala Glu Tyr Pro Lys Asn Pro
    1295            1300                1305 cgc tca caa gaa tgg ggc cga gaa gct att gaa atg cat gag aat        3969
Arg Ser Gln Glu Trp Gly Arg Glu Ala Ile Glu Met His Glu Asn
    1310            1315                1320 gga agt acc aaa aac ctc ctc cag atg acg gat gtg tac tac tcg        4014
Gly Ser Thr Lys Asn Leu Leu Gln Met Thr Asp Val Tyr Tyr Ser
    1325            1330                1335 cct aca agt gta agg aat cca gaa ctt gaa cga aac gga ctc tac        4059
Pro Thr Ser Val Arg Asn Pro Glu Leu Glu Arg Asn Gly Leu Tyr
    1340            1345                1350 ccg gcc tac act gga ctg cca gga tca cgg cat tct tgc att ttc        4104
Pro Ala Tyr Thr Gly Leu Pro Gly Ser Arg His Ser Cys Ile Phe
    1355            1360                1365 ccc gga cag tat aac ccg tct ttc atc agt gat gaa agc aga aga        4149
Pro Gly Gln Tyr Asn Pro Ser Phe Ile Ser Asp Glu Ser Arg Arg
    1370            1375                1380 aga gac tac ttt taa                                                 4164
Arg Asp Tyr Phe
    1385

<210> SEQ ID NO 35
<211> LENGTH: 1387
<212> TYPE: PRT
<213> ORGANISM: Homo sapiens

<400> SEQUENCE: 35

Met Ala Ser Pro Arg Ala Ser Arg Trp Pro Pro Leu Leu Leu Leu
1               5                   10                  15

Leu Leu Pro Leu Leu Leu Leu Pro Pro Ala Ala Pro Gly Thr Arg Asp
                20                  25                  30

Pro Pro Pro Ser Pro Ala Arg Arg Ala Leu Ser Leu Ala Pro Leu Ala
        35                  40                  45

Gly Ala Gly Leu Glu Leu Gln Leu Glu Arg Arg Pro Glu Arg Glu Pro
    50                  55                  60

Pro Pro Thr Pro Pro Arg Glu Arg Arg Gly Pro Ala Thr Pro Gly Pro
65                  70                  75                  80

Ser Tyr Arg Ala Pro Glu Pro Gly Ala Ala Thr Gln Arg Gly Pro Ser
                85                  90                  95

Gly Arg Ala Pro Arg Gly Gly Ser Ala Asp Ala Ala Trp Lys His Trp
            100                 105                 110

Pro Glu Ser Asn Thr Glu Ala His Val Glu Asn Ile Thr Phe Tyr Gln
```

-continued

```
            115                 120                 125
Asn Gln Glu Asp Phe Ser Thr Val Ser Ser Lys Glu Gly Val Met Val
130                 135                 140
Gln Thr Ser Gly Lys Ser His Ala Ala Ser Asp Ala Pro Glu Asn Leu
145                 150                 155                 160
Thr Leu Leu Ala Glu Thr Ala Asp Ala Arg Gly Arg Ser Gly Ser Ser
                165                 170                 175
Ser Arg Thr Asn Phe Thr Ile Leu Pro Val Gly Tyr Ser Leu Glu Ile
                180                 185                 190
Ala Thr Ala Leu Thr Ser Gln Ser Gly Asn Leu Ala Ser Glu Ser Leu
                195                 200                 205
His Leu Pro Ser Ser Ser Glu Phe Asp Glu Arg Ile Ala Ala Phe
210                 215                 220
Gln Thr Lys Ser Gly Thr Ala Ser Glu Met Gly Thr Glu Arg Ala Met
225                 230                 235                 240
Gly Leu Ser Glu Glu Trp Thr Val His Ser Gln Glu Ala Thr Thr Ser
                245                 250                 255
Ala Trp Ser Pro Ser Phe Leu Pro Ala Leu Glu Met Gly Glu Leu Thr
                260                 265                 270
Thr Pro Ser Arg Lys Arg Asn Ser Ser Gly Pro Asp Leu Ser Trp Leu
                275                 280                 285
His Phe Tyr Arg Thr Ala Ala Ser Ser Pro Leu Leu Asp Leu Ser Ser
                290                 295                 300
Ser Ser Glu Ser Thr Glu Lys Leu Asn Asn Ser Thr Gly Leu Gln Ser
305                 310                 315                 320
Ser Ser Val Ser Gln Thr Lys Thr Met His Val Ala Thr Val Phe Thr
                325                 330                 335
Asp Gly Gly Pro Arg Thr Leu Arg Ser Leu Thr Val Ser Leu Gly Pro
                340                 345                 350
Val Ser Lys Thr Glu Gly Phe Pro Lys Asp Ser Arg Ile Ala Thr Thr
                355                 360                 365
Ser Ser Ser Val Leu Leu Ser Pro Ser Ala Val Glu Ser Arg Arg Asn
370                 375                 380
Ser Arg Val Thr Gly Asn Pro Gly Asp Glu Glu Phe Ile Glu Pro Ser
385                 390                 395                 400
Thr Glu Asn Glu Phe Gly Leu Thr Ser Leu Arg Trp Gln Asn Asp Ser
                405                 410                 415
Pro Thr Phe Gly Glu His Gln Leu Ala Ser Ser Glu Val Gln Asn
                420                 425                 430
Gly Ser Pro Met Ser Gln Thr Glu Thr Val Ser Arg Ser Val Ala Pro
                435                 440                 445
Met Arg Gly Gly Glu Ile Thr Ala His Trp Leu Leu Thr Asn Ser Thr
                450                 455                 460
Thr Ser Ala Asp Val Thr Gly Ser Ser Ala Ser Tyr Pro Glu Gly Val
465                 470                 475                 480
Asn Ala Ser Val Leu Thr Gln Phe Ser Asp Ser Thr Val Gln Ser Gly
                485                 490                 495
Gly Ser His Thr Ala Leu Gly Asp Arg Ser Tyr Ser Glu Ser Ser Ser
                500                 505                 510
Thr Ser Ser Ser Glu Ser Leu Asn Ser Ser Ala Pro Arg Gly Glu Arg
                515                 520                 525
Ser Ile Ala Gly Ile Ser Tyr Gly Gln Val Arg Gly Thr Ala Ile Glu
                530                 535                 540
```

```
Gln Arg Thr Ser Ser Asp His Thr Asp His Thr Tyr Leu Ser Ser Thr
545                 550                 555                 560

Phe Thr Lys Gly Glu Arg Ala Leu Leu Ser Ile Thr Asp Asn Ser Ser
            565                 570                 575

Ser Ser Asp Ile Val Glu Ser Ser Thr Ser Tyr Ile Lys Ile Ser Asn
        580                 585                 590

Ser Ser His Ser Glu Tyr Ser Ser Phe Phe His Ala Gln Thr Glu Arg
    595                 600                 605

Ser Asn Ile Ser Ser Tyr Asp Gly Glu Tyr Ala Gln Pro Ser Thr Glu
610                 615                 620

Ser Pro Val Leu His Thr Ser Asn Leu Pro Ser Tyr Thr Pro Thr Ile
625                 630                 635                 640

Asn Met Pro Asn Thr Ser Val Val Leu Asp Thr Asp Ala Glu Phe Val
                645                 650                 655

Ser Asp Ser Ser Ser Ser Ser Ser Ser Ser Ser Ser Ser Ser Ser Ser
            660                 665                 670

Ser Ser Ser Ser Ser Ser Gly Pro Pro Leu Pro Leu Pro Ser Val Ser
        675                 680                 685

Gln Ser His His Leu Phe Ser Ser Ile Leu Pro Ser Thr Arg Ala Ser
690                 695                 700

Val His Leu Leu Lys Ser Thr Ser Asp Ala Ser Thr Pro Trp Ser Ser
705                 710                 715                 720

Ser Pro Ser Pro Leu Pro Val Ser Leu Thr Thr Ser Thr Ser Ala Pro
                725                 730                 735

Leu Ser Val Ser Gln Thr Thr Leu Pro Gln Ser Ser Ser Thr Pro Val
            740                 745                 750

Leu Pro Arg Ala Arg Glu Thr Pro Val Thr Ser Phe Gln Thr Ser Thr
            755                 760                 765

Met Thr Ser Phe Met Thr Met Leu His Ser Ser Gln Thr Ala Asp Leu
770                 775                 780

Lys Ser Gln Ser Thr Pro His Gln Glu Lys Val Ile Thr Glu Ser Lys
785                 790                 795                 800

Ser Pro Ser Leu Val Ser Leu Pro Thr Glu Ser Thr Lys Ala Val Thr
                805                 810                 815

Thr Asn Ser Pro Leu Pro Pro Ser Leu Thr Glu Ser Ser Thr Glu Gln
            820                 825                 830

Thr Leu Pro Ala Thr Ser Thr Asn Leu Ala Gln Met Ser Pro Thr Phe
            835                 840                 845

Thr Thr Thr Ile Leu Lys Thr Ser Gln Pro Leu Met Thr Thr Pro Gly
850                 855                 860

Thr Leu Ser Ser Thr Ala Ser Leu Val Thr Gly Pro Ile Ala Val Gln
865                 870                 875                 880

Thr Thr Ala Gly Lys Gln Leu Ser Leu Thr His Pro Glu Ile Leu Val
                885                 890                 895

Pro Gln Ile Ser Thr Glu Gly Gly Ile Ser Thr Glu Arg Asn Arg Val
            900                 905                 910

Ile Val Asp Ala Thr Ser Gly Leu Ile Pro Leu Thr Ser Val Pro Thr
            915                 920                 925

Ser Ala Lys Glu Met Thr Thr Lys Leu Gly Val Thr Ala Glu Tyr Ser
    930                 935                 940

Pro Ala Ser Arg Ser Leu Gly Thr Ser Pro Ser Pro Gln Thr Thr Val
945                 950                 955                 960
```

-continued

Val Ser Thr Ala Glu Asp Leu Ala Pro Lys Ser Ala Thr Phe Ala Val
               965                 970                 975

Gln Ser Ser Thr Gln Ser Pro Thr Thr Leu Ser Ser Ser Ala Ser Val
               980                 985                 990

Asn Ser Cys Ala Val Asn Pro Cys Leu His Asn Gly Glu Cys Val Ala
               995                 1000                1005

Asp Asn Thr Ser Arg Gly Tyr His Cys Arg Cys Pro Pro Ser Trp
    1010                1015                1020

Gln Gly Asp Asp Cys Ser Val Asp Val Asn Glu Cys Leu Ser Asn
    1025                1030                1035

Pro Cys Pro Ser Thr Ala Met Cys Asn Asn Thr Gln Gly Ser Phe
    1040                1045                1050

Ile Cys Lys Cys Pro Val Gly Tyr Gln Leu Glu Lys Gly Ile Cys
    1055                1060                1065

Asn Leu Val Arg Thr Phe Val Thr Glu Phe Lys Leu Lys Arg Thr
    1070                1075                1080

Phe Leu Asn Thr Thr Val Glu Lys His Ser Asp Leu Gln Glu Val
    1085                1090                1095

Glu Asn Glu Ile Thr Lys Thr Leu Asn Met Cys Phe Ser Ala Leu
    1100                1105                1110

Pro Ser Tyr Ile Arg Ser Thr Val His Ala Ser Arg Glu Ser Asn
    1115                1120                1125

Ala Val Val Ile Ser Leu Gln Thr Thr Phe Ser Leu Ala Ser Asn
    1130                1135                1140

Val Thr Leu Phe Asp Leu Ala Asp Arg Met Gln Lys Cys Val Asn
    1145                1150                1155

Ser Cys Lys Ser Ser Ala Glu Val Cys Gln Leu Leu Gly Ser Gln
    1160                1165                1170

Arg Arg Ile Phe Arg Ala Gly Ser Leu Cys Lys Arg Lys Ser Pro
    1175                1180                1185

Glu Cys Asp Lys Asp Thr Ser Ile Cys Thr Asp Leu Asp Gly Val
    1190                1195                1200

Ala Leu Cys Gln Cys Lys Ser Gly Tyr Phe Gln Phe Asn Lys Met
    1205                1210                1215

Asp His Ser Cys Arg Ala Cys Glu Asp Gly Tyr Arg Leu Glu Asn
    1220                1225                1230

Glu Thr Cys Met Ser Cys Pro Phe Gly Leu Gly Gly Leu Asn Cys
    1235                1240                1245

Gly Asn Pro Tyr Gln Leu Ile Thr Val Val Ile Ala Ala Ala Gly
    1250                1255                1260

Gly Gly Leu Leu Leu Ile Leu Gly Ile Ala Leu Ile Val Thr Cys
    1265                1270                1275

Cys Arg Lys Asn Lys Asn Asp Ile Ser Lys Leu Ile Phe Lys Ser
    1280                1285                1290

Gly Asp Phe Gln Met Ser Pro Tyr Ala Glu Tyr Pro Lys Asn Pro
    1295                1300                1305

Arg Ser Gln Glu Trp Gly Arg Glu Ala Ile Glu Met His Glu Asn
    1310                1315                1320

Gly Ser Thr Lys Asn Leu Leu Gln Met Thr Asp Val Tyr Tyr Ser
    1325                1330                1335

Pro Thr Ser Val Arg Asn Pro Glu Leu Glu Arg Asn Gly Leu Tyr
    1340                1345                1350

Pro Ala Tyr Thr Gly Leu Pro Gly Ser Arg His Ser Cys Ile Phe

```
                    1355                1360                1365
             Pro Gly Gln Tyr Asn Pro Ser  Phe Ile Ser Asp Glu  Ser Arg Arg
                 1370                1375                1380

Arg Asp Tyr Phe
                 1385

<210> SEQ ID NO 36
<211> LENGTH: 4446
<212> TYPE: DNA
<213> ORGANISM: Homo sapiens
<220> FEATURE:
<221> NAME/KEY: CDS
<222> LOCATION: (1)..(4443)

<400> SEQUENCE: 36 atg gcc tcg ccg cgc gcc tcg cgg tgg ccg ccg ccg ctc ctg ctg ctg      48
Met Ala Ser Pro Arg Ala Ser Arg Trp Pro Pro Pro Leu Leu Leu Leu
1               5                   10                  15 ttg ctg ccg ctg ctg ctg ctg ccg ccg gcg gcc ccc ggg acg cgg gac      96
Leu Leu Pro Leu Leu Leu Leu Pro Pro Ala Ala Pro Gly Thr Arg Asp
            20                  25                  30 ccg ccg cct tcc ccg gct cgc cgc gcg ctg agc ctg gcg ccc ctc gcg     144
Pro Pro Pro Ser Pro Ala Arg Arg Ala Leu Ser Leu Ala Pro Leu Ala
        35                  40                  45 gga gcg ggg ctg gag ctg cag ctg gag cgc cgc ccg gag cgc gag ccg     192
Gly Ala Gly Leu Glu Leu Gln Leu Glu Arg Arg Pro Glu Arg Glu Pro
    50                  55                  60 ccg ccc acg ccg ccc cgg gag cgc cgc ggg ccc gcg acc ccc ggc ccc     240
Pro Pro Thr Pro Pro Arg Glu Arg Arg Gly Pro Ala Thr Pro Gly Pro
65                  70                  75                  80 agc tac agg gcc cct gag cca ggc gcc gcg aca cag cgg gga ccc tcc     288
Ser Tyr Arg Ala Pro Glu Pro Gly Ala Ala Thr Gln Arg Gly Pro Ser
                85                  90                  95 ggc cgg gcc ccc aga ggc ggg agc gcg gat gct gcc tgg aaa cat tgg     336
Gly Arg Ala Pro Arg Gly Gly Ser Ala Asp Ala Ala Trp Lys His Trp
            100                 105                 110 cca gaa agt aac act gag gcc cat gta gaa aac atc acc ttc tat cag     384
Pro Glu Ser Asn Thr Glu Ala His Val Glu Asn Ile Thr Phe Tyr Gln
        115                 120                 125 aat caa gag gac ttt tca aca gtg tcc tcc aaa gag ggc gtg atg gtt     432
Asn Gln Glu Asp Phe Ser Thr Val Ser Ser Lys Glu Gly Val Met Val
    130                 135                 140 cag acc tct ggg aag agc cat gct gct tcg gat gct cca gaa aac ctc     480
Gln Thr Ser Gly Lys Ser His Ala Ala Ser Asp Ala Pro Glu Asn Leu
145                 150                 155                 160 act cta ctc gct gaa aca gca gat gct aga gga agg agc ggc tct tca     528
Thr Leu Leu Ala Glu Thr Ala Asp Ala Arg Gly Arg Ser Gly Ser Ser
                165                 170                 175 agt aga aca aac ttc acc att ttg cct gtt ggg tac tca ctg gag ata     576
Ser Arg Thr Asn Phe Thr Ile Leu Pro Val Gly Tyr Ser Leu Glu Ile
            180                 185                 190 gca aca gct ctg act tcc cag agt ggc aac tta gcc tca gaa agt ctt     624
Ala Thr Ala Leu Thr Ser Gln Ser Gly Asn Leu Ala Ser Glu Ser Leu
        195                 200                 205 cac ctg cca tcc agc agt tca gag ttc gat gaa aga att gcc gct ttt     672
His Leu Pro Ser Ser Ser Ser Glu Phe Asp Glu Arg Ile Ala Ala Phe
    210                 215                 220 caa aca aag agt gga aca gcc tcg gag atg gga aca gag agg gcg atg     720
Gln Thr Lys Ser Gly Thr Ala Ser Glu Met Gly Thr Glu Arg Ala Met
225                 230                 235                 240
```

```
ggg ctg tca gaa gaa tgg act gtg cac agc caa gag gcc acc act tcg      768
Gly Leu Ser Glu Glu Trp Thr Val His Ser Gln Glu Ala Thr Thr Ser
            245                 250                 255 gct tgg agc ccg tcc ttt ctt cct gct ttg gag atg gga gag ctg acc      816
Ala Trp Ser Pro Ser Phe Leu Pro Ala Leu Glu Met Gly Glu Leu Thr
            260                 265                 270 acg cct tct agg aag aga aat tcc tca gga cca gat ctc tcc tgg ctg      864
Thr Pro Ser Arg Lys Arg Asn Ser Ser Gly Pro Asp Leu Ser Trp Leu
            275                 280                 285 cat ttc tac agg aca gca gct tcc tct cct ctc tta gac ctt tcc tca      912
His Phe Tyr Arg Thr Ala Ala Ser Ser Pro Leu Leu Asp Leu Ser Ser
            290                 295                 300 tct tct gaa agt aca gag aag ctt aac aac tcc act ggc ctc cag agc      960
Ser Ser Glu Ser Thr Glu Lys Leu Asn Asn Ser Thr Gly Leu Gln Ser
305                 310                 315                 320 tcc tca gtc agt caa aca aag aca atg cat gtt gcc acc gtg ttc act     1008
Ser Ser Val Ser Gln Thr Lys Thr Met His Val Ala Thr Val Phe Thr
            325                 330                 335 gat ggt ggc ccg aga acg ctg cga tct ttg acg gtc agt ctg gga cct     1056
Asp Gly Gly Pro Arg Thr Leu Arg Ser Leu Thr Val Ser Leu Gly Pro
            340                 345                 350 gtg agc aag aca gaa ggc ttc ccc aag gac tcc aga att gcc acg act     1104
Val Ser Lys Thr Glu Gly Phe Pro Lys Asp Ser Arg Ile Ala Thr Thr
            355                 360                 365 tca tcc tca gtc ctt ctt tca ccc tct gca gtg aa tcg aga aga aac      1152
Ser Ser Ser Val Leu Leu Ser Pro Ser Ala Val Glu Ser Arg Arg Asn
            370                 375                 380 agt aga gta act ggg aat cca ggg gat gag gaa ttc att gaa cca tcc     1200
Ser Arg Val Thr Gly Asn Pro Gly Asp Glu Glu Phe Ile Glu Pro Ser
385                 390                 395                 400 aca gaa aat gaa ttt gga ctt acg tct ttg cgt tgg caa aat gat tcc     1248
Thr Glu Asn Glu Phe Gly Leu Thr Ser Leu Arg Trp Gln Asn Asp Ser
            405                 410                 415 cca acc ttt gga gaa cat cag ctt gcc agc agc tct gag gtg caa aat     1296
Pro Thr Phe Gly Glu His Gln Leu Ala Ser Ser Ser Glu Val Gln Asn
            420                 425                 430 gga agt ccc atg tct cag act gag act gtg tct agg tca gtc gca ccc     1344
Gly Ser Pro Met Ser Gln Thr Glu Thr Val Ser Arg Ser Val Ala Pro
            435                 440                 445 atg aga ggt gga gag atc act gca cac tgg ctc ttg acc aac agc aca     1392
Met Arg Gly Gly Glu Ile Thr Ala His Trp Leu Leu Thr Asn Ser Thr
450                 455                 460 aca tct gca gat gtg aca gga agc tct gct tca tat cct gaa ggt gtg     1440
Thr Ser Ala Asp Val Thr Gly Ser Ser Ala Ser Tyr Pro Glu Gly Val
465                 470                 475                 480 aat gct tca gtg ttg acc cag ttc tca gac tct act gta cag tct gga     1488
Asn Ala Ser Val Leu Thr Gln Phe Ser Asp Ser Thr Val Gln Ser Gly
            485                 490                 495 gga agt cac aca gca ttg gga gat agg agt tat tca gag tct tca tct     1536
Gly Ser His Thr Ala Leu Gly Asp Arg Ser Tyr Ser Glu Ser Ser Ser
            500                 505                 510 aca tct tcc tcg gaa agc ttg aat tca tca gca cca cgt gga gaa cgt     1584
Thr Ser Ser Ser Glu Ser Leu Asn Ser Ser Ala Pro Arg Gly Glu Arg
            515                 520                 525 tcg acc ttg gaa gac agc cga gag cca ggc caa gca cta ggt gac agt     1632
Ser Thr Leu Glu Asp Ser Arg Glu Pro Gly Gln Ala Leu Gly Asp Ser
            530                 535                 540 tcc gcc aat gca gag gac agg act tct ggg gtg ccc tct ctc ggc acc     1680
Ser Ala Asn Ala Glu Asp Arg Thr Ser Gly Val Pro Ser Leu Gly Thr
545                 550                 555                 560
```

| | | |
|---|---|---|
| cac acc ttg gct act gtc act gga aac ggg gaa cgc aca ctg cgg tct<br>His Thr Leu Ala Thr Val Thr Gly Asn Gly Glu Arg Thr Leu Arg Ser<br>565 570 575 | 1728 | |
| gtc acc ctc acc aac acc agc atg agc acg act tct ggg gaa gca ggc<br>Val Thr Leu Thr Asn Thr Ser Met Ser Thr Thr Ser Gly Glu Ala Gly<br>580 585 590 | 1776 | |
| agc cct gca gcg gcc atg cac caa gaa aca gag ggt gcc tct ctg cac<br>Ser Pro Ala Ala Ala Met His Gln Glu Thr Glu Gly Ala Ser Leu His<br>595 600 605 | 1824 | |
| gta aac gtg acg gac gac atg ggc ctg gtc tca cgg tca ctg gcc gcc<br>Val Asn Val Thr Asp Asp Met Gly Leu Val Ser Arg Ser Leu Ala Ala<br>610 615 620 | 1872 | |
| tcc agt gca ctc gga gtc gct ggg att agc tac ggt caa gtg cgt ggc<br>Ser Ser Ala Leu Gly Val Ala Gly Ile Ser Tyr Gly Gln Val Arg Gly<br>625 630 635 640 | 1920 | |
| aca gct att gaa caa agg act tcc agc gac cac aca gac cac acc tac<br>Thr Ala Ile Glu Gln Arg Thr Ser Ser Asp His Thr Asp His Thr Tyr<br>645 650 655 | 1968 | |
| ctg tca tct act ttc acc aaa gga gaa cgg gcg tta ctg tcc att aca<br>Leu Ser Ser Thr Phe Thr Lys Gly Glu Arg Ala Leu Leu Ser Ile Thr<br>660 665 670 | 2016 | |
| gat aac agt tca tcc tca gac att gtg gag agc tca act tct tat att<br>Asp Asn Ser Ser Ser Ser Asp Ile Val Glu Ser Ser Thr Ser Tyr Ile<br>675 680 685 | 2064 | |
| aaa atc tca aac tct tca cat tca gag tat tcc tcc ttt ttt cat gct<br>Lys Ile Ser Asn Ser Ser His Ser Glu Tyr Ser Ser Phe Phe His Ala<br>690 695 700 | 2112 | |
| cag act gag aga agt aac atc tca tcc tat gac ggg gaa tat gct cag<br>Gln Thr Glu Arg Ser Asn Ile Ser Ser Tyr Asp Gly Glu Tyr Ala Gln<br>705 710 715 720 | 2160 | |
| cct tct act gag tcg cca gtt ctg cat aca tcc aac ctt ccg tcc tac<br>Pro Ser Thr Glu Ser Pro Val Leu His Thr Ser Asn Leu Pro Ser Tyr<br>725 730 735 | 2208 | |
| aca ccc acc att aat atg ccg aac act tcg gtt gtt ctg gac act gat<br>Thr Pro Thr Ile Asn Met Pro Asn Thr Ser Val Val Leu Asp Thr Asp<br>740 745 750 | 2256 | |
| gct gag ttt gtt agt gac tcc tcc tcc tcc tct tcc tcc tcc tcc tct<br>Ala Glu Phe Val Ser Asp Ser Ser Ser Ser Ser Ser Ser Ser Ser Ser<br>755 760 765 | 2304 | |
| tct tct tct tca ggg cct cct ttg cct ctg ccc tct gtg tca caa tcc<br>Ser Ser Ser Ser Gly Pro Pro Leu Pro Leu Pro Ser Val Ser Gln Ser<br>770 775 780 | 2352 | |
| cac cat tta ttt tca tca att tta cca tca acc agg gcc tct gtg cat<br>His His Leu Phe Ser Ser Ile Leu Pro Ser Thr Arg Ala Ser Val His<br>785 790 795 800 | 2400 | |
| cta cta aag tct acc tct gat gca tcc aca cca tgg tct tcc tca cca<br>Leu Leu Lys Ser Thr Ser Asp Ala Ser Thr Pro Trp Ser Ser Ser Pro<br>805 810 815 | 2448 | |
| tca cct tta cca gta tcc tta acg aca tct aca tct gcc cca ctt tct<br>Ser Pro Leu Pro Val Ser Leu Thr Thr Ser Thr Ser Ala Pro Leu Ser<br>820 825 830 | 2496 | |
| gtc tca caa aca acc ttg cca cag tca tct tct acc cct gtc ctg ccc<br>Val Ser Gln Thr Thr Leu Pro Gln Ser Ser Ser Thr Pro Val Leu Pro<br>835 840 845 | 2544 | |
| agg gca agg gag act cct gtg act tca ttt cag aca tca aca atg aca<br>Arg Ala Arg Glu Thr Pro Val Thr Ser Phe Gln Thr Ser Thr Met Thr<br>850 855 860 | 2592 | |
| tca ttc atg aca atg ctc cat agt agt caa act gca gac ctt aag agc<br>Ser Phe Met Thr Met Leu His Ser Ser Gln Thr Ala Asp Leu Lys Ser | 2640 | |

-continued

```
              865                 870                 875                 880
cag agc acc cca cac caa gag aaa gtc att aca gaa tca aag tca cca       2688
Gln Ser Thr Pro His Gln Glu Lys Val Ile Thr Glu Ser Lys Ser Pro
                    885                 890                 895 agc ctg gtg tct ctg ccc aca gag tcc acc aaa gct gta aca aca aac       2736
Ser Leu Val Ser Leu Pro Thr Glu Ser Thr Lys Ala Val Thr Thr Asn
            900                 905                 910 tct cct ttg cct cca tcc tta aca gag tcc tcc aca gag caa acc ctt       2784
Ser Pro Leu Pro Pro Ser Leu Thr Glu Ser Ser Thr Glu Gln Thr Leu
        915                 920                 925 cca gcc aca agc acc aac tta gca caa atg tct cca act ttc aca act       2832
Pro Ala Thr Ser Thr Asn Leu Ala Gln Met Ser Pro Thr Phe Thr Thr
    930                 935                 940 acc att ctg aag acc tct cag cct ctt atg acc act cct ggc acc ctg       2880
Thr Ile Leu Lys Thr Ser Gln Pro Leu Met Thr Thr Pro Gly Thr Leu
945                 950                 955                 960 tca agc aca gca tct ctg gtc act ggc cct ata gcc gta cag act aca       2928
Ser Ser Thr Ala Ser Leu Val Thr Gly Pro Ile Ala Val Gln Thr Thr
                965                 970                 975 gct gga aaa cag ctc tcg ctg acc cat cct gaa ata cta gtt cct caa       2976
Ala Gly Lys Gln Leu Ser Leu Thr His Pro Glu Ile Leu Val Pro Gln
            980                 985                 990 atc tca aca gaa ggt ggc atc agc  aca gaa agg aac cga  gtg att gtg     3024
Ile Ser Thr Glu Gly Gly Ile Ser  Thr Glu Arg Asn Arg  Val Ile Val
        995                 1000                1005 gat gct  acc act gga ttg atc  cct ttg acc agt gta  ccc aca tca        3069
Asp Ala  Thr Thr Gly Leu Ile  Pro Leu Thr Ser Val  Pro Thr Ser
    1010                 1015                1020 gca aaa  gaa atg acc aca aag  ctt ggc gtt aca gca  gag tac agc        3114
Ala Lys  Glu Met Thr Thr Lys  Leu Gly Val Thr Ala  Glu Tyr Ser
    1025                 1030                1035 cca gct  tca cgt tcc ctc gga  aca tct cct tct ccc  caa acc aca        3159
Pro Ala  Ser Arg Ser Leu Gly  Thr Ser Pro Ser Pro  Gln Thr Thr
    1040                 1045                1050 gtt gtt  tcc acg gct gaa gac  ttg gct ccc aaa tct  gcc acc ttt        3204
Val Val  Ser Thr Ala Glu Asp  Leu Ala Pro Lys Ser  Ala Thr Phe
    1055                 1060                1065 gct gtt  cag agc agc aca cag  tca cca aca aca gtg  tcc tct tca        3249
Ala Val  Gln Ser Ser Thr Gln  Ser Pro Thr Thr Val  Ser Ser Ser
    1070                 1075                1080 gcc tca  gtc aac agc tgt gct  gtg aac cct tgt ctt  cac aat ggc        3294
Ala Ser  Val Asn Ser Cys Ala  Val Asn Pro Cys Leu  His Asn Gly
    1085                 1090                1095 gaa tgc  gtc gca gac aac acc  agc cgt ggc tac cac  tgc agg tgc        3339
Glu Cys  Val Ala Asp Asn Thr  Ser Arg Gly Tyr His  Cys Arg Cys
    1100                 1105                1110 ccg cct  tcc tgg caa ggg gat  gat tgc agt gtg gat  gtg aat gag        3384
Pro Pro  Ser Trp Gln Gly Asp  Asp Cys Ser Val Asp  Val Asn Glu
    1115                 1120                1125 tgc ctg  tcg aac ccc tgc cca  tcc aca gcc atg tgc  aac aat act        3429
Cys Leu  Ser Asn Pro Cys Pro  Ser Thr Ala Met Cys  Asn Asn Thr
    1130                 1135                1140 cag gga  tcc ttt atc tgc aaa  tgc ccg gtt ggg tac  cag ttg gaa        3474
Gln Gly  Ser Phe Ile Cys Lys  Cys Pro Val Gly Tyr  Gln Leu Glu
    1145                 1150                1155 aaa ggg  ata tgc aat ttg gtt  aga acc ttc gtg aca  gag ttt aaa        3519
Lys Gly  Ile Cys Asn Leu Val  Arg Thr Phe Val Thr  Glu Phe Lys
    1160                 1165                1170 tta aag aga act ttt ctt aat  aca act gtg gaa aaa  cat tca gac         3564
```

```
Leu Lys Arg Thr Phe Leu Asn Thr Thr Val Glu Lys His Ser Asp
1175                1180                1185 cta caa gaa gtt gaa aat gag atc acc aaa acg tta aat atg tgt         3609
Leu Gln Glu Val Glu Asn Glu Ile Thr Lys Thr Leu Asn Met Cys
    1190                1195                1200 ttt tca gcg tta cct agt tac atc cga tct aca gtt cac gcc tct         3654
Phe Ser Ala Leu Pro Ser Tyr Ile Arg Ser Thr Val His Ala Ser
1205                1210                1215 agg gag tcc aac gcg gtg gtg atc tca ctg caa aca acc ttt tcc         3699
Arg Glu Ser Asn Ala Val Val Ile Ser Leu Gln Thr Thr Phe Ser
    1220                1225                1230 ctg gcc tcc aat gtg acg cta ttt gac ctg gct gat agg atg cag         3744
Leu Ala Ser Asn Val Thr Leu Phe Asp Leu Ala Asp Arg Met Gln
1235                1240                1245 aaa tgt gtc aac tcc tgc aag tcc tct gct gag gtc tgc cag ctc         3789
Lys Cys Val Asn Ser Cys Lys Ser Ser Ala Glu Val Cys Gln Leu
    1250                1255                1260 ttg gga tct cag agg cgg atc ttt aga gcg ggc agc ttg tgc aag         3834
Leu Gly Ser Gln Arg Arg Ile Phe Arg Ala Gly Ser Leu Cys Lys
1265                1270                1275 cgg aag agt ccc gaa tgt gac aaa gac acc tcc atc tgc act gac         3879
Arg Lys Ser Pro Glu Cys Asp Lys Asp Thr Ser Ile Cys Thr Asp
    1280                1285                1290 ctg gac ggc gtt gcc ctg tgc cag tgc aag tcg gga tac ttt cag         3924
Leu Asp Gly Val Ala Leu Cys Gln Cys Lys Ser Gly Tyr Phe Gln
1295                1300                1305 ttc aac aag atg gac cac tcc tgc cga gca tgt gaa gat gga tat         3969
Phe Asn Lys Met Asp His Ser Cys Arg Ala Cys Glu Asp Gly Tyr
    1310                1315                1320 agg ctt gaa aat gaa acc tgc atg agt tgc cca ttt ggc ctt ggt         4014
Arg Leu Glu Asn Glu Thr Cys Met Ser Cys Pro Phe Gly Leu Gly
1325                1330                1335 ggt ctc aac tgt gga aac ccc tat cag ctt atc act gtg gtg atc         4059
Gly Leu Asn Cys Gly Asn Pro Tyr Gln Leu Ile Thr Val Val Ile
    1340                1345                1350 gca gcc gcg gga ggt ggg ctc ctc ctc atc cta ggc atc gca ctg         4104
Ala Ala Ala Gly Gly Gly Leu Leu Leu Ile Leu Gly Ile Ala Leu
1355                1360                1365 att gtt acc tgt tgc aga aag aat aaa aat gac ata agc aaa ctc         4149
Ile Val Thr Cys Cys Arg Lys Asn Lys Asn Asp Ile Ser Lys Leu
    1370                1375                1380 atc ttc aaa agt gga gat ttc caa atg tcc ccg tat gct gaa tac         4194
Ile Phe Lys Ser Gly Asp Phe Gln Met Ser Pro Tyr Ala Glu Tyr
1385                1390                1395 ccc aaa aat cct cgc tca caa gaa tgg ggc cga gaa gct att gaa         4239
Pro Lys Asn Pro Arg Ser Gln Glu Trp Gly Arg Glu Ala Ile Glu
    1400                1405                1410 atg cat gag aat gga agt acc aaa aac ctc ctc cag atg acg gat         4284
Met His Glu Asn Gly Ser Thr Lys Asn Leu Leu Gln Met Thr Asp
1415                1420                1425 gtg tac tac tcg cct aca agt gta agg aat cca gaa ctt gaa cga         4329
Val Tyr Tyr Ser Pro Thr Ser Val Arg Asn Pro Glu Leu Glu Arg
    1430                1435                1440 aac gga ctc tac ccg gcc tac act gga ctg cca gga tca cgg cat         4374
Asn Gly Leu Tyr Pro Ala Tyr Thr Gly Leu Pro Gly Ser Arg His
1445                1450                1455 tct tgc att ttc ccc gga cag tat aac ccg tct ttc atc agt gat         4419
Ser Cys Ile Phe Pro Gly Gln Tyr Asn Pro Ser Phe Ile Ser Asp
    1460                1465                1470
```

```
                                                     -continued gaa agc aga aga aga gac tac ttt taa                                    4446
Glu Ser Arg Arg Arg Asp Tyr Phe
    1475                1480

<210> SEQ ID NO 37
<211> LENGTH: 1481
<212> TYPE: PRT
<213> ORGANISM: Homo sapiens

<400> SEQUENCE: 37

Met Ala Ser Pro Arg Ala Ser Arg Trp Pro Pro Leu Leu Leu Leu
1               5                   10                  15

Leu Leu Pro Leu Leu Leu Pro Pro Ala Ala Pro Gly Thr Arg Asp
            20                  25                  30

Pro Pro Pro Ser Pro Ala Arg Arg Ala Leu Ser Leu Ala Pro Leu Ala
            35                  40                  45

Gly Ala Gly Leu Glu Leu Gln Leu Glu Arg Arg Pro Glu Arg Glu Pro
    50                  55                      60

Pro Pro Thr Pro Arg Glu Arg Gly Pro Ala Thr Pro Gly Pro
65              70                  75                  80

Ser Tyr Arg Ala Pro Glu Pro Gly Ala Ala Thr Gln Arg Gly Pro Ser
                85                  90                  95

Gly Arg Ala Pro Arg Gly Gly Ser Ala Asp Ala Ala Trp Lys His Trp
            100                 105                 110

Pro Glu Ser Asn Thr Glu Ala His Val Glu Asn Ile Thr Phe Tyr Gln
            115                 120                 125

Asn Gln Glu Asp Phe Ser Thr Val Ser Ser Lys Glu Gly Val Met Val
130                 135                 140

Gln Thr Ser Gly Lys Ser His Ala Ala Ser Asp Ala Pro Glu Asn Leu
145                 150                 155                 160

Thr Leu Leu Ala Glu Thr Ala Asp Ala Arg Gly Arg Ser Gly Ser Ser
                165                 170                 175

Ser Arg Thr Asn Phe Thr Ile Leu Pro Val Gly Tyr Ser Leu Glu Ile
            180                 185                 190

Ala Thr Ala Leu Thr Ser Gln Ser Gly Asn Leu Ala Ser Glu Ser Leu
            195                 200                 205

His Leu Pro Ser Ser Ser Glu Phe Asp Glu Arg Ile Ala Ala Phe
210                 215                 220

Gln Thr Lys Ser Gly Thr Ala Ser Glu Met Gly Thr Glu Arg Ala Met
225                 230                 235                 240

Gly Leu Ser Glu Glu Trp Thr Val His Ser Gln Glu Ala Thr Thr Ser
                245                 250                 255

Ala Trp Ser Pro Ser Phe Leu Pro Ala Leu Glu Met Gly Glu Leu Thr
            260                 265                 270

Thr Pro Ser Arg Lys Arg Asn Ser Ser Gly Pro Asp Leu Ser Trp Leu
            275                 280                 285

His Phe Tyr Arg Thr Ala Ala Ser Ser Pro Leu Leu Asp Leu Ser Ser
            290                 295                 300

Ser Ser Glu Ser Thr Glu Lys Leu Asn Asn Ser Thr Gly Leu Gln Ser
305                 310                 315                 320

Ser Ser Val Ser Gln Thr Lys Thr Met His Val Ala Thr Val Phe Thr
                325                 330                 335

Asp Gly Gly Pro Arg Thr Leu Arg Ser Leu Thr Val Ser Leu Gly Pro
            340                 345                 350

Val Ser Lys Thr Glu Gly Phe Pro Lys Asp Ser Arg Ile Ala Thr Thr
```

-continued

```
                355                 360                 365
Ser Ser Ser Val Leu Ser Pro Ser Ala Val Glu Ser Arg Arg Asn
370                 375                 380
Ser Arg Val Thr Gly Asn Pro Gly Asp Glu Glu Phe Ile Glu Pro Ser
385                 390                 395                 400
Thr Glu Asn Glu Phe Gly Leu Thr Ser Leu Arg Trp Gln Asn Asp Ser
                405                 410                 415
Pro Thr Phe Gly Glu His Gln Leu Ala Ser Ser Glu Val Gln Asn
                420                 425                 430
Gly Ser Pro Met Ser Gln Thr Glu Thr Val Ser Arg Ser Val Ala Pro
                435                 440                 445
Met Arg Gly Gly Glu Ile Thr Ala His Trp Leu Leu Thr Asn Ser Thr
                450                 455                 460
Thr Ser Ala Asp Val Thr Gly Ser Ser Ala Ser Tyr Pro Glu Gly Val
465                 470                 475                 480
Asn Ala Ser Val Leu Thr Gln Phe Ser Asp Ser Thr Val Gln Ser Gly
                485                 490                 495
Gly Ser His Thr Ala Leu Gly Asp Arg Ser Tyr Ser Glu Ser Ser Ser
                500                 505                 510
Thr Ser Ser Ser Glu Ser Leu Asn Ser Ser Ala Pro Arg Gly Glu Arg
                515                 520                 525
Ser Thr Leu Glu Asp Ser Arg Glu Pro Gly Gln Ala Leu Gly Asp Ser
                530                 535                 540
Ser Ala Asn Ala Glu Asp Arg Thr Ser Gly Val Pro Ser Leu Gly Thr
545                 550                 555                 560
His Thr Leu Ala Thr Val Thr Gly Asn Gly Glu Arg Thr Leu Arg Ser
                565                 570                 575
Val Thr Leu Thr Asn Thr Ser Met Ser Thr Thr Ser Gly Glu Ala Gly
                580                 585                 590
Ser Pro Ala Ala Met His Gln Glu Thr Glu Gly Ala Ser Leu His
                595                 600                 605
Val Asn Val Thr Asp Asp Met Gly Leu Val Ser Arg Ser Leu Ala Ala
                610                 615                 620
Ser Ser Ala Leu Gly Val Ala Gly Ile Ser Tyr Gly Gln Val Arg Gly
625                 630                 635                 640
Thr Ala Ile Glu Gln Arg Thr Ser Ser Asp His Thr Asp His Thr Tyr
                645                 650                 655
Leu Ser Ser Thr Phe Thr Lys Gly Glu Arg Ala Leu Leu Ser Ile Thr
                660                 665                 670
Asp Asn Ser Ser Ser Ser Asp Ile Val Glu Ser Ser Thr Ser Tyr Ile
                675                 680                 685
Lys Ile Ser Asn Ser Ser His Ser Glu Tyr Ser Ser Phe Phe His Ala
                690                 695                 700
Gln Thr Glu Arg Ser Asn Ile Ser Ser Tyr Asp Gly Glu Tyr Ala Gln
705                 710                 715                 720
Pro Ser Thr Glu Ser Pro Val Leu His Thr Ser Asn Leu Pro Ser Tyr
                725                 730                 735
Thr Pro Thr Ile Asn Met Pro Asn Thr Ser Val Val Leu Asp Thr Asp
                740                 745                 750
Ala Glu Phe Val Ser Asp Ser Ser Ser Ser Ser Ser Ser Ser Ser
                755                 760                 765
Ser Ser Ser Ser Gly Pro Pro Leu Pro Leu Pro Ser Val Ser Gln Ser
770                 775                 780
```

```
His His Leu Phe Ser Ser Ile Leu Pro Ser Thr Arg Ala Ser Val His
785                 790                 795                 800

Leu Leu Lys Ser Thr Ser Asp Ala Ser Thr Pro Trp Ser Ser Ser Pro
            805                 810                 815

Ser Pro Leu Pro Val Ser Leu Thr Thr Ser Thr Ser Ala Pro Leu Ser
        820                 825                 830

Val Ser Gln Thr Thr Leu Pro Gln Ser Ser Ser Thr Pro Val Leu Pro
        835                 840                 845

Arg Ala Arg Glu Thr Pro Val Thr Ser Phe Gln Thr Ser Thr Met Thr
    850                 855                 860

Ser Phe Met Thr Met Leu His Ser Ser Gln Thr Ala Asp Leu Lys Ser
865                 870                 875                 880

Gln Ser Thr Pro His Gln Glu Lys Val Ile Thr Glu Ser Lys Ser Pro
                885                 890                 895

Ser Leu Val Ser Leu Pro Thr Glu Ser Thr Lys Ala Val Thr Thr Asn
            900                 905                 910

Ser Pro Leu Pro Pro Ser Leu Thr Glu Ser Thr Glu Gln Thr Leu
            915                 920                 925

Pro Ala Thr Ser Thr Asn Leu Ala Gln Met Ser Pro Thr Phe Thr Thr
    930                 935                 940

Thr Ile Leu Lys Thr Ser Gln Pro Leu Met Thr Thr Pro Gly Thr Leu
945                 950                 955                 960

Ser Ser Thr Ala Ser Leu Val Thr Gly Pro Ile Ala Val Gln Thr Thr
                965                 970                 975

Ala Gly Lys Gln Leu Ser Leu Thr His Pro Glu Ile Leu Val Pro Gln
            980                 985                 990

Ile Ser Thr Glu Gly Gly Ile Ser Thr Glu Arg Asn Arg Val Ile Val
        995                 1000                1005

Asp Ala Thr Thr Gly Leu Ile Pro Leu Thr Ser Val Pro Thr Ser
    1010                1015                1020

Ala Lys Glu Met Thr Thr Lys Leu Gly Val Thr Ala Glu Tyr Ser
    1025                1030                1035

Pro Ala Ser Arg Ser Leu Gly Thr Ser Pro Ser Pro Gln Thr Thr
    1040                1045                1050

Val Val Ser Thr Ala Glu Asp Leu Ala Pro Lys Ser Ala Thr Phe
    1055                1060                1065

Ala Val Gln Ser Ser Thr Gln Ser Pro Thr Thr Val Ser Ser Ser
    1070                1075                1080

Ala Ser Val Asn Ser Cys Ala Val Asn Pro Cys Leu His Asn Gly
    1085                1090                1095

Glu Cys Val Ala Asp Asn Thr Ser Arg Gly Tyr His Cys Arg Cys
    1100                1105                1110

Pro Pro Ser Trp Gln Gly Asp Asp Cys Ser Val Asp Val Asn Glu
    1115                1120                1125

Cys Leu Ser Asn Pro Cys Pro Ser Thr Ala Met Cys Asn Asn Thr
    1130                1135                1140

Gln Gly Ser Phe Ile Cys Lys Cys Pro Val Gly Tyr Gln Leu Glu
    1145                1150                1155

Lys Gly Ile Cys Asn Leu Val Arg Thr Phe Val Thr Glu Phe Lys
    1160                1165                1170

Leu Lys Arg Thr Phe Leu Asn Thr Thr Val Glu Lys His Ser Asp
    1175                1180                1185
```

| | | | | | | | | | | |
|---|---|---|---|---|---|---|---|---|---|---|
| Leu | Gln | Glu | Val | Glu | Asn | Glu | Ile | Thr | Lys | Thr | Leu | Asn | Met | Cys |
| | 1190 | | | | 1195 | | | | 1200 | |

Phe Ser Ala Leu Pro Ser Tyr Ile Arg Ser Thr Val His Ala Ser
    1205                1210                1215

Arg Glu Ser Asn Ala Val Val Ile Ser Leu Gln Thr Thr Phe Ser
    1220                1225                1230

Leu Ala Ser Asn Val Thr Leu Phe Asp Leu Ala Asp Arg Met Gln
    1235                1240                1245

Lys Cys Val Asn Ser Cys Lys Ser Ser Ala Glu Val Cys Gln Leu
    1250                1255                1260

Leu Gly Ser Gln Arg Arg Ile Phe Arg Ala Gly Ser Leu Cys Lys
    1265                1270                1275

Arg Lys Ser Pro Glu Cys Asp Lys Asp Thr Ser Ile Cys Thr Asp
    1280                1285                1290

Leu Asp Gly Val Ala Leu Cys Gln Cys Lys Ser Gly Tyr Phe Gln
    1295                1300                1305

Phe Asn Lys Met Asp His Ser Cys Arg Ala Cys Glu Asp Gly Tyr
    1310                1315                1320

Arg Leu Glu Asn Glu Thr Cys Met Ser Cys Pro Phe Gly Leu Gly
    1325                1330                1335

Gly Leu Asn Cys Gly Asn Pro Tyr Gln Leu Ile Thr Val Val Ile
    1340                1345                1350

Ala Ala Ala Gly Gly Gly Leu Leu Leu Ile Leu Gly Ile Ala Leu
    1355                1360                1365

Ile Val Thr Cys Cys Arg Lys Asn Lys Asn Asp Ile Ser Lys Leu
    1370                1375                1380

Ile Phe Lys Ser Gly Asp Phe Gln Met Ser Pro Tyr Ala Glu Tyr
    1385                1390                1395

Pro Lys Asn Pro Arg Ser Gln Glu Trp Gly Arg Glu Ala Ile Glu
    1400                1405                1410

Met His Glu Asn Gly Ser Thr Lys Asn Leu Leu Gln Met Thr Asp
    1415                1420                1425

Val Tyr Tyr Ser Pro Thr Ser Val Arg Asn Pro Glu Leu Glu Arg
    1430                1435                1440

Asn Gly Leu Tyr Pro Ala Tyr Thr Gly Leu Pro Gly Ser Arg His
    1445                1450                1455

Ser Cys Ile Phe Pro Gly Gln Tyr Asn Pro Ser Phe Ile Ser Asp
    1460                1465                1470

Glu Ser Arg Arg Arg Asp Tyr Phe
    1475                1480

<210> SEQ ID NO 38
<211> LENGTH: 21
<212> TYPE: RNA
<213> ORGANISM: Artificial Sequence
<220> FEATURE:
<223> OTHER INFORMATION: H3059 sense

<400> SEQUENCE: 38
gcgaaugcgu cgcagacaac a                                              21

<210> SEQ ID NO 39
<211> LENGTH: 21
<212> TYPE: RNA
<213> ORGANISM: Artificial Sequence
<220> FEATURE:
<223> OTHER INFORMATION: H3059 antisense

<400> SEQUENCE: 39
uugucugcga cgcauucgcc a                                                      21

<210> SEQ ID NO 40
<211> LENGTH: 21
<212> TYPE: RNA
<213> ORGANISM: Artificial Sequence
<220> FEATURE:
<223> OTHER INFORMATION: H9106 sense

<400> SEQUENCE: 40
cuggcguucu agucaguaaa a                                                      21

<210> SEQ ID NO 41
<211> LENGTH: 21
<212> TYPE: RNA
<213> ORGANISM: Artificial Sequence
<220> FEATURE:
<223> OTHER INFORMATION: H9106 antisense

<400> SEQUENCE: 41
uuacugacua gaacgccaga c                                                      21

<210> SEQ ID NO 42
<211> LENGTH: 111
<212> TYPE: PRT
<213> ORGANISM: Artificial Sequence
<220> FEATURE:
<223> OTHER INFORMATION: SLURPgpi

<400> SEQUENCE: 42

Gly Ser Leu Lys Cys Tyr Thr Cys Lys Glu Pro Met Thr Ser Ala Ser
1               5                   10                  15

Cys Arg Thr Ile Thr Arg Cys Lys Pro Glu Asp Thr Ala Cys Met Thr
            20                  25                  30

Thr Leu Val Thr Val Glu Ala Glu Tyr Pro Phe Asn Gln Ser Pro Val
        35                  40                  45

Val Thr Arg Ser Cys Ser Ser Ser Cys Val Ala Thr Asp Pro Asp Ser
    50                  55                  60

Ile Gly Ala Ala His Leu Ile Phe Cys Cys Phe Arg Asp Leu Cys Asn
65                  70                  75                  80

Ser Glu Leu Ser Arg Asp Gly Ala Pro Ser Leu Gly Ser Pro Gly Gly
                85                  90                  95

Leu Leu Leu Ala Leu Ala Leu Phe Leu Leu Gly Val Leu Leu
            100                 105                 110

<210> SEQ ID NO 43
<211> LENGTH: 34
<212> TYPE: PRT
<213> ORGANISM: Artificial Sequence
<220> FEATURE:
<223> OTHER INFORMATION: Signal sequence for SLURPgpi-fusion

<400> SEQUENCE: 43

Met Ala Ser Pro Arg Ala Ser Arg Trp Pro Pro Leu Leu Leu Leu
1               5                   10                  15

Leu Leu Pro Leu Leu Leu Leu Pro Pro Ala Ala Pro Gly Thr Arg Asp
            20                  25                  30

Gly Thr

-continued

```
<210> SEQ ID NO 44
<211> LENGTH: 20
<212> TYPE: PRT
<213> ORGANISM: Artificial Sequence
<220> FEATURE:
<223> OTHER INFORMATION: 7.61 - SLURPgpi (7.61)

<400> SEQUENCE: 44

Asp Leu Lys Ser Gln Ser Thr Pro His Gln Glu Lys Val Ile Thr Glu
1               5                   10                  15

Ser Lys Ser Pro
            20

<210> SEQ ID NO 45
<211> LENGTH: 20
<212> TYPE: PRT
<213> ORGANISM: Artificial Sequence
<220> FEATURE:
<223> OTHER INFORMATION: 7.62 - SLURPgpi (7.62)

<400> SEQUENCE: 45

Glu Lys Val Ile Thr Glu Ser Lys Ser Pro Ser Leu Val Ser Leu Pro
1               5                   10                  15

Thr Glu Ser Thr
            20

<210> SEQ ID NO 46
<211> LENGTH: 20
<212> TYPE: PRT
<213> ORGANISM: Artificial Sequence
<220> FEATURE:
<223> OTHER INFORMATION: 7.63 - SLURPgpi (7.63)

<400> SEQUENCE: 46

Ser Leu Val Ser Leu Pro Thr Glu Ser Thr Lys Ala Val Thr Thr Asn
1               5                   10                  15

Ser Pro Leu Pro
            20

<210> SEQ ID NO 47
<211> LENGTH: 19
<212> TYPE: PRT
<213> ORGANISM: Artificial Sequence
<220> FEATURE:
<223> OTHER INFORMATION: 7.64 - SLURPgpi (7.64)

<400> SEQUENCE: 47

Lys Ala Val Thr Thr Asn Ser Pro Leu Pro Pro Ser Leu Thr Glu Ser
1               5                   10                  15

Ser Thr Glu

<210> SEQ ID NO 48
<211> LENGTH: 14
<212> TYPE: PRT
<213> ORGANISM: Artificial Sequence
<220> FEATURE:
<223> OTHER INFORMATION: 7.623 - SLURPgpi (7.623)

<400> SEQUENCE: 48

Ser Lys Ser Pro Ser Leu Val Ser Leu Pro Thr Glu Ser Thr
1               5                   10

<210> SEQ ID NO 49
<211> LENGTH: 16
<212> TYPE: PRT
```

```
<213> ORGANISM: Artificial Sequence
<220> FEATURE:
<223> OTHER INFORMATION: 7.6231 - SLURPgpi (7.6231)

<400> SEQUENCE: 49

Gly Gly Ser Lys Ser Pro Ser Leu Val Ser Leu Pro Thr Glu Gly Gly
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: 7.6232 - SLURPgpi (7.6232)

<400> SEQUENCE: 50

Gly Gly Lys Ser Pro Ser Leu Val Ser Leu Pro Thr Glu Gly Gly
1               5                   10                  15

<210> SEQ ID NO 51
<211> LENGTH: 14
<212> TYPE: PRT
<213> ORGANISM: Artificial Sequence
<220> FEATURE:
<223> OTHER INFORMATION: 7.6241 - SLURPgpi (7.6241)

<400> SEQUENCE: 51

Gly Gly Ser Pro Ser Leu Val Ser Leu Pro Thr Glu Gly Gly
1               5                   10

<210> SEQ ID NO 52
<211> LENGTH: 13
<212> TYPE: PRT
<213> ORGANISM: Artificial Sequence
<220> FEATURE:
<223> OTHER INFORMATION: 7.6242 - SLURPgpi (7.6242)

<400> SEQUENCE: 52

Gly Gly Pro Ser Leu Val Ser Leu Pro Thr Glu Gly Gly
1               5                   10

<210> SEQ ID NO 53
<211> LENGTH: 11
<212> TYPE: PRT
<213> ORGANISM: Artificial Sequence
<220> FEATURE:
<223> OTHER INFORMATION: S799 - T809 fragment

<400> SEQUENCE: 53

Ser Lys Ser Pro Ser Leu Val Ser Leu Pro Thr
1               5                   10

<210> SEQ ID NO 54
<211> LENGTH: 16
<212> TYPE: PRT
<213> ORGANISM: Artificial Sequence
<220> FEATURE:
<223> OTHER INFORMATION: S799A

<400> SEQUENCE: 54

Gly Gly Ala Lys Ser Pro Ser Leu Val Ser Leu Pro Thr Glu Gly Gly
1               5                   10                  15

<210> SEQ ID NO 55
<211> LENGTH: 16
<212> TYPE: PRT
<213> ORGANISM: Artificial Sequence
```

```
<220> FEATURE:
<223> OTHER INFORMATION: K800A

<400> SEQUENCE: 55

Gly Gly Ser Ala Ser Pro Ser Leu Val Ser Leu Pro Thr Glu Gly Gly
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: S801A

<400> SEQUENCE: 56

Gly Gly Ser Lys Ala Pro Ser Leu Val Ser Leu Pro Thr Glu Gly Gly
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: P802A

<400> SEQUENCE: 57

Gly Gly Ser Lys Ser Ala Ser Leu Val Ser Leu Pro Thr Glu Gly Gly
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: S803A

<400> SEQUENCE: 58

Gly Gly Ser Lys Ser Pro Ala Leu Val Ser Leu Pro Thr Glu Gly Gly
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: L804A

<400> SEQUENCE: 59

Gly Gly Ser Lys Ser Pro Ser Ala Val Ser Leu Pro Thr Glu Gly Gly
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: V805A

<400> SEQUENCE: 60

Gly Gly Ser Lys Ser Pro Ser Leu Ala Ser Leu Pro Thr Glu Gly Gly
1               5                   10                  15

<210> SEQ ID NO 61
<211> LENGTH: 16
<212> TYPE: PRT
<213> ORGANISM: Artificial Sequence
<220> FEATURE:
```

<223> OTHER INFORMATION: S806A

<400> SEQUENCE: 61

Gly Gly Ser Lys Ser Pro Ser Leu Val Ala Leu Pro Thr Glu Gly Gly
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: L807A

<400> SEQUENCE: 62

Gly Gly Ser Lys Ser Pro Ser Leu Val Ser Ala Pro Thr Glu Gly Gly
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: P808A

<400> SEQUENCE: 63

Gly Gly Ser Lys Ser Pro Ser Leu Val Ser Leu Ala Thr Glu Gly Gly
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: T809A

<400> SEQUENCE: 64

Gly Gly Ser Lys Ser Pro Ser Leu Val Ser Leu Pro Ala Glu Gly Gly
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: E810A

<400> SEQUENCE: 65

Gly Gly Ser Lys Ser Pro Ser Leu Val Ser Leu Pro Thr Ala Gly Gly
1               5                   10                  15

<210> SEQ ID NO 66
<211> LENGTH: 49
<212> TYPE: PRT
<213> ORGANISM: Artificial Sequence
<220> FEATURE:
<223> OTHER INFORMATION: Synthetic Construct

<400> SEQUENCE: 66

Asp Leu Lys Ser Gln Ser Thr Pro His Gln Glu Lys Val Ile Thr Glu
1               5                   10                  15

Ser Lys Ser Pro Ser Leu Val Ser Leu Pro Thr Glu Ser Thr Lys Ala
            20                  25                  30

Val Thr Thr Asn Ser Pro Leu Pro Pro Ser Leu Thr Glu Ser Ser Thr
        35                  40                  45

Glu

<210> SEQ ID NO 67
<211> LENGTH: 20
<212> TYPE: PRT
<213> ORGANISM: Artificial Sequence
<220> FEATURE:
<223> OTHER INFORMATION: Synthetic Construct

<400> SEQUENCE: 67

Asp Leu Lys Ser Gln Ser Thr Pro His Gln Glu Lys Val Ile Thr Glu
1               5                   10                  15

Ser Lys Ser Pro
            20

<210> SEQ ID NO 68
<211> LENGTH: 20
<212> TYPE: PRT
<213> ORGANISM: Artificial Sequence
<220> FEATURE:
<223> OTHER INFORMATION: Synthetic Construct

<400> SEQUENCE: 68

Glu Lys Val Ile Thr Glu Ser Lys Ser Pro Ser Leu Val Ser Leu Pro
1               5                   10                  15

Thr Glu Ser Thr
            20

<210> SEQ ID NO 69
<211> LENGTH: 20
<212> TYPE: PRT
<213> ORGANISM: Artificial Sequence
<220> FEATURE:
<223> OTHER INFORMATION: Synthetic Construct

<400> SEQUENCE: 69

Ser Leu Val Ser Leu Pro Thr Glu Ser Thr Lys Ala Val Thr Thr Asn
1               5                   10                  15

Ser Pro Leu Pro
            20

<210> SEQ ID NO 70
<211> LENGTH: 19
<212> TYPE: PRT
<213> ORGANISM: Artificial Sequence
<220> FEATURE:
<223> OTHER INFORMATION: Synthetic Construct

<400> SEQUENCE: 70

Lys Ala Val Thr Thr Asn Ser Pro Leu Pro Ser Leu Thr Glu Ser
1               5                   10                  15

Ser Thr Glu

<210> SEQ ID NO 71
<211> LENGTH: 14
<212> TYPE: PRT
<213> ORGANISM: Artificial Sequence
<220> FEATURE:
<223> OTHER INFORMATION: Synthetic Construct

<400> SEQUENCE: 71

Ser Lys Ser Pro Ser Leu Val Ser Leu Pro Thr Glu Ser Thr
1               5                   10

<210> SEQ ID NO 72

```
<211> LENGTH: 16
<212> TYPE: PRT
<213> ORGANISM: Artificial Sequence
<220> FEATURE:
<223> OTHER INFORMATION: Synthetic Construct

<400> SEQUENCE: 72

Gly Gly Ser Lys Ser Pro Ser Leu Val Ser Leu Pro Thr Glu Gly Gly
1               5                   10                  15

<210> SEQ ID NO 73
<211> LENGTH: 11
<212> TYPE: PRT
<213> ORGANISM: Artificial Sequence
<220> FEATURE:
<223> OTHER INFORMATION: Synthetic Construct

<400> SEQUENCE: 73

Lys Ser Pro Ser Leu Val Ser Leu Pro Thr Glu
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic Construct

<400> SEQUENCE: 74

Ser Pro Ser Leu Val Ser Leu Pro Thr Glu
1               5                   10

<210> SEQ ID NO 75
<211> LENGTH: 9
<212> TYPE: PRT
<213> ORGANISM: Artificial Sequence
<220> FEATURE:
<223> OTHER INFORMATION: Synthetic Construct

<400> SEQUENCE: 75

Pro Ser Leu Val Ser Leu Pro Thr Glu
1               5

<210> SEQ ID NO 76
<211> LENGTH: 12
<212> TYPE: PRT
<213> ORGANISM: Artificial Sequence
<220> FEATURE:
<223> OTHER INFORMATION: Synthetic Construct

<400> SEQUENCE: 76

Ala Lys Ser Pro Ser Leu Val Ser Leu Pro Thr Glu
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Synthetic Construct

<400> SEQUENCE: 77

Ser Ala Ser Pro Ser Leu Val Ser Leu Pro Thr Glu
1               5                   10

<210> SEQ ID NO 78
<211> LENGTH: 12
```

```
<212> TYPE: PRT
<213> ORGANISM: Artificial Sequence
<220> FEATURE:
<223> OTHER INFORMATION: Synthetic Construct

<400> SEQUENCE: 78

Ser Lys Ala Pro Ser Leu Val Ser Leu Pro Thr Glu
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Synthetic Construct

<400> SEQUENCE: 79

Ser Lys Ser Ala Ser Leu Val Ser Leu Pro Thr Glu
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Synthetic Construct

<400> SEQUENCE: 80

Ser Lys Ser Pro Ala Leu Val Ser Leu Pro Thr Glu
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthetic Construct

<400> SEQUENCE: 81

Ser Lys Ser Pro Ser Ala Val Ser Leu Pro Thr Glu
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic Construct

<400> SEQUENCE: 82

Ser Lys Ser Pro Ser Leu Ala Ser Leu Pro Thr Glu
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic Construct

<400> SEQUENCE: 83

Ser Lys Ser Pro Ser Leu Val Ala Leu Pro Thr Glu
1               5                   10

<210> SEQ ID NO 84
<211> LENGTH: 12
<212> TYPE: PRT
```

```
<213> ORGANISM: Artificial Sequence
<220> FEATURE:
<223> OTHER INFORMATION: Synthetic Construct

<400> SEQUENCE: 84

Ser Lys Ser Pro Ser Leu Val Ser Ala Pro Thr Glu
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic Construct

<400> SEQUENCE: 85

Ser Lys Ser Pro Ser Leu Val Ser Leu Ala Thr Glu
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Synthetic Construct

<400> SEQUENCE: 86

Ser Lys Ser Pro Ser Leu Val Ser Leu Pro Ala Glu
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Synthetic Construct

<400> SEQUENCE: 87

Ser Lys Ser Pro Ser Leu Val Ser Leu Pro Thr Ala
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Synthetic Construct

<400> SEQUENCE: 88

Ser Lys Ser Pro Ser Leu Val Ser Leu Pro Thr Glu
1               5                   10

<210> SEQ ID NO 89
<211> LENGTH: 11
<212> TYPE: PRT
<213> ORGANISM: Artificial Sequence
<220> FEATURE:
<223> OTHER INFORMATION: Synthetic Construct

<400> SEQUENCE: 89

Ser Lys Ser Pro Ser Leu Val Ser Leu Pro Thr
1               5                   10
```